United States Patent
Vaghashiya et al.

(10) Patent No.: US 11,964,048 B2
(45) Date of Patent: **\*Apr. 23, 2024**

(54) SUSTAINED RELEASE COMPOSITIONS COMPRISING LIOTHYRONINE

(71) Applicant: Amneal Complex Products Research LLC, Bridgewater, NJ (US)

(72) Inventors: Jaydeep Vaghashiya, Franklin Park, NJ (US); Dipen Desai, Whippany, NJ (US); Navnit H. Shah, Monmouth Junction, NJ (US); Wantanee Phuapradit, Lewes, DE (US); Kanji Meghpara, Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/342,645

(22) Filed: Jun. 9, 2021

(65) Prior Publication Data

US 2022/0192977 A1    Jun. 23, 2022

Related U.S. Application Data

(60) Provisional application No. 63/208,060, filed on Jun. 8, 2021, provisional application No. 63/127,233, filed on Dec. 18, 2020.

(51) Int. Cl.
    *A61K 9/00*    (2006.01)
    *A61K 9/20*    (2006.01)
    *A61K 9/28*    (2006.01)
    *A61K 31/198*  (2006.01)

(52) U.S. Cl.
    CPC .......... *A61K 9/0065* (2013.01); *A61K 9/0004* (2013.01); *A61K 9/2054* (2013.01); *A61K 9/2086* (2013.01); *A61K 9/2095* (2013.01); *A61K 9/2846* (2013.01); *A61K 31/198* (2013.01)

(58) Field of Classification Search
    CPC .... A61K 9/0065; A61K 9/004; A61K 9/2054; A61K 9/2086; A61K 9/2095; A61K 9/2846; A61K 31/198
    See application file for complete search history.

(56) References Cited

U.S. PATENT DOCUMENTS

| | | | | |
|---|---|---|---|---|
| 5,009,895 | A * | 4/1991 | Lui ................. | A61P 25/04 424/494 |
| 5,681,584 | A | 10/1997 | Savastano et al. | |
| 6,881,420 | B2 | 4/2005 | Fleshner-Barack et al. | |
| 2003/0185888 | A1* | 10/2003 | Wong .................. | A61P 9/10 424/473 |
| 2006/0246133 | A1* | 11/2006 | Beasley .............. | A61K 9/2054 514/567 |
| 2013/0043612 | A1 | 2/2013 | Geerke et al. | |
| 2015/0079136 | A1 | 3/2015 | Pilgaonkar et al. | |
| 2020/0155446 | A1* | 5/2020 | Shah ................... | A61K 31/198 |

FOREIGN PATENT DOCUMENTS

| WO | WO 03/061557 A3 | 7/2003 |
|---|---|---|
| WO | WO 2020/006278 A1 | 1/2020 |

OTHER PUBLICATIONS

Sungthongjeen et al. Eur J Pharm Biopharm. 2008; 69: 255-263. (Year: 2008).*
Malaterre, Vincent, et al., Oral osmotically driven systems: 30 years of development and clinical use, European J of Phamaceutics and Biopharmaceutics, vol. 73 (2009), pp. 311-323.
International Search Report.

* cited by examiner

*Primary Examiner* — David Browe

(57) ABSTRACT

The present disclosure provides floating gastroretentive compositions comprising a multilayer core comprising 1) a pull layer containing liothyronine or a pharmaceutically acceptable salt thereof, an acid, and a gas-generating agent; and 2) a push layer. Each of the pull layer and the push layer comprises a swellable water-soluble hydrophilic polymer. The composition further comprises a permeable elastic membrane covering at least a portion of the multilayer core and containing at least one orifice in fluid communication with the pull layer. The permeable elastic membrane comprises a copolymer of ethyl acrylate, methyl methacrylate, and trimethylammonioethyl methacrylate chloride. The composition provides sustained release of liothyronine or a pharmaceutically acceptable salt thereof.

25 Claims, 10 Drawing Sheets

SUSTAINED RELEASE COMPOSITIONS COMPRISING LIOTHYRONINE

1. RELATED APPLICATIONS

This application claims priority to U.S. Provisional Patent Application No. 63/127,233, filed Dec. 18, 2020, and U.S. Provisional Patent Application No. 63/208,060, filed Jun. 8, 2021, the disclosures of which are hereby incorporated by reference herein in their entirety.

2. TECHNICAL FIELD

The present disclosure provides sustained release pharmaceutical compositions that include a thyroid hormone, such as liothyronine or a pharmaceutically acceptable salt thereof. In particular, the present disclosure provides osmotic, gastroretentive compositions of liothyronine (T3) or a pharmaceutically acceptable salt thereof, suitable for once-daily administration. The compositions provide sustained release with enhanced pharmacokinetic (PK) attributes of liothyronine, e.g., reduced burst release/blunted $C_{max}$, reduced peak-to-trough ratios ($C_{max}/C_{min}$), as compared to marketed immediate release liothyronine products. The gastroretentive compositions of the disclosure rely on floating and swelling properties of the composition to retain the composition in stomach for an extended period, thus providing sustained release of thyroid hormone in the upper gastro-intestinal (GI) region for continuous absorption.

3. BACKGROUND

Thyroid hormone preparations of levothyroxine and/or liothyronine are useful in the treatment of hypothyroidism and thyroid hormone replacement therapy in mammals, for example, humans and dogs.

Thyroid hormone drugs are natural or synthetic preparations containing tetraiodothyronine (T4/levothyroxine) or triiodothyronine (T3/liothyronine) or both, usually as their pharmaceutically acceptable salts. Thyroid hormone drugs exhibit a narrow absorption window in the upper GI tract and exhibit high inter- and intra-subject variability. See, e.g., WO2008/057464. Thyroid hormone replacement therapy is established for each patient individually. Generally, the initial dose is small, and the amount is increased gradually until an optimal test response is achieved. Dose titration of thyroid hormones is critical for an optimal response. Both under-treatment and over-treatment can provide deleterious health impacts. Under-treatment has also been reported to be a potential factor in decreased cardiac contractility and increased risk of coronary artery disease. Conversely, over-treatment may result in toxic manifestations of hyperthyroidism, such as cardiac pain, increased pulse rate, palpitations, excessive sweating, heat intolerance, nervousness, or cardiac arrhythmias.

Once diagnosed, the missing thyroid hormone is generally replaced with a thyroid hormone such as thyroxine (T4). However, for many patients, administration of thyroxine is not a sufficient treatment regimen due to the body's limited capacity to convert thyroxine (T4) to liothyronine (T3), which is biologically more active than thyroxine. For such individuals, liothyronine or a mixture of thyroxine and liothyronine may be more effective than treatment with thyroxine alone. Because of the risks associated with over-treatment and/or under-treatment with thyroid hormone products, there is a need for thyroid hormone products that are consistent in potency and bioavailability. Such consistency is best accomplished by 1) maintaining consistent amounts of the thyroid hormone active moiety (e.g., T4 and/or T3) during tablet manufacture; 2) providing dosage forms that extend the release of thyroid hormones in their absorption window, e.g., within the upper GI tract; and 3) providing sustained release dosage forms that provide and maintain T4 and/or T3 plasma level within physiological range of from about 0.8 ng/ml to about 2 ng/ml over an extended period, while blunting the Cmax to mitigate or eliminate burst release of the drug, which is generally associated with side effects as seen in immediate release products.

Currently marketed immediate release liothyronine products sometimes result in undesired abrupt fluctuations in plasma levels of the drug, which may lead to adverse, short-term side effects such as increased heart rate, nervousness, anxiety, and irritability, and long-term side effects such as a decrease in bone density. Also, when administered in an immediate release form, liothyronine has a half-life of about 10 hours and, therefore, must be administered twice daily. The twice-daily administration places an added pill burden on patients and exposes the patients to twice-a-day undesired abrupt fluctuations in plasma levels of liothyronine.

A sustained release pharmaceutical composition provides many advantages over conventional immediate release pharmaceutical compositions. The advantages include less frequent dosing, increased patient compliance, a more sustained drug plasma level response, therapeutic action with less ingested drug, and fewer side effects. By providing a slow and steady release of the medicament over time by use of a sustained release composition, concentration peaks ($C_{max}$) are mitigated/blunted or even eliminated, resulting in a smoother and more sustained blood level response.

However, effective oral sustained release compositions of liothyronine must also take into consideration the narrow therapeutic absorption window of the drug. A therapeutic agent's absorption window is the area in the body where the therapeutic agent is absorbed. A pharmaceutical dosage form, under fed conditions, requires about 3-5 hours to pass through the stomach and small intestine. Liothyronine is known to exhibit a narrow therapeutic absorption window in the upper GI tract. See, WO2008/057464. Therefore, even a sustained release composition (i.e., non-gastroretentive) releasing liothyronine over a period of 8-12 hours may provide little or no absorption of liothyronine after the four-hour period, as the sustained release composition passes through the upper GI tract in about 3-5 hours. Such a sustained release composition of liothyronine would not remain within the narrow absorption window after a 5-hour post administration period, as it passes through the upper GI tract, thereby minimizing the drug's absorption and allowing for a fall in the plasma concentration of the drug to the baseline concentration. Such fall in plasma concentration of liothyronine will be further disrupted when the composition is administered without food, e.g., under fasting conditions.

Thus, it is desirable to provide sustained release pharmaceutical compositions that release liothyronine in the upper GI tract over an extended time period, e.g., from about 6 hours to about 20 hours. The present disclosure provides osmotic, floating gastroretentive compositions of liothyronine or a pharmaceutically acceptable salt thereof that provide sustained release of liothyronine, or a pharmaceutically acceptable salt thereof, in upper GI tract for at least about 4 hours, e.g., from about 6 hours to about 20 hours. The gastroretentive liothyronine compositions of the disclosure 1) maximize liothyronine absorption, 2) mitigate/blunt any burst release of liothyronine associated with undesired side effects, 3) provide blunted Cmax for reducing excursions in liothyronine plasma concentrations outside of the normal physiological range, 4) minimize fluctuations in drug release from the steady-state trough concentration ($C_{min}$) of liothyronine (baseline plasma level of subjects during treatment with liothyronine), and 5) maintain plasma level concentrations of liothyronine above the pre-administration concentration levels over an extended time period.

4. SUMMARY

In certain embodiments, the disclosure provides an osmotic, floating gastroretentive composition comprising 1) a multilayer core comprising a pull layer containing liothyronine or a pharmaceutically acceptable salt thereof, an acid, and a gas-generating agent, and a push layer; and 2) a permeable elastic membrane containing at least one orifice and covering at least a portion of the multilayer core. The permeable elastic membrane comprises a copolymer of ethyl acrylate, methyl methacrylate and trimethylammonioethyl methacrylate chloride; and a plasticizer. The at least one orifice is in fluid communication with the pull layer.

In certain embodiments, the copolymer contains ethyl acrylate, methyl methacrylate and trimethylammonioethyl methacrylate chloride in a weight ratio of about 1:2:0.2.

In certain embodiments, the copolymer contains ethyl acrylate, methyl methacrylate and trimethylammonioethyl methacrylate chloride in a weight ratio of about 1:2:0.1.

In certain embodiments, the plasticizer is selected from the group consisting of triethyl citrate, triacetin, polyethylene glycol, propylene glycol, dibutyl sebacate, and mixtures thereof.

In certain embodiments, the acid is an organic acid selected from the group consisting of succinic acid, citric acid, acetic acid, malic acid, benzoic acid, stearic acid, tartaric acid, boric acid, and mixtures thereof.

In certain embodiments, each of the pull layer and the push layer further comprises a swellable water-soluble polymer.

In certain embodiments, the swellable water-soluble polymer in the push layer is a polyethylene oxide polymer having an average molecular weight of greater than or equal to about 600,000 Da.

In certain embodiments, the polyethylene oxide polymer in the push layer has an average molecular weight of about 600,000 Da, about 900,000 Da, about 1,000,000 Da, about 2,000,000 Da, about 3,000,000 da, about 4,000,000 Da, about 5,000,000 Da, about 6,000,000 Da, about 7,000,000 Da, or intermediate values therein.

In certain embodiments, the swellable water-soluble polymer in the pull layer is selected from the group consisting of is hypromellose. Sodium carboxymethyl cellulose, carbomers, and mixtures thereof.

In certain embodiments, the swellable water-soluble polymer in the pull layer is hypromellose. In certain embodiments, hypromellose is a mixture of a low viscosity hypromellose having a viscosity, in 2% aqueous solution at 25° C., of less than or equal to 5000 cp, and a high viscosity hypromellose with a viscosity, in 2% aqueous solution at 25° C., of greater than 5,000 cp. In certain embodiments, the low viscosity hypromellose and the high viscosity hypromellose are present in a low viscosity hypromellose: high viscosity hypromellose weight ratio from 60:40 to 99.9:0.1.

In certain embodiments, the swellable water-soluble polymer in the pull layer is a low viscosity hypromellose.

In certain embodiments, the swellable water-soluble polymer in the pull layer is sodium carboxymethyl cellulose.

In certain embodiments, the composition provides sustained release, while maintaining plasma concentration of from 0.5 ng/ml to 3 ng/ml, of liothyronine or a pharmaceutically acceptable salt, for at least 4 hours.

In certain embodiments, the composition comprises from about 1 µg to about 200 µg of liothyronine or a pharmaceutically acceptable salt thereof.

In certain embodiments, the disclosure provides a method of treating hypothyroidism in a patient in need thereof, the method comprising administering to the patient, an osmotic, gastroretentive composition comprising: 1) a multilayer core comprising a pull layer containing liothyronine or a pharmaceutically acceptable salt thereof, an acid, and a gas-generating agent, and a push layer; and 2) a permeable elastic membrane containing at least one orifice and covering at least a portion of the multilayer core. The permeable elastic membrane comprises a copolymer of ethyl acrylate, methyl methacrylate and trimethylammonioethyl methacrylate chloride; and a plasticizer. The at least one orifice is in fluid communication with the pull layer. The total daily dose of liothyronine or a pharmaceutically acceptable salt thereof, provided by the composition, is from about 1 µgm to about 200 µgm.

In certain embodiments, the composition is administered once-a-day.

In certain embodiments, the composition is administered once-a-day as a single dose comprising a single dosage unit.

In certain embodiments, the composition is administered once-a-day as a single dose comprising multiple dosage units.

In certain embodiments, the disclosure provides a method of using liothyronine as replacement therapy in primary (thyroidal), secondary (pituitary), and tertiary (hypothalamic) congenital or acquired hypothyroidism, the method comprising, orally administering to a patient in need thereof, an osmotic, gastroretentive composition comprising 1) a multilayer core comprising: (i) a pull layer containing liothyronine or a pharmaceutically acceptable salt thereof, an acid, and a gas-generating agent, and a push layer; and 2) a permeable elastic membrane containing at least one orifice and covering at least a portion of the multilayer core. The permeable elastic membrane comprises a copolymer of ethyl acrylate, methyl methacrylate and trimethylammonioethyl methacrylate chloride; and a plasticizer. The at least one orifice is in fluid communication with the pull layer.

In certain embodiments, the disclosure provides a method for improving bioavailability of liothyronine in a patient in need thereof, the method comprising, orally administering to the patient, an osmotic, gastroretentive composition comprising: 1) a multilayer core comprising a pull layer containing liothyronine or a pharmaceutically acceptable salt thereof, an acid, and a gas-generating agent, and a push layer; and 2) a permeable elastic membrane containing at least one orifice and covering at least a portion of the multilayer core. The permeable elastic membrane comprises a copolymer of ethyl acrylate, methyl methacrylate and trimethylammonioethyl methacrylate chloride; and a plasticizer. The at least one orifice is in fluid communication with the pull layer.

In certain embodiments, the disclosure provides a method for making an osmotic, gastroretentive composition containing liothyronine or a pharmaceutically acceptable salt thereof, the method comprising: making pull layer blend and a push layer blend; horizontally pressing the pull layer blend and the push layer blend into a bilayered tablet core containing a pull layer and a push layer; coating the bilayered tablet core with a permeable elastic membrane; and drilling an orifice in the permeable elastic membrane. The pull layer blend comprises Drug Intermediate and an extragranular component. The Drug intermediate comprises liothyronine or a pharmaceutically acceptable salt thereof; the extragranular component comprises an acid, a gas generating agent, an osmogen, and a swellable water-soluble polymer; and the permeable elastic membrane comprises a copolymer of ethyl acrylate methyl methacrylate, and trimethylammonioethyl methacrylate chloride; and a plasticizer, and wherein the orifice is in fluid communication with the pull layer.

In certain embodiments, the Drug Intermediate blend is a dry blend.

In certain embodiments, the Drug Intermediate blend comprises liothyronine granules.

In certain embodiments, the liothyronine granules are made via wet granulation.

In certain embodiments, the liothyronine granules are made via dry granulation.

5. BRIEF DESCRIPTION OF THE DRAWINGS

FIG. 1 provides a schematic representation of the gastroretentive dosage form, according to certain embodiments, illustrating a bilayer tablet core, comprising a pull layer and a push layer, seal coat-1 surrounding the tablet core, a permeable elastic membrane surrounding seal coat-1, seal coat-2 surrounding the permeable elastic membrane, a cosmetic coat surrounding seal coat-2, and an orifice passing through seal coat-1, the permeable membrane, and seal coat-2, wherein the orifice is in fluid communication with the pull layer.

FIG. 2 compares dissolution profiles of Tablet 1 and Tablet 2, using USP Apparatus II, at 100 RPM and 37° C., in a 500 ml mixture of 0.1 N HCl and glycerol, for 24 hours. Tablet 1 contained 220 mg of POLYOX™ WSR N-60K and 25 mg of sodium chloride in the push layer and Tablet 2 contained 132 mg of POLYOX™ WSR Coagulant and 15 mg of sodium chloride in the push layer.

FIG. 3 compares dissolution profiles of Tablet 3, using USP Apparatus I at 37° C., in 500 ml of a dissolution medium containing 0.1 N HCl and 5% methanol; and in a 500 ml of a dissolution medium containing 0.1N HCl and 5% glycerol.

FIG. 4 compares volume gain of Tablet 3 and Tablet 4, in 200 ml of dissolution medium containing 0.001 N HCl and 80 mM NaCl, on floatation and additional time points.

Figure 7:
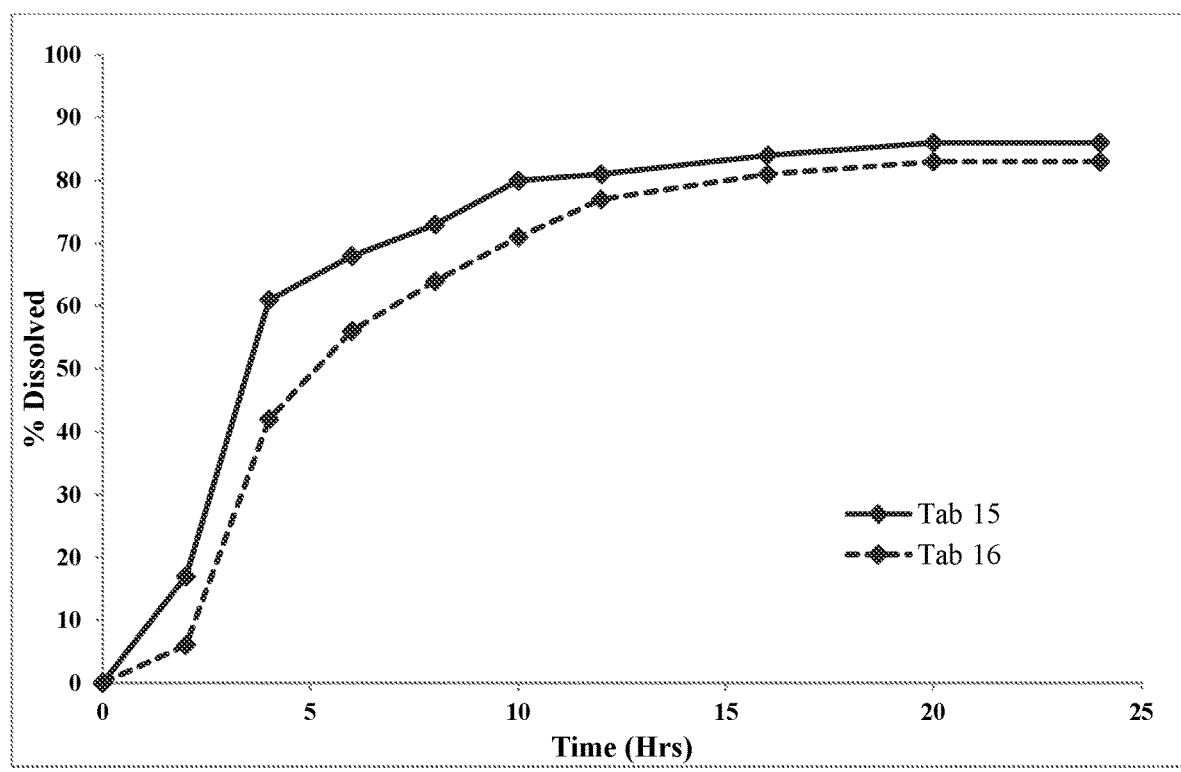

FIG. 7 compares dissolution profiles of Tablet 15 and Tablet 16, using USP Apparatus I at 37° C., in a 500 ml dissolution medium containing 0.1 N HCL and 5% glycerol.

Figure 8:
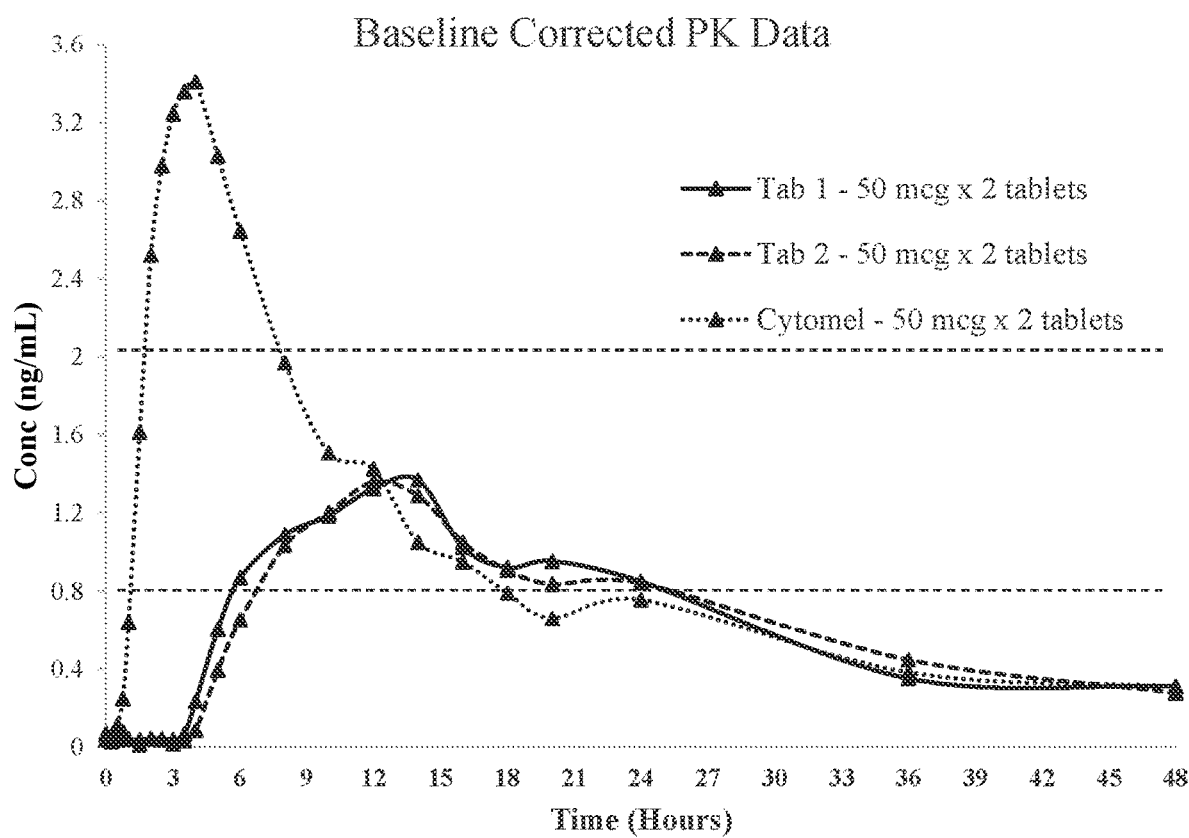

FIG. 8 compares baseline corrected PK profiles of Tablet 1 (50 mcg×2), Tablet 2 (50 mcg×2), and CYTOMEL® (50 mcg×2). FIG. 8 demonstrates that Tablet 1 and Tablet 2 provide therapeutic concentration (e.g., from about 0.8 ng/ml to about 2 ng/ml) of T3 for at least about 15 hours and provide substantially reduced burst release (about 50% reduction in Cmax) as compared to CYTOMEL®

Figure 9:
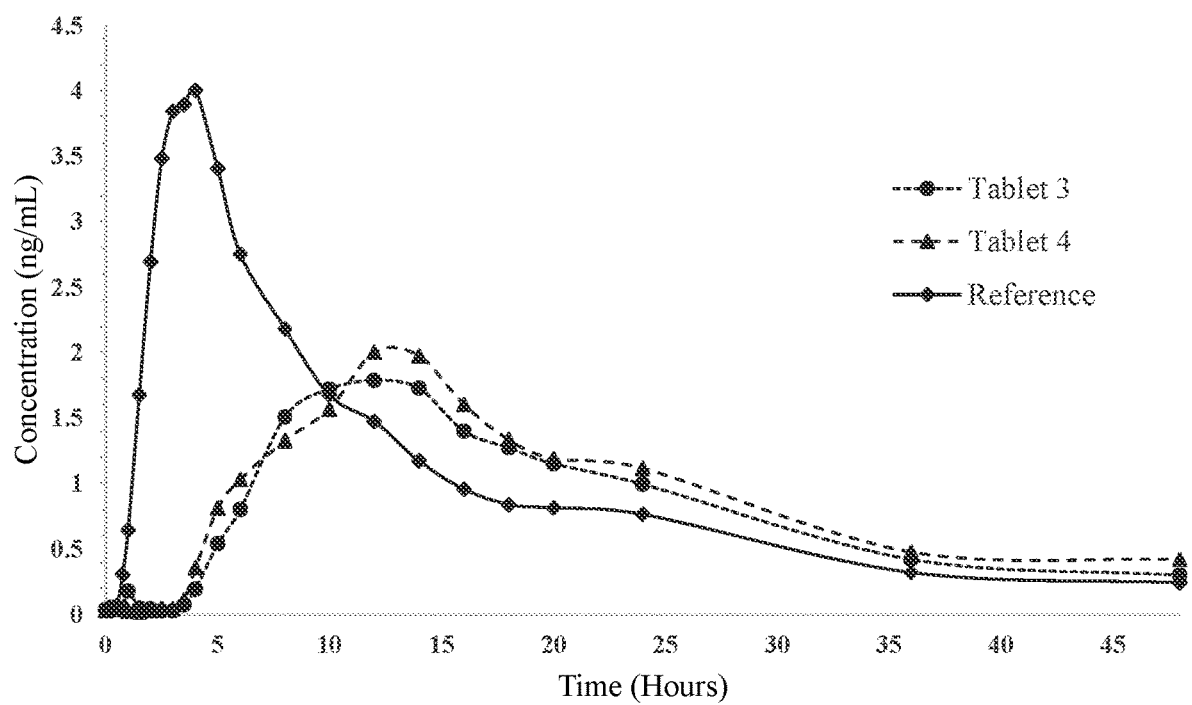

FIG. 9 compares baseline corrected PK profiles of Tablet 3 (50 mcg×2), Tablet 4 (50 mcg×2), and CYTOMEL® (50 mcg×2). FIG. 9 demonstrates that Tablet 4 provides therapeutic concentration (e.g., from about 0.8 ng/ml to about 2 ng/ml) of T3 for at least about 15 hours and provide substantially reduced burst release (about 50% reduction in Cmax) as compared to CYTOMEL®. The data further demonstrates that Tablet 4 (125 mg coating weight gain) shows faster release and improved bioavailability compared to Tablet 3 (200 mg coating weight gain).

Figure 10:
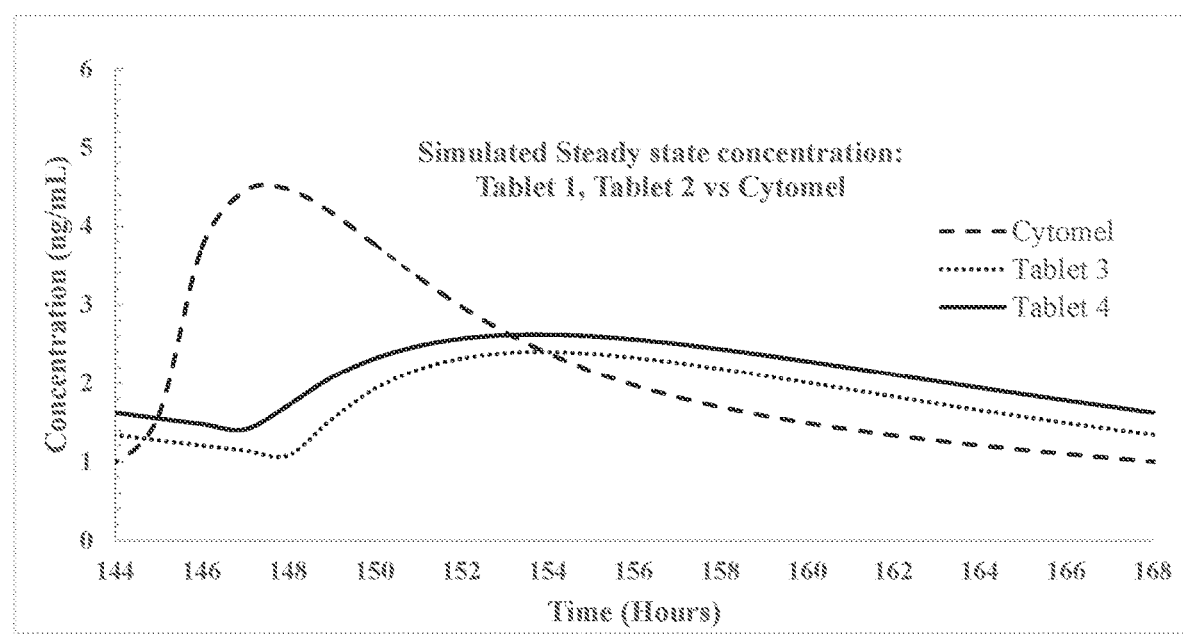

FIG. 10 provides a simulated steady state plasma concentration of T3 at day 7, with administration of Tablets 3 (50 mcg×2) and 4 (50 mcg×2) vs CYTOMEL (50 mcg×2). FIG. 10 demonstrates that Tablet 3 (50 mc gm×2) and Tablet 4 (50 mcg×2) provide T3 plasma concentration of between 0.8 ng/ml and 3 ng/ml at steady state (SS). The data further demonstrates that AUC0-∞(in vivo) for Tablets 3 and 4 are comparable to corresponding $AUC_{144-168}$ at steady state.

6. DETAILED DESCRIPTION

The present disclosure provides osmotic, floating gastroretentive liothyronine compositions (gastroretentive liothyronine compositions) with enhanced pharmacokinetic attributes. The gastroretentive liothyronine compositions of the disclosure provide extended release, with reduced burst release/blunted Cmax, and reduced peak-to-trough ratios (Cmax/Cmin) of liothyronine or a pharmaceutically acceptable salt thereof, compared to marketed immediate release liothyronine products (e.g., CYTOMEL®). The gastroretentive liothyronine compositions of the disclosure improve drug bioavailability by retaining the dosage form in the stomach for prolonged periods and extending the release of liothyronine, or a pharmaceutically acceptable salt thereof, in the stomach/upper GI tract for continuous absorption. Such prolonged gastric retention, with sustained release provided by the gastroretentive liothyronine compositions of the disclosure, improves drug bioavailability, reduces drug waste, and improves drug solubility.

The gastroretentive compositions of the disclosure provide sustained release of liothyronine, or a pharmaceutically acceptable salt thereof, in the upper GI tract to maintain therapeutic plasma concentrations of liothyronine, or a pharmaceutically acceptable salt thereof, over extended periods, while mitigating or eliminating its burst release/plasma concentration peak ($C_{max}$). Additionally, the gastroretentive compositions of the disclosure enhance stability of liothyronine, or a pharmaceutically acceptable salt thereof, by including water-soluble hydrophilic polymers that swell, while preventing or mitigating liothyronine degradation.

The gastroretentive liothyronine compositions of the disclosure, when exposed to gastric fluid or simulated gastric fluid (e.g., dissolution medium that is used to mimic gastric fluid conditions/chemical environment of gastric medium in vitro in an individual.), expand in about 120 minutes or less to a size that prevents passage through the pyloric sphincter, and remain in an expanded state for prolonged periods, e.g., from about 6 hours to about 24 hours. For clarity and not by way of limitation, this detailed description is divided into the following sub-portions:

6.1. Definitions;
   6.2. Compositions;
   6.3. Methods of Treating;
   6.4. Methods of Making; and
   6.5. Features of the Dosage Forms.

6.1. Definitions

The terms used in this specification generally have their ordinary meanings in the art, within the context of the disclosed subject matter and in the specific context where each term is used. Certain terms are discussed below, or elsewhere in the specification, to provide additional guidance to the practitioner in describing the compositions and methods of the disclosed subject matter and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein, "and/or" refers to and encompasses any and all possible combinations of one or more of the associated listed items. The term "about" or "approximately" as used herein means within an acceptable error range for the particular value as determined by one of ordinary skill in the art, which will depend in part on how the value is measured or determined, i.e., the limitations of the measurement system. The term "about" can mean a range of up to 20%, up to 19%, up to 18%, up to 17%, up to 16%, up to 15%, up to 14%, up to 13%, up to 12%, up to 11%, up to 10%, up to 9%, up to 8%, up to 7%, up to 6%, up to 5%, up to 4%, up to 3%, up to 2%, or up to 1% of a given value. Alternatively, the term "about," particularly when used with respect to biological systems or processes, can mean within an order of magnitude, or within 5-fold, or within 2-fold, of a value.

The terms "baseline concentration" and "baseline plasma level," as used interchangeably herein, for subjects capable of producing any amount of liothyronine, refer to a circulating endogenous concentration of liothyronine in the subject immediately prior to the administration of the sustained release gastroretentive liothyronine compositions of the present disclosure. Additionally, for subjects not capable of producing any amount of liothyronine, who are being treated with thyroid hormone, the terms "base line concentration" and "baseline plasma level" refer to a steady-state trough concentration ($C_{min}$) of liothyronine.

The terms "Fluctuation Index" and "FI," as used interchangeably herein with respect to the compositions of the disclosure, e.g., T3 compositions of the disclosure and marketed products, CYTOMEL®, refer to fluctuations in plasma levels of drug at Steady State/simulated Steady State. Fluctuation Index provides a quantitative measurement of fluctuation in drug plasma concentration, measured as dose related peak-trough fluctuations. Fluctuation Index is calculated using the formula: FI=(Cmax−Cmin)/Cav, wherein Cmax is the maximum plasma concentration of the drug, e.g., T3 or a pharmaceutically acceptable salt thereof; Cmin is the minimum plasma concentration of the drug; and Cav is the average plasma concentration of the drug.

The terms "steady-state," "steady-state concentration," and "steady-state-plasma concentration, as used interchangeably herein, refer to equilibrium/unchanged drug plasma concentration. In certain embodiments, the "steady-state," "steady-state concentration," and "steady-state-plasma concentration includes equilibrium/unchanged drug plasma concentration that is required to maintain therapeutic level of the drug, e.g., liothyronine or a pharmaceutically acceptable salt thereof.

The term "Cmin," as used herein, refers to lowest plasma concentration of a drug.

The term "Cmax," as used herein, refers to highest plasma concentration of a drug.

The term "Cav," as used herein, refers to average plasma concentration of a drug.

In certain embodiments, for a subject consuming liothyronine compositions, the terms "$C_{min}$" and "trough concentration," are used interchangeably, and refer to steady-state baseline plasma level of liothyronine or a pharmaceutically acceptable salt thereof, in subjects during treatment with liothyronine.

The terms "liothyronine," and "T3," as used interchangeably herein, refer to liothyronine or a pharmaceutically acceptable salt thereof.

The terms "burst release" and "dose dumping," as used interchangeably herein with respect to liothyronine compositions, refer to an uncontrolled release of T3 or a pharmaceutically acceptable salt thereof, resulting in serum T3 levels of greater than 3 ng/ml.

The term "initial burst release," as used herein, refers to an initial uncontrolled release of a large bolus of T3 (e.g., serum T3 levels of greater than 3 ng/ml) before the release rate reaches a stable profile.

The terms "osmotic, floating gastroretentive dosage form," "osmotic gastroretentive dosage form," "floating gastroretentive dosage form," and "gastroretentive dosage form," as used interchangeably herein, refer to a push-pull osmotic dosage form that swells and floats to provide gastric retention and exhibits delayed gastric emptying as compared to food (e.g., retention in the stomach beyond the retention of food).

The term "self-regulating," as used herein, refers to a gastroretentive dosage form that floats, expands, and finally shrinks to allow emptying of the dosage form from the GI tract and the patient.

The terms "osmotic dosage form" and the like, as used herein, refer to a push-pull osmotic dosage form containing a pull layer and a push layer, wherein the pull layer contains at least one pharmaceutically active agent and at least one swellable water-soluble hydrophilic polymer; and the push layer contains at least one swellable water-soluble hydrophilic polymer and at least one osmogen. In certain embodiments, the pull layer further contains at least one osmogen. The osmogens present in the dosage form help in imbibition of aqueous external fluid into the dosage form to hydrate the water-soluble hydrophilic polymer present in the pull layer and in the push layer; and to dissolve or disperse the drug/active ingredient present in the pull layer. Once the water-soluble hydrophilic polymer in the push layer is sufficiently hydrated and swollen with the imbibed aqueous external fluid, the push layer pushes the pull layer containing dissolved or dispersed drug through an orifice, out of the dosage form, thereby providing a controlled release of the drug. Further, swelling of the swellable water-soluble hydrophilic polymer in the pull layer, due to imbibition of aqueous external fluid, further controls the release of the drug present in the pull layer.

The terms "water-soluble hydrophilic polymer," "swellable water-soluble polymer," and "swellable water-soluble hydrophilic polymer," as used interchangeably herein refer hydrophilic polymers that dissolve and swell on contact with water or aqueous fluid.

The term "osmosis," as used herein, refers to movement of a solvent from a solution of low solute concentration to a solute or a solution of high solute concentration through a semipermeable or permeable membrane.

The term "osmotic agent" includes swellable water-soluble hydrophilic polymers, and osmogens comprising ionic or nonionic compounds.

The term "osmogen," as used herein, refers to osmotically active ions or molecule, e.g., ionic or nonionic compounds, that dissolves in in a solvent to create osmotic pressure buildup inside the composition/dosage form, for the passage of the solvent from a solution of low solute concentration to a solute or a solution of high solute concentration through a semipermeable or permeable membrane.

The terms "active agent," "active ingredient," "active pharmaceutical agent," "active pharmaceutical ingredient," and "drug," as used interchangeably herein, refer to a thyroid hormone or a pharmaceutically acceptable salt thereof. In certain embodiments, the term "thyroid hormone," refers to liothyronine, levothyroxine, and/or their pharmaceutically acceptable salts. In certain embodiments, thyroid hormone is liothyronine or a pharmaceutically acceptable salt thereof. In certain embodiments, thyroid hormone is a combination of liothyronine or a pharmaceutically acceptable salt thereof and levothyroxine or a pharmaceutically acceptable salt thereof.

The term "pharmaceutically acceptable," when used in connection with the pharmaceutical compositions of the disclosed subject matter, refers to molecular entities and compositions that are physiologically tolerable and do not typically produce untoward reactions when administered to a human. As used herein, the term "pharmaceutically acceptable" can also refer to being approved by a regulatory agency of the federal government or a state government or listed in the U.S. Pharmacopeia, National Formulary and Drug Standard Laboratory (NF), or other generally recognized pharmacopeia for use in animals, and more particularly in humans.

The terms "prophylactically effective amount" and "therapeutically effective amount," as used interchangeably herein, refer to an amount of a compound/active agent sufficient to mitigate, prevent or cure a disease or condition or one or more symptoms associated with the disease or condition, or prevent recurrence of the disease or condition.

The term "bioavailability," as used herein, refers to the fraction of an administered drug that reaches the systemic circulation, as measured through various pharmacokinetic (PK) metrics such as $C_{min}$, $C_{max}$, $T_{max}$, $AUC_{0-t}$, and $AUC_{0-inf}$.

The terms "dosage form," "formulation," "composition," and "pharmaceutical composition," as used interchangeably herein, refer to pharmaceutical drug products in the form in which they are marketed for use, with specific mixtures of active pharmaceutical ingredients and inactive excipients, in a particular configuration, e.g., tablets, capsules, particles, and apportioned into a particular dose.

The term "gastric fluid," as used herein, refers to medium occurring in the stomach of an individual.

The terms "dissolution medium," "medium simulating gastric conditions," and "simulated gastric fluid," as used interchangeably herein, refer to a medium of dissolution that is used to mimic gastric fluid conditions/chemical environment of gastric medium in vitro in an individual.

In certain embodiments, the "dissolution medium" comprises a medium with pH of from about 1 to about 7. In certain embodiments, the dissolution medium comprises pH 4.5 acetate buffer, pH 5 buffer, pH 6.8 acetate buffer, 0.1 N HCl, 0.01 N HCl, or 0.001 N HCl. In certain embodiments, the dissolution medium further comprises from 0 mM to about 200 mM of NaCl. In certain embodiments, the dissolution medium further comprises monohydric, dihydric, and/or trihydric alcohols, e.g., methanol, ethanol, glycerol, e.g., 5% glycerol, 5% methanol. The term "light meal medium," as used herein refers to aqueous media simulating light meal conditions. In certain embodiments, "light meal media" is an aqueous medium comprising sodium chloride, potassium chloride, potassium hydrogen phosphate, calcium chloride, citric acid, and sugar.

The term "gas generating agent," as used herein refers to carbonate and/or bicarbonate salts of alkali and/or alkaline earth metals, that can interact with acid for in situ gas generation. The gas-generating agent generates $CO_2$ with imbibition of fluid into the dosage form.

The terms "acid," and "organic acid," as used interchangeably, refer to compounds that, on imbibition of fluid, e.g., aqueous external fluid, into the dosage form, react with the gas generating agent and generates CO2.

The term "floating" or the like, and as used herein in conjunction with a "floating gastroretentive dosage form" or the like, refers to a dosage form that has a bulk density less than gastric fluid and simulated gastric fluid (SGF). Such dosage forms are "floating" in that they remain buoyant in the gastric fluids of the stomach or SGF for a targeted period of time.

The term "degradable," as used herein, refers to capable of being chemically and/or physically modified, dissolved, or broken down, under in vivo or in vitro conditions, within a relevant time period.

The term "prolonged period" or the like, as used herein, refers to a period that lasts for about 6 hours or more, e.g., from about 8 hours to about 24 hours. A prolonged period includes 6, 7, 8, 9, 10, 11, 12, 13, 14, or more hours. In certain embodiments, a prolonged period can include up to 24 hours.

The terms "swellable" and "swelling," as used interchangeably herein with respect to a polymer, refer to a polymer that swells by imbibing fluid and/or entrapping $CO_2$.

The terms "expanding" and "expansion," as used interchangeably herein with respect the membrane, refer to stretching, distention or expansion of the membrane due to an outward pressure (e.g., gas pressure, or pressure due to swelling of a polymer in the core) on the membrane.

The terms "expanding" and "expansion," as used interchangeably herein with respect to a gastroretentive dosage form, refer to expansion of the dosage form due to generation of gas and/or swelling of the core (e.g., gas pressure, or due to swelling of a polymer in the core). The term "rapidly expanding" as used herein with respect to the gastroretentive dosage form of the disclosure, refers to at least 50% volume gain of the dosage form, from its initial volume, in about 120 minutes or less.

The terms "shear" and "shear effect," as used interchangeably herein, refer to peristaltic waves moving from the midcorpus of the stomach to the pylorus, particularly in a fed state.

The terms "pore former" and the like, as used herein, refer to water-soluble polymers and/or water-soluble small molecules that will form pores or channels (i.e., behave as a channeling agent) in the functional coat/membrane, thereby increasing the permeability of the membrane. The term "permeable membrane," as used herein, refers to a polymeric membrane or a film that is substantially permeable to the passage of dissolved and/or undissolved solutes, e.g., excipients and small molecule active pharmaceutical agents/drugs, e.g., liothyronine or a pharmaceutically acceptable salt thereof, and passage of fluids/solvents. In certain embodiments, the permeable membrane is substantially permeable to liothyronine or a pharmaceutically acceptable salt thereof, and one or more excipients, present in dissolved or undissolved state. In certain embodiments, the permeable membrane is substantially permeable to one or more excipients and small molecule drugs that are present in a substantially dissolved or undissolved state in a solvent/fluid. In certain embodiments, the permeable membrane is substantially permeable to a small molecule drug, e.g., molecular weight of less than 900 Da, present in dissolved or undissolved state. The permeable membrane comprises permeable polymers, e.g., copolymers of ethyl acrylate, methyl methacrylate, and trimethylammonioethyl methacrylate chloride, with or without pore formers.

The term "small molecule drug" refers to a drug with molecular weight of less than 900 Da. In certain embodiments, the term "small molecule" refers to a molecule with particle size of less than or equal to 1 nm.

The term "semipermeable membrane," as used herein, refers to a polymeric membrane or a film that is substantially impermeable to the passage of solutes, including dissolved or undissolved drug and other excipients/ingredients and substantially permeable to passage of fluids/solvents. In certain embodiments, the semipermeable membrane is substantially impermeable to drugs/active pharmaceutical agents that are present in a substantially dissolved or undissolved state in a solvent/fluid. The semipermeable membrane comprises semipermeable polymers, e.g., cellulose acetate, cellulose ethers, cellulose esters, cellulose ester-ethers, polyacrylic acids and esters, polymethacrylic acids and esters, and cellulosic esters and polyethylene glycols.

The term "substantially free," as used herein, refers to excluding any functional (e.g., noncontaminating) amount, which refers to any amount that contributes/influences on therapeutic efficacy/effect of the composition, e.g., any functional amount of excipients and/or active agent that effects on stability of the active agent/T3, release profile of the composition, and/or gastroretentive attributes of the composition.

The terms "glass Transition Temperature" and "Tg," as used interchangeably herein, refers to gradual and reversible transition in amorphous materials/polymers (or in amorphous regions within semicrystalline materials) from a hard and relatively brittle "glassy" state into a viscous or rubbery state as the temperature is increased. An amorphous solid that exhibits a glass transition is called a glass. The glass-transition temperature Tg of a material characterizes the range of temperatures over which this glass transition occurs. It is always lower than the melting temperature, Tm, of the crystalline state of the material, if one exists. At the Tg, the amorphous regions experience transition from rigid state to more flexible state with higher free volume (increased gap between molecular chains). Polymers with flexible backbone show lower Tg, whereas polymers whose molecular structure is stiff, rigid, and inflexible show a higher Tg. Glass transition temperature helps determine various flexible and rigid applications for a material.

The terms "orifice," "delivery orifice," and "hole," as used interchangeably herein, include, but are not limited to, at least one opening/exit means in the coating of the osmotic gastroretentive composition to provide fluid communication with the pull layer. In certain embodiments, the terms "orifice," "delivery orifice," and "hole," as used interchangeably herein, include, but are not limited to, one opening/exit means in the coating of the osmotic gastroretentive composition to provide fluid communication with the pull layer. In certain embodiments, the terms "orifice," "delivery orifice," and "hole," as used interchangeably herein, include, but are not limited to, two or more openings/exit means in the coating of the osmotic gastroretentive composition to provide fluid communication with the pull layer. The opening (basically a delivery port) can be formed via manual, mechanical, or laser drilling of the coatings, often into the side facing the pull layer. In certain embodiments, there is an in situ formation of the delivery orifice with incorporation of water-soluble pore-forming agents into the coating. The pore-forming agents, upon contact with aqueous environment, dissolve and leach out from the membrane, creating an orifice.

The term "wicking agent," as used herein, refers to a material with the ability to draw/spread water into the gastroretentive dosage form. The wicking agents, with their ability to undergo physisorption of water, help to increase the contact surface area of the drug with incoming aqueous fluid.

The term "physisorption," as used herein, refers to absorption in which solvent molecules loosely adhere to surface of the wicking agent via Van der Waals interactions between the surface of the wicking agent and the adsorbed solvent molecule.

The term "patient," as used herein, refers to a human or nonhuman mammal that may need to receive an osmotic, floating gastroretentive dosage form of the present disclosure.

The terms "treating" and "treatment," as used interchangeably herein, refer to obtaining a desired pharmacological and physiological effect. The effect can be prophylactic in terms of preventing or partially preventing a disease, symptom, or pathological condition and/or can be therapeutic in terms of a partial or complete alleviation or cure of a disease, condition, symptom, or adverse effect attributed to a pathological condition. Thus, "treatment" (and the like) covers any treatment of a disease in a mammal, particularly in a human, and includes, but is not limited to: (a) preventing a pathological condition from occurring in an individual who may be predisposed to develop the condition but, e.g., has not yet been diagnosed as having such condition (e.g., causing the clinical symptoms of such condition not to develop); (b) inhibiting, arresting, or reducing the development of the pathological condition or its clinical symptoms; and (c) relieving symptoms associated with the pathological condition.

The term "upper GI tract," as used herein, refers to the stomach, and proximal parts of the small intestine, e.g., the duodenum and jejunum.

The term "lower GI tract," as used herein, refers to distal parts of the small intestine, e.g., the ileum, and all of the large intestine, including the colon, cecum, and rectum.

The term "floating" or the like, and as used herein in conjunction with a "gastroretentive dosage form" or the like, refers to a dosage form that has a bulk density less than gastric fluid and/or simulated gastric fluid (SGF). Such dosage forms are "floating" in that they remain buoyant in the gastric fluids of the stomach and/or SGF for a targeted time period.

The term "floating lag time," as used herein, includes the time between the addition of a dosage form to a medium and the time when the dosage form begins to float on the surface of the medium (e.g., in an in vitro setting), or the time between the consumption of a dosage form by a user and the time when the dosage form begins to float on the surface of the gastric fluid (e.g., in an in vivo setting).

The term "dissolution lag time," as used herein, refers to the time between the addition of a dosage form to a medium and the time when the active agent begins to dissolve in the medium. The term "medium," as used herein, refers to a dissolution medium in an in vitro setting and gastric fluid in an in vivo setting.

The term "viscosity gradient," as used herein, refers to a difference in viscosity between adjacent layers of multilayered gastroretentive dosage forms of the disclosure. The term "decreasing viscosity gradient," as used herein, refers to a decrease in viscosity from the push layer to the pull layer, wherein the push layer and the pull layer are adjacent to each other.

The terms "extended release," "controlled release," "sustained," and "modified release," as used interchangeably herein, refer to modified release dosage forms or compositions that are formulated to maintain targeted concentration of the administered drug, over an extended period after administration, as compared to a drug presented as an immediate release dosage form. Such compositions mitigate or eliminate burst release, and blunt/mitigate the Cmax, compared to immediate release pharmaceutical compositions of the same drug.

The phrase "optimal plasma level concentration," as used herein, refers to plasma level concentration of T3 or a pharmaceutically acceptable salt thereof, wherein the subject no longer suffers from hypothyroidism, hyperthyroidism, any symptoms associated with hypothyroidism, and any symptoms associated with hyperthyroidism. The optimal plasma level concentration will vary by subject and will depend, in large part, on the age, height, weight, metabolism, and sex of the subject. In general, however, when testing for or monitoring hypothyroidism, a TSH range between 0.5 to 5.0 uIU/ml is likely to indicate optimal plasma level concentrations of liothyronine.

6.2. Compositions

The present disclosure provides sustained release gastroretentive pharmaceutical compositions that include a thyroid hormone, such as liothyronine or a pharmaceutically acceptable salt thereof. Liothyronine is the synthetic form of a natural hormone. The preferred form of liothyronine is liothyronine salt, e.g., liothyronine sodium. In particular, the present disclosure provides osmotic, floating gastroretentive compositions of liothyronine sodium [T3 compositions], suitable for once- or twice-daily administration. The compositions provide sustained release with enhanced PK attributes of liothyronine, e.g., reduced burst release, blunted Cmax, reduced fluctuation index (≤1), reduced peak-to-trough ratios ($C_{max}/C_{min}$), and sustained release in the therapeutic range, compared to marketed immediate release liothyronine products.

The gastroretentive compositions of the disclosure enhance absorption of liothyronine by extending liothyronine release in its narrow absorption window. In certain embodiments, the gastroretentive liothyronine compositions of the disclosure provide desired pharmacokinetic (PK) profiles by releasing T3, within the absorption window of T3, in an amount that can provide and maintain/sustain therapeutic plasma concentrations for at least about 6 hours, e.g., from about 6 hours to about 24 hours. In certain embodiments, the gastroretentive liothyronine compositions of the disclosure release liothyronine, or a pharmaceutically acceptable salt thereof, e.g., T3, in the upper GI tract over an extended period, such that liothyronine can be absorbed before transit of the composition to the lower GI tract. In certain embodiments, the gastroretentive liothyronine compositions of the disclosure release T3, within any portion of the upper GI tract, e.g., the stomach, the duodenum, and the jejunum.

The gastroretentive liothyronine compositions of the disclosure release at least about 60% w/w of liothyronine, or a pharmaceutically acceptable salt thereof, based on the total weight of liothyronine or a salt thereof present in the dosage form, over an extended period. In certain embodiments, the gastroretentive liothyronine compositions of the disclosure can release about 60% w/w, about 65% w/w, about 70% w/w, about 75% w/w, about 80% w/w, about 85% w/w, about 90% w/w, about 95% w/w, about 99% w/w, or any intermediate values therein, of liothyronine, or a pharmaceutically acceptable salt thereof, over an extended period, e.g., 24 hour dosing period. In certain embodiments, the gastroretentive liothyronine compositions of the disclosure release at least about 60% w/w of liothyronine, or a pharmaceutically acceptable salt thereof, over a period of about 8 hours, about 9 hours, about 10 hours, about 11 hours, about 12 hours, about 13 hours, about 14 hours, about 15 hours, about 16 hours, about 17 hours, about 18 hours, about 19 hours, about 20 ours, about 21 hours, about 22 hours, about 23 hours, about 24 hours, or any intermediate period therein.

In certain embodiments, the gastroretentive liothyronine compositions of the disclosure provide sustained release, with reduced burst release/blunted $C_{max}$, of liothyronine or a pharmaceutically acceptable salt thereof, such that the $C_{max}$ of liothyronine is at least about 10% less than the Cmax of marketed immediate release liothyronine product (e.g., CYTOMEL®). In certain embodiments, the gastroretentive liothyronine compositions of the disclosure provide sustained release, with reduced burst release/blunted $C_{max}$, of liothyronine or a pharmaceutically acceptable salt thereof, such that the $C_{max}$ of liothyronine is at least about 20% less, at least about 25% less, at least about 30% less, at least about 35% less, at least about 40% less, at least about 45% less, at least about 50% less, at least about 55% less, at least about 60% less, at least about 70% less, or any intermediate values therein, than the $C_{max}$ of marketed immediate release liothyronine product (e.g., CYTOMEL®).

In certain embodiments, the gastroretentive liothyronine compositions of the disclosure provide sustained release, with reduced burst release/blunted Cmax, of liothyronine, or a pharmaceutically acceptable salt thereof, such that the $C_{max}$ of liothyronine is from about 0.5 ng/ml to about 5 ng/ml, from about 0.7 to 4 ng/ml, from about 0.8 to about 3 ng/ml, or any intermediate values therein. In certain embodiments, the gastroretentive liothyronine compositions of the disclosure provide a $C_{max}$ of less than about 5 ng/ml, less than about 4.9 ng/ml, less than about 4.8 ng/ml, less than about 4.7 ng/ml, less than about 4.6 ng/ml, less than about 4.5 ng·ml, less than about 4.4 ng/ml, less than about 4.3 ng/ml, less than about 4.2 ng/ml, less than about 4.1 ng/ml, less than about 4 ng/ml, less than about 3.9 ng/ml, less than about 3.8 ng/ml, less than about 3.7 ng/ml, less than about 3.6 ng/ml, less than about 3.5 ng/ml, less than about 3.4 ng/ml, less than about 3.3 ng/ml, less than about 3.2 ng/ml, less than 3.1 ng/ml, less than about 2 ng/ml, or any intermediate values therein. In certain embodiments, the $C_{max}$ refers to maximum plasma concentration at a single dose administration. In certain embodiments, the $C_{max}$ refers to max plasma concentration at multiple dose administrations. In certain embodiments, the $C_{max}$ refers to max plasma concentration at steady state. In certain embodiments, the compositions of the disclosure provide sustained release, with reduced burst release/blunted $C_{max}$, of liothyronine, or a pharmaceutically acceptable salt thereof, for at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, or any intermediate periods therein. In certain embodiments, the gastroretentive liothyronine compositions of the disclosure provide sustained release, with reduced burst release/blunted $C_{max}$, of liothyronine, or a pharmaceutically acceptable salt thereof, such that the $C_{max}$ of liothyronine is from about 0.5 ng/ml to about 4 ng/ml, from about 0.5 ng/ml to about 3.9 ng/ml, from about 0.5 ng/ml to about 3.8 ng/ml, from about 0.5 ng/ml to about 3.7 ng/ml, from about 0.5 ng/ml to about 3.6 ng/ml, from about 0.5 ng/ml to about 3.5 ng/ml, from about 0.5 ng/ml to about 3.4 ng/ml, from about 0.5 ng/ml to about 3.3 ng/ml, from about 0.5 ng/ml to about 3.2 ng/ml, from about 0.5 ng/ml to about 3.1 ng/ml, from about 0.5 ng/ml to about 3 ng/ml, from about 0.5 ng/ml to about 2.9 ng/ml, from about 0.5 ng/ml to about 2.8 ng/ml, from about 0.5 ng/ml to about 2.7 ng/ml, from about 0.5 ng/ml to about 2.6 ng/ml, from about 0.5 ng/ml to about 2.5 ng/ml, from about 0.5 ng/ml to about 2.4 ng/ml, from about 0.5 ng/ml to about 2.3 ng/ml, from about 0.5 ng/ml to about 2.2 ng/ml, from about 0.5 ng/ml to about 2.1 ng/ml, from about 0.5 ng/ml to about 2 ng/ml, or any intermediate values therein.

In certain embodiments, the gastroretentive liothyronine compositions of the disclosure, within about four hours of administration of the composition, provide plasma concentrations of liothyronine or a pharmaceutically acceptable salt thereof that does not exceed the baseline concentration (endogenous concentration or steady-state trough concentration) of liothyronine by more than about 4-fold. In certain embodiments, within about one hour of administration of the composition, the concentration of liothyronine does not exceed the baseline concentration of liothyronine by more than 3.5 times, more than 3.4 times, more than 3.3 times, more than 3.2 times, more than 3.1 times, more than 3 times, more than 2.9 times, more than 2.8 times, more than 2.7 times, more than 2.6 times, more than 2.5 times, more than 2.4 times, more than 2.3 times, more than 2.2 times, more than 2.1 times, more than 2 times, more than 1.9 times, more than 1.8 times, more than 1.7 times, more than 1.6 times, more than 1.5 times, more than 1.4 times, more than 1.3 times, more than 1.2 times, more than 1.1 times, or more than 1 times that of the baseline concentration.

In certain embodiments, the gastroretentive liothyronine compositions of the disclosure provide reduced fluctuations in liothyronine plasma concentrations, from the baseline liothyronine levels, during the dosing period, as compared to marketed immediate release liothyronine products. In most subjects, the optimal plasma concentration of liothyronine or a pharmaceutically acceptable salt thereof is 80-200 ng/dL (0.8-2.0 ng/ml). In certain embodiments, the gastroretentive compositions of the present disclosure prevent or reduce plasma concentration fluctuations that exceed 80%, 75%, 70%, 65%, 60%, 55%, 50%, 45%, 40%, 35%, 30%, 25%, 20%, 15%, 10%, 5%, 4%, 3%, 2%, 1%, 0.5%, or any intermediate values therein, of the optimal plasma concentration of liothyronine. In certain embodiments, the optimal plasma concentration is between about 0.1 ng/ml and about 3.0 ng/ml, between about 0.2 ng/ml and about 2.9 ng/ml, between about 0.2 ng/ml and about 2.8 ng/ml, between about 0.2 ng/ml and about 2.7 ng/ml, between about 0.2 ng/ml and about 2.6 ng/ml, between about 0.2 ng/ml and about 2.5 ng/ml, between about 0.2 ng/ml and about 2.4 ng/ml, between about 0.2 ng/ml and about 2.3 ng/ml, between about 0.2 ng/ml and about 2.2 ng/ml, or between about 0.2 ng/ml and about 2.0 ng/ml. In certain embodiments, Fluctuation Index of liothyronine compositions of the disclosure, at single dose and at steady state (SS), is less than the corresponding Fluctuation index of marketed immediate release liothyronine product, e.g., CYTOMEL.® In certain embodiments, Fluctuation Index of liothyronine compositions of the disclosure, at single dose administration, is less than the corresponding Fluctuation index of marketed immediate release liothyronine product, e.g., CYTOMEL.® In certain embodiments, SS Fluctuation Index for liothyronine compositions of the disclosure, is less than the corresponding SS Fluctuation index of marketed immediate release liothyronine product, e.g., CYTOMEL.® In certain embodiments, SS Fluctuation Index for liothyronine compositions of the disclosure, is less than or equal to 1.

In certain embodiments, the gastroretentive liothyronine compositions of the disclosure delay the $C_{max}$ of liothyronine or a pharmaceutically acceptable salt thereof, as compared to currently marketed products suitable for once-daily administration (e.g., CYTOMEL®), while providing a therapeutically effective amount of liothyronine for an extended period. In certain embodiments, the gastroretentive liothyronine compositions of the disclosure provide a $C_{max}$ of liothyronine or a pharmaceutically acceptable salt thereof at about 1, 2, 3, 4, 5, 6, 7, 8, 9, 10, 11, 12, 13, 14, 15, 16, 17, 18, 19, 20, 21, or 22 hours or more post-administration. In certain embodiments, the gastroretentive liothyronine compositions of the disclosure prolong $T_{max}$ of liothyronine ($T_{max}$ being the time at which $C_{max}$ is achieved). In certain embodiments, the $T_{max}$ of liothyronine is greater than one-hour post-administration. In certain embodiments, the $T_{max}$ is greater than 1, 2, 3, 4, 5, 6, 7, 8, 9, 10, 11, 12, 13, 14, 15, 16, 17, 18, 19, 20, 21, or 22-hours post-administration. In certain embodiments, the $T_{max}$ of liothyronine or a pharmaceutically acceptable salt thereof occurs from about 4 to about 18 hours post-administration of the gastroretentive liothyronine compositions of the disclosure. In certain embodiments, the $T_{max}$ of liothyronine or a pharmaceutically acceptable salt thereof is from about 6 hours to about 16 hours, from about 8 hours to about 14 hours, from about 10 hours to about 12 hours, post-administration of the gastroretentive liothyronine compositions of the disclosure.

In certain embodiments, the gastroretentive liothyronine compositions of the disclosure provide the similar AUC (i.e., the area under the plasma curve), lower $C_{max}$, and/or delayed $T_{max}$, as compared to marketed immediate release liothyronine products. In certain embodiments, the gastroretentive liothyronine compositions of the disclosure provide different AUC, lower $C_{max}$, and/or delayed $T_{max}$, as compared to marketed immediate release liothyronine products.

In certain embodiments, the gastroretentive liothyronine compositions of the disclosure reduce the dosing frequency and reduce and/or eliminate the occurrence of undesirable side effects. In certain embodiments, the undesirable side effects include adverse cardiac effects comprising, but not limited to, fluctuations in heart rate, fast or irregular heartbeat, heart palpitations, increased blood pressure, increased risk of heart attack, chest pain, and congestive heart failure. In certain embodiments, the undesirable side effects may include headaches, skin rashes or hives, confusion, mood swings, irritability, muscle weakness, psychosis, restlessness, nervousness, sweating, sensitivity to heat, anxiousness, excessive sweating, flushing, shortness of breath, osteoporosis, and deceased bone density.

In certain embodiments, the gastroretentive liothyronine compositions of the disclosure, upon administration, reduce undesirable side effects by at least about 5%, as compared to currently marketed immediate release liothyronine products (e.g., CYTOMEL®). In certain embodiments, undesirable side effects are reduced by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or any intermediate values therein, as compared to marketed immediate release liothyronine products.

In certain embodiments, the gastroretentive liothyronine compositions of the present disclosure provide therapeutically effective amount of liothyronine, or a pharmaceutically acceptable salt thereof, for a period of from about 6 hours to about 24 hours. In certain embodiments, the gastroretentive liothyronine compositions of the disclosure provide a therapeutically effective amount of liothyronine, or a pharmaceutically acceptable salt thereof, for a period of from about 6 hours to about 24 hours, from about 8 hours to about 20 hours, or from about 10 to about 16 hours. In certain embodiments the gastroretentive liothyronine compositions of the disclosure provide a therapeutically effective amount of liothyronine, or a pharmaceutically acceptable salt thereof, for a period of about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or any intermediate periods therein. In certain embodiments, the gastroretentive liothyronine compositions of the disclosure provide a therapeutically effective amount of liothyronine, or a pharmaceutically acceptable salt thereof, for a period of at least 6 hours, at least 8 hours, at least 10 hours, at least 12 hours, at least 16 hours, at least 18 hours, at least 20 hours, or at least 24 hours.

In certain embodiments, the release of liothyronine can follow zero-order or first-order kinetics. In certain embodiments, the gastroretentive liothyronine compositions of the disclosure contain about 0.0001% w/w to about 1% w/w of liothyronine or pharmaceutically acceptable salt thereof, based on the total weight of the composition. In certain embodiments, the gastroretentive liothyronine compositions of the disclosure contain about 0.001% w/w to about 0.1% w/w, about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, or any intermediate values therein, of liothyronine or pharmaceutically acceptable salt thereof, based on the total weight of the composition. In certain embodiments, the gastroretentive liothyronine compositions of the disclosure contain any therapeutically effective amount of liothyronine or pharmaceutically acceptable salt thereof, such as from about 0.001 µg to about 200 µg, from about 0.01 µg to about 100 µg, or from about 0.1 µg to about 50 µg. In certain embodiments, the gastroretentive liothyronine composition of the disclosure contain from about 1 µg to about 100 µg, e.g., about 5 µg, about 6 µg, about 7 µg, about 8 µg, about 9 µg, about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 65 µg, about 70 µg, about 75 µg, about 80 µg, about 85 µg, about 90 µg, about 95 µg, about 100 µg, about 105 µg, about 110 µg, or any intermediate values therein, of liothyronine or pharmaceutically acceptable salt thereof. In certain embodiments, the gastroretentive liothyronine compositions comprise oral, osmotic, floating gastroretentive compositions that on contact with gastric fluid exhibit at least 100% volume gain, measured from its original volume at the time of contact with gastric fluid, in about 6 hours or less, e.g., about 180 mins, about 170 mins, about 160 mins, about 150 mins, about 140 mins, about 130 mins, about 120 mins, about 115 mins, about 110 mins, about 105 mins, about 100 mins, about 95 mins, about 90 mins, about 85 mins, about 80 mins, about 75 mins, about 70 mins, about 65 mins, about 60 mins, about 55 mins, about 50 mins, about 45 mins, about 40 mins, about 35 mins, about 30 minutes, or any intermediate periods. In certain embodiments, the gastroretentive liothyronine compositions comprise oral, osmotic, floating gastroretentive compositions that on contact with simulated gastric fluid exhibit at least 100% volume gain, measured from its original volume at the time of contact with the simulated gastric fluid, in about 3 hours or less, e.g., about 180 mins, about 170 mins, about 160 mins, about 150 mins, about 140 mins, about 130 mins, about 120 mins, about 115 mins, about 110 mins, about 105 mins, about 100 mins, about 95 mins, about 90 mins, about 85 mins, about 80 mins, about 75 mins, about 70 mins, about 65 mins, about 60 mins, about 55 mins, about 50 mins, about 45 mins, about 40 mins, about 35 mins, about 30 minutes, or any intermediate periods therein. In certain embodiments, the gastroretentive liothyronine compositions of the disclosure, when in contact with gastric fluid, float in about 3 hours or less, e.g., about 180 mins, about 170 mins, about 160 mins, about 150 mins, about 140 mins, about 130 mins, about 120 mins, about 115 mins, about 110 mins, about 105 mins, about 100 mins, about 95 mins, about 90 mins, about 85 mins, about 80 mins, about 75 mins, about 70 mins, about 65 mins, about 60 mins, about 55 mins, about 50 mins, about 45 mins, about 40 mins, about 35 mins, about 30 minutes, or any intermediate periods therein, measured from the time of contact with the gastric fluid. In certain embodiments, the gastroretentive liothyronine compositions of the disclosure, when in contact with simulated gastric fluid, fluid, float in about 3 hours or less, e.g., about 180 mins, about 170 mins, about 160 mins, about 150 mins, about 140 mins, about 130 mins, about 120 mins, about 115 mins, about 110 mins, about 105 mins, about 100 mins, about 95 mins, about 90 mins, about 85 mins, about 80 mins, about 75 mins, about 70 mins, about 65 mins, about 60 mins, about 55 mins, about 50 mins, about 45 mins, about 40 mins, about 35 mins, about 30 minutes, or any intermediate periods therein, measured from the time of contact with the simulated gastric fluid. In certain embodiments, the simulated gastric fluid can comprise pH 4.5 acetate buffer; pH 6.8 acetate buffer; 0.01 N HCl; 0.001 N HCl; 0.01 N HCl containing from 0 mM to about 200 mM of NaCl; or 0.001 N HCl containing from about 0 mM to about 100 mM NaCl. In certain embodiments, simulated gastric fluid can comprise aqueous fluid with pH of from about 1 to about 7 and containing from 0 mM to about 200 mM of NaCl.

In certain embodiments, the gastroretentive compositions of the disclosure exhibit at least 100% volume gain, measured from its original volume at the time of contact with gastric fluid; provide a floating lag time of about 180 minutes or less; provide a duration of floating of at least about 6 hours, e.g., from about 6 hours to about 20 hours; and provide an extended release of liothyronine or a pharmaceutically acceptable salt thereof for at least about 6 hours, e.g., from about 6 hours to about 20 hours. In certain embodiments, the gastroretentive compositions of the disclosure exhibit at least 100% volume gain, measured from its original volume at the time of contact with simulated gastric fluid; provide a floating lag time of about 180 minutes or less; provide a duration of floating of at least about 6 hours, e.g., from about 6 hours to about 20 hours; and provide an extended release of liothyronine or a pharmaceutically acceptable salt thereof for at least about 6 hours, e.g., from about 6 hours to about 20 hours. The gastroretentive liothyronine compositions of the disclosure improve bioavailability of liothyronine or a pharmaceutically acceptable salt thereof by retaining the dosage form in the stomach for a prolonged period, e.g., from about 6 hours to about 24 hours, and extending the release of liothyronine in the stomach/upper GI tract. Such prolonged gastric retention, with extended release provided by the gastroretentive liothyronine compositions of the disclosure, improves drug bioavailability, reduces drug waste, and improves drug solubility. The osmotic, gastroretentive compositions of the disclosure include: i) a multilayered tablet core comprising a pull layer and a push layer; and ii) a permeable elastic membrane surrounding the core, wherein the membrane comprises a plasticizer and at least one copolymer of ethyl acrylate, methyl methacrylate, and trimethyl aminoethyl methacrylate chloride. The osmotic, gastroretentive liothyronine compositions of the disclosure rely on size and buoyancy of the dosage form to retain the dosage form in the stomach for an extended period of time. The compositions of the disclosure comprise pull-push osmotic dosage forms providing at least about 6 hours, e.g., from about 6 hours to about 24 hours, of gastric retention and therapeutic plasma concentration of liothyronine for the same period of time.

In certain embodiments, the pull-push osmotic, floating gastroretentive liothyronine compositions of the disclosure, which continue to swell and eventually collapse for emptying from the stomach, comprise: (i) a multilayered tablet core comprising (a) a pull layer comprising liothyronine, a gas-generating agent, and at least one swellable water-soluble hydrophilic polymer; and (b) a push layer comprising at least one swellable water-soluble hydrophilic polymer having an average molecular weight of greater than about 900,000 Da, and at least one osmogen; and (ii) a permeable elastic membrane, containing an orifice/hole in fluid communication with the pull layer, covering at least a portion of the multilayer tablet core, and comprising a plasticizer and a permeable copolymer of ethyl acrylate, methyl methacrylate, and trimethylammonioethyl methacrylate chloride. In certain embodiments, the multilayered tablet core is a bilayered tablet core.

In certain embodiments, the osmotic, floating gastroretentive liothyronine compositions of the disclosure provide sustained delivery of liothyronine in the GI tract due to the presence of a swellable water-soluble hydrophilic polymer comprising polyethylene oxide with an average molecular weight of greater than about 900,000 Da, e.g., POLYOX™ 60 (MW~2M) in the push layer. Such polyethylene oxide polymer swells via imbibition of aqueous external fluid to (1) increase the size of the dosage form to promote gastric retention, (2) osmotically control the release of drug by providing a constant pressure from the push layer on the pull layer comprising the drug dispersion/solution, (3) support the membrane and maintain the integrity of the tablet in a swollen state, and (4) entrap generated gas (e.g., $CO_2$) to provide buoyancy.

In certain embodiments, the gastroretentive liothyronine compositions of the disclosure are stable, and provide desired sustained delivery of liothyronine or a pharmaceutically acceptable salt thereof, in the GI tract due to the presence at least one swellable water-soluble polymer in the pull layer. In certain embodiments, the pull-layer comprises at least one swellable water-soluble hydrophilic polymer that minimizes the degradation of liothyronine. In certain embodiments, the swellable water-soluble hydrophilic polymer in the pull layer is hypromellose (hydroxypropyl methylcellulose). In certain embodiments, the hypromellose present in the pull layer is a low viscosity hypromellose. In certain embodiments, the hypromellose present in the pull layer is a mixture of low viscosity and high viscosity hypromellose, e.g., METHOCEL™ K3 Premium LV, and optionally, a small amount of METHOCEL™ K15M Premium CR. In certain embodiments, the tablet core swells to support the membrane and maintain the integrity of the dosage form. In certain embodiments, the tablet core swells and entraps $CO_2$ to provide buoyancy to the dosage form. In certain embodiments, the swelling of the tablet core is due to the swelling of the pull layer and the push layer.

In certain embodiments, the liothyronine sodium gastroretentive tablets can comprise a multilayer core comprising i) a pull layer containing liothyronine or a pharmaceutically acceptable salt thereof, an acid, a gas-generating agent, a first osmogen, and at least one swellable water-soluble hydrophilic polymer selected from the group consisting of hydroxypropyl methylcellulose (hypromellose), sodium carboxymethyl cellulose, carbomers, or any mixtures thereof, and ii) a push layer comprising a polyethylene oxide polymer with an average molecular weight of at least 900,000 Da, and a second osmogen; and b) a permeable elastic membrane/functional coat containing at least one orifice and covering at least a portion of the multilayer core.

In certain embodiments, pull layer comprises pull layer blend. In certain embodiments, pull layer blend comprises Drug Intermediate Granules and extra granular components. In certain embodiments, Drug Intermediate Granules comprise 0.052 mg (52 mcg) of liothyronine sodium. 85 mg of calcium sulfate dihydrate, about 15 mg of sucrose, about 0.7 mg of BHT or about 0.1 mg of Vitamin E. In certain embodiments, extragranular portion comprises about 285 mg of sucrose, 50 mg of sodium bicarbonate; about 75 mg of calcium carbonate; about 232 mg of METHOCEL™ K3 LV; about 5 mg of METHOCEL™ K15M Premium CR; 125 mg of succinic acid; about 3.5 mg, about 6 mg, or about 8.5 mg of colloidal silicon dioxide; and about 10 mg of magnesium stearate. In certain embodiments, the Drug Intermediate granules do not include sucrose and instead include 231.5 mg of METHOCEL™ K3 LV from the extragranular blend. In certain embodiments, the push layer comprises about 132 mg of POLYOX™ WSR Coagulant or about 220 mg of POLYOX™ WSR N-60K. In certain embodiments, the push layer further comprises 25 mg or about 15 mg of sodium chloride; about 1.8 or about 3 mg of magnesium stearate; and about 1.2 mg or about 2 mg of Red Pigment Blend. In certain embodiments, the functional coat comprises about 148 mg of EUDFAGIT® RL copolymer and about 22.2 mg of triethyl citrate plasticizer. In certain embodiments, the functional coat comprises about 93 mg of EUDFAGIT® RL copolymer and about 13.8 mg of triethyl citrate plasticizer.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 85 mg of calcium sulfate dihydrate, about 15 mg of sucrose, and about 0.1 mg of Vitamin E. In certain embodiments, extragranular portion comprises about 50 mg of sodium bicarbonate, about 285 mg sucrose, about 125 mg of calcium carbonate, 125 mg of succinic acid, about 3.5 mg of colloidal silicon dioxide, about 10 mg of magnesium stearate, about 81.5 mg of mannitol, about 200 mg of POLYOX® WSR N80 K, about 5 mg of POLYOX® WSR 303.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 85 mg of calcium sulfate dihydrate, about 15 mg of sucrose, and about 0.1 mg of vitamin E. In certain embodiments, the extragranular component comprises about 50 mg of sodium bicarbonate, about 125 mg of calcium carbonate, 125 mg of succinic acid, about 3.5 mg of colloidal silicon dioxide, about 10 mg of magnesium stearate, about 81.5 mg of mannitol, about 200 mg of sodium CMC (AQUALON™ 7L2P), and 5 mg of AQUALON™ 7H4F M. In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 85 mg of calcium sulfate dihydrate, about 15 mg of sucrose, and about 0.1 mg of vitamin E. In certain embodiments, extragranular component comprises about 50 mg of sodium bicarbonate, about 125 mg of calcium carbonate, 125 mg of succinic acid, about 3.5 mg of colloidal silicon dioxide, about 10 mg of magnesium stearate, about 81.5 mg of mannitol, about 205 mg of METHOCEL™ K100 Premium LV.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 85 mg of calcium sulfate dihydrate, about 15 mg of sucrose, and about 0.1 mg of vitamin E. In certain embodiments, extragranular component comprises about 50 mg of sodium bicarbonate, about 75 mg of calcium carbonate, 125 mg of succinic acid, about 3.5 mg of colloidal silicon dioxide, about 10 mg of magnesium stearate, about 79.5 mg of mannitol, about 250 mg of PEO-1NF and about 7 mg of PEO-18NF.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 15 mg of sucrose, and about 0.1 mg of Vitamin E. In certain embodiments, extra granular component comprises about 50 mg of sodium bicarbonate, about 75 mg of calcium carbonate, 125 mg of succinic acid, about 3.5 mg of colloidal silicon dioxide, about 10 mg of magnesium stearate, about 116.5 mg of mannitol, about 300 mg of METHOCEL™ K3 Premium LV, and about 5 mg of METHOCEL™ K15M Premium CR. In certain embodiments, the push layer comprises about 220 mg of POLYOX™ WSR N-60K, 25 mg of sodium chloride as an osmogen; about 3 mg of magnesium stearate; and about 2 mg of Red Pigment Blend. In certain embodiments, the functional coat comprises about 148.2 mg of EUDFAGIT® RL copolymer, about 22.2 mg of triethyl citrate plasticizer, and about 29.6 mg of talc.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 95 mg of sucrose, and about 0.1 mg of Vitamin E. In certain embodiments, extragranular component comprises about 50 mg of sodium bicarbonate, about 75 mg of calcium carbonate, 125 mg of succinic acid, about 3.5 mg of colloidal silicon dioxide, about 10 mg of magnesium stearate, about 116.5 mg of mannitol, about 231.5 mg of METHOCEL™ K3 Premium LV, and about 5 mg of METHOCEL™ K15M Premium CR. In certain embodiments, the push layer comprises about 220 mg of POLYOX™ WSR N-60K, 25 mg of sodium chloride as an osmogen; about 3 mg of magnesium stearate; and about 2 mg of Red Pigment Blend. In certain embodiments, the functional coat comprises about 148.2 mg of EUDFAGIT® RL copolymer, about 22.2 mg of triethyl citrate plasticizer, and about 29.6 mg of talc.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 200 mg of sucrose, and about 0.1 mg of Vitamin E. In certain embodiments, extragranular component comprises about 50 mg of sodium bicarbonate, about 75 mg of calcium carbonate, 125 mg of succinic acid, about 3.5 mg of colloidal silicon dioxide, about 10 mg of magnesium stearate, about 116.5 mg of mannitol, about 231.5 mg of METHOCEL™ K3 Premium LV, and about 5 mg of METHOCEL™ K15M Premium CR. In certain embodiments, the push layer comprises about 220 mg of POLYOX™ WSR N-60K, 25 mg of sodium chloride as an osmogen; about 3 mg of magnesium stearate; and about 2 mg of Red Pigment Blend. In certain embodiments, the functional coat comprises about 148.2 mg of EUDFAGIT® RL copolymer, about 22.2 mg of triethyl citrate plasticizer, and about 29.6 mg of talc.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, bout 15 mg of sucrose, about 85 mg of calcium sulfate dihydrate, and about 0.1 mg of Vitamin E. In certain embodiments, extragranular component comprises, about 185 mg sucrose, about 50 mg of sodium bicarbonate, about 75 mg of calcium carbonate, 125 mg of succinic acid, about 40 mg of POLOXAMER 188, about 3.5 mg of colloidal silicon dioxide, about 10 mg of magnesium stearate, about 231.5 mg of METHOCEL™ K3 Premium LV, and about 5 mg of METHOCEL™ K15M Premium CR. In certain embodiments, the push layer comprises about 220 mg of POLYOX™ WSR N-60K, 25 mg of sodium chloride; about 3 mg of magnesium stearate; and about 2 mg of Red Pigment Blend. In certain embodiments, the functional coat comprises about 148.2 mg of EUDFAGIT® RL copolymer, about 22.2 mg of triethyl citrate plasticizer, and about 29.6 mg of talc.

In certain embodiments, pull layer comprises pull layer blend. In certain embodiments, pull layer blend comprises Drug Intermediate Granules and extra granular components. In certain embodiments, Drug Intermediate Granules comprise about 0.052 mg (52 mcg) of liothyronine sodium, about 15 mg of sucrose, about 85 mg calcium sulfate dihydrate, and about 0.1 mg of Vitamin E. In certain embodiments, extragranular component comprises about 185 mg of sucrose, about 50 mg of sodium bicarbonate, about 75 mg of calcium carbonate, 125 mg of succinic acid, about 3.5 mg of colloidal silicon dioxide, about 10 mg of magnesium stearate, about 231.5 mg of METHOCEL™ K3 Premium LV, and about 5 mg of METHOCEL™ K15M Premium CR. In certain embodiments, the push layer comprises about 220 mg of POLYOX™ WSR N-60K, 25 mg of sodium chloride as an osmogen; about 3 mg of magnesium stearate; and about 2 mg of Red Pigment Blend. In certain embodiments, the functional coat comprises about 148.2 mg of EUDFAGIT® RL copolymer, about 22.2 mg of triethyl citrate plasticizer, and about 29.6 mg of talc.

Figure 1:
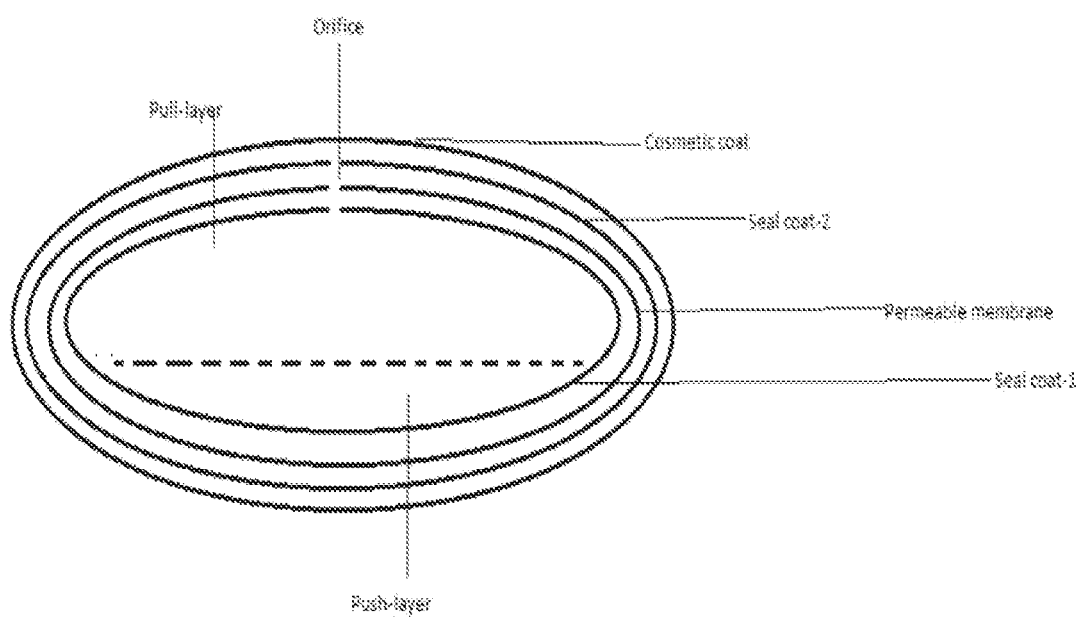

For the purpose of illustration and not limitation, FIG. 1 provides a schematic representation of the gastroretentive dosage form, according to certain embodiments, illustrating a bilayer tablet core, comprising a push layer and a pull layer, Seal coat-1 surrounding the tablet core, a permeable elastic membrane surrounding Seal coat-1, Seal coat-2/over coat surrounding the permeable membrane, a cosmetic coat surrounding Seal coat-2, and an orifice passing through Seal coat-1, the membrane, and Seal coat-2, wherein the orifice is in fluid communication with the pull layer.

Multilayered Tablet Core

In certain embodiments, the multilayered tablet core comprises a push layer and a pull layer. In certain embodiments, the pull layer and the push layer are compressed horizontally into a bilayer tablet core. In certain embodiments, the multilayered tablet core comprises a push layer between two pull layers. In certain embodiments, the ratio of the pull layer and the push layer in the tablet core is between about 1:1 to about 6:1. In certain embodiments, the ratio of the pull layer and the push layer in the tablet core is about 1:1, about 2:1, about 3:1, about 4:1, about 5:1, about 6:1, or any intermediate ratios therein.

Pull Layer

In certain embodiments, the pull layer includes a thyroid hormone drug, e.g., liothyronine or a pharmaceutically acceptable salt thereof, at least one water-soluble hydrophilic polymer, at least one acid, and a gas-generating agent. In certain embodiments, the pull-layer further comprises at least one osmogen. In certain embodiments, the pull-layer includes at least one wicking agent to increase wetting of the water-soluble hydrophilic polymer. In certain embodiments, the pull-layer optionally includes at least one stabilizing agent to reduce the degradation of liothyronine or pharmaceutically acceptable salts thereof. In certain embodiments, the selection of excipients in the pull layer is such that the excipients provide proper tableting characteristics, without destabilizing or degrading liothyronine or a pharmaceutically acceptable salt thereof.

In certain embodiments, the gastroretentive liothyronine compositions of the disclosure contain from about 0.0001% w/w to about 1% w/w of liothyronine or a pharmaceutically acceptable salt thereof, based on the total weight of the dosage form. In certain embodiments, the gastroretentive liothyronine compositions of the disclosure contain from about 0.001% w/w to about 0.01% w/w of liothyronine or a pharmaceutically acceptable salt thereof, based on the total weight of the dosage form. In certain embodiments, the gastroretentive liothyronine compositions of the disclosure contain liothyronine or a pharmaceutically acceptable salt thereof in an amount of from about 0.001 µg to about 200 µg, from about 0.01 µg to about 100 µg, or from about 0.1 µg to about 75 µg, about 1 µg, about 2 µg, about 3 µg, about 4 µg, about 5 µg, about 6 µg, about 7. µg, about 8. µg, about 9. µg about 10 µg, about 11 µg, about 12 µg, about 13 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 61 µg, about 62 µg, about 63 µg, about 64 µg, about 65 µg, about 66 µg, about 67 µg, about 68 µg, about 69 µg, about 70 µg, about 71 µg, about 72 µg, about 73 µg, about 74 µg, about 75 µg, about 76 µg, about 77 µg, about 78 µg, about 79 µg, about 80 µg, about 81 µg, about 82 µg, about 83 µg, about 84 µg, about 85 µg, about 86 µg, about 87 µg, about 88 µg, about 89 µg, about 90 µg, about 91 µg, about 92 µg, about 93 µg, about 94 µg, about 95 µg, about 96 µg, about 97 µg, about 98 µg, about 99 µg, about 100 µg, or intermediate values therein.

In certain embodiments, the pull layer comprises a water-soluble hydrophilic polymer that provides proper tableting characteristics, without destabilizing or degrading liothyronine or a pharmaceutically acceptable salt thereof. In certain embodiments, the water-soluble hydrophilic polymer is selected from the group comprising hydroxypropyl methylcellulose (hypromellose), sodium carboxymethyl cellulose, carbomers, or any mixtures thereof.

In certain embodiments, the water-soluble hydrophilic polymer is sodium carboxymethylcellulose having a viscosity, in 2% aqueous solution at 25° C., of from about 25 cp to about 5,000 cp. In certain embodiments, the pull layer includes at least one sodium carboxymethylcellulose having a viscosity of from about 25 cp to about 50 cp, from about 50 cp to about 100 cp, from about 50 cp to about 200 cp, from about 200 cp to about 800 cp, from about 400 cp to about 600 cp, from about 400 cp to about 800 cp, from about 800 cp to about 3,100 cp, from about 1,000 cp to about 2,800 cp, from about 1,500 cp to about 2,500 cp, from about 1,500 cp to about 3,000 cp, from about 1,500 cp to about 3,100 cp, from about 2,500 cp to about 4,500 cp, from 1,500 cp to about 3,100 cp, or any intermediate ranges therein. In certain embodiments, the pull layer comprises a mixture of two or more sodium carboxymethylcellulose polymers, each having a viscosity, in 2% aqueous solution at 25° C., of from about 25 cp to about 50 cp, from about 50 cp to about 100 cp, from about 50 cp to about 200 cp, from about 200 cp to about 800 cp, from about 400 cp to about 600 cp, from about 400 cp to about 800 cp, from about 800 cp to about 3,100 cp, from about 1,000 cp to about 2,800 cp, from about 1,500 cp to about 2,500 cp, from about 1,500 cp to about 3,000 cp, from about 1,500 cp to about 3,100 cp, from about 2,500 cp to about 4,500 cp, from 1,500 cp to about 3,100 cp, or any intermediate ranges therein.

In certain embodiments, the water-soluble hydrophilic polymer comprises at least one low viscosity hypromellose having a viscosity, in 2% aqueous solution at 25° C., of less than 5,000 cp. In certain embodiments, the water-soluble hydrophilic polymer comprises at least one low viscosity hypromellose having a viscosity, in 2% aqueous solution at 25° C., of from about 2.3 cp to about 3.3 cp, from about 2.4 cp to about 3.6 cp, from about 4.0 cp to about 6.0 cp, from about 4.8 cp to about 7.2 cp, from about 12 cp to about 18 cp, from about 80 cp to about 120 cp, from about 2,663 cp to about 4,970 cp, or any intermediate ranges therein. In certain embodiments, the water-soluble hydrophilic polymer comprises a high viscosity hypromellose with a viscosity, in 2% aqueous solution at 25° C., of greater than 5,000 cp. In certain embodiments, the water-soluble hydrophilic polymer comprises a high viscosity hypromellose with a viscosity, in 2% aqueous solution at 25° C., of from about 9,525 cp to about 17,780 cp, from about 13,275 cp to about 24,780 cp, from about 75,000 cp to about 140,000 cp, or any intermediate ranges therein. In certain embodiments, the water-soluble hydrophilic polymer in the pull layer includes a mixture of a high viscosity hypromellose and a low viscosity hypromellose. In certain embodiments, the weight ration of the low viscosity hypromellose and the high viscosity hypromellose is from 50:50 to 99:1. In certain embodiments, the weight ration of the low viscosity hypromellose and the high viscosity hypromellose is about 80:20, about 81:19, about 82:18, about 83:17, about 84:16, about 85:15, about 86:14, about 87:13, about 88:12, about 89:11, about 90:10, about 91:9, about 92:8, about 93:7, about 94:6, about 95:5, about 96:4, about 97:3, about 98:2, about 99.9:0.1, or any intermediate ratios therein. In certain embodiments, the high viscosity hypromellose is present in an amount of from 1% w/w to 70% w/w of the low viscosity hypromellose. In certain embodiments, the high viscosity hypromellose is present in an amount of about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 30% w/w, about 35% w/w, about 40% w/w, about 45% w/w, about 50% w/w, about 55% w/w, about 60% w/w, about 65% w/w, about 70% w/w, or any intermediate values therein, of the low viscosity hypromellose.

In certain embodiments, the viscosity of the water-soluble hydrophilic polymer is adjusted to provide desired sustained release profile and substantially complete drug recovery at the end of the dosing period.

In certain embodiments, the water-soluble polymer in the pull layer is present in an amount of from about 5% w/w to about 70% w/w, based on the total weight of the pull layer. In certain embodiments, the water-soluble polymer in the pull layer is present in an amount of about 5% w/w, about 10% w/w, about 15% w/w, about 20% w/w, about 25% w/w, about 30% w/w, about 35% w/w, about 40% w/w, about 45%, w/w about 50% w/w, about 55% w/w, about 60% w/w, about 65% w/w, about 70% w/w, or any intermediate values therein, based on the total weight of the pull layer.

In certain embodiments, the pull layer further includes a stabilizer to prevent the degradation of liothyronine or a pharmaceutically acceptable salt thereof. In certain embodiments, liothyronine, or a pharmaceutically acceptable salt thereof, degrades through oxidation and/or deiodination, and other excipient-active interactions in which de-iodination is predominant. Since the degradation pathway is oxidation, addition of an antioxidant in the pull layer can further aid in stabilizing liothyronine or a pharmaceutically acceptable salt thereof. In certain embodiments, the stabilizer is an antioxidant selected from the group consisting of, but not limited to, ascorbic acid and its salts, tocopherols, sulfite salts such as sodium metabisulfite or sodium sulfite, sodium sulfide, butylated hydroxyanisole (BHA), butylated hydroxytoluene (BHT), ascorbyl palmitate, propyl gallate, and any combination thereof. In certain embodiments, the stabilizer is present in an amount of from about 0.001% wt/wt to about 20% w/w, based on the total weight of the pull layer. In certain embodiments, the stabilizer is present in an amount of about 0.001% w/w, about 0.002% w/w, about 0.003% w/w, about 0.004% w/w, about 0.005% w/w, about 0.006% w/w, about 0.007% w/w, about 0.008% w/w, about 0.009% w/w, about 0.01% w/w, about 0.02% w/w, about 0.03% w/w, about 0.04% w/w, about 0.05% w/w, about 0.06% w/w, about 0.07% w/w, about 0.08% w/w, about 0.09% w/w, about 0.10% w/w, about 0.2% w/w, about 0.3% w/w, about 0.4% w/w, about 0.5% w/w, about 1% w/w, about 5% w/w, about 10% w/w, about 15% w/w, about 20% w/w, or any intermediate values therein, based on the total weight of the pull layer. In certain embodiments, pull layer does not include a stabilizer. In certain embodiments, stability of liothyronine or a pharmaceutically acceptable salt thereof is improved with the use of specific packaging configurations, e.g., using Oxyguard bottles, oxygen scavengers in the bottle/Oxygaurd bottle, and nitrogen purging while packaging.

In certain embodiments, the pull layer includes Drug Intermediate and extragranular component. In certain embodiments, the Drug Intermediate comprises liothyronine or a pharmaceutically acceptable salt thereof. In certain embodiments, the Drug Intermediate is blended with extragranular component to provide a pull layer blend. In certain embodiments, Drug Intermediate is a Drug Intermediate granule made via dry granulation, dry mixing, or wet granulation process. In certain embodiments, Drug Intermediate comprises Drug Intermediate granules made via wet granulation. In certain embodiments, solvent used in wet granulation process comprises ethanol 200 proof, isopropyl alcohol (99% v/v), water, or a mixture thereof. In certain embodiments, the solvent used in wet granulation process does not include water. In certain embodiments, Drug Intermediate comprises Drug Intermediate granules made via dry granulation. In certain embodiments, dry granulation comprises roller compaction or slugging. In certain embodiments, the Drug Intermediate is a Drug Intermediate blend comprising a dry mix/dry mix blend of liothyronine or a pharmaceutically acceptable salt thereof and various excipients. In certain embodiments, Drug Intermediate Granules comprise liothyronine or a pharmaceutically acceptable salt thereof and at least one stabilizer. In certain embodiments, presence of a stabilizer in the Drug Intermediate granules is optional. In certain embodiments, Drug intermediate blend does not include a stabilizer. In certain embodiments, Drug Intermediate, e.g., Drug intermediate Blend or drug Intermediate Granules, comprises at least one filler selected from the group consisting of sucrose, lactose, mannitol, microcrystalline cellulose, calcium sulfate dihydrate, dicalcium sulfate, and mixtures thereof. In certain embodiments, Drug Intermediate comprises at least one filler in an amount of from about 40% w/w to about 99.9% w/w, based on the total weight of the Drug Intermediate. In certain embodiments, the filler is present in an amount of about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, about 96% w/w, about 97% w/w, about 98% w/w, about 99% w/w, about 99.9% w/w, based on the total weight of the Drug Intermediate.

In certain embodiments, Drug Intermediate comprises at least one water-soluble hydrophilic polymer. In certain embodiments, the water-soluble hydrophilic polymer is selected from the group comprising hydroxypropyl methylcellulose, sodium carboxymethyl cellulose, carbomers, or any mixtures thereof. In certain embodiments, the water-soluble hydrophilic polymer is present in an amount of about 50% w/w, about 55% w/w, about 60% w/w, about 65% w/w, about 70% w/w, about 75% w/w, about 80% w/w, about 85% w/w, about 90% w/w, about 95% w/w, about 96% w/w, about 97% w/w, about 98% w/w, about 99% w/w, about 99.9% w/w, based on the total weight of the Drug intermediate. In certain embodiments, the water-soluble hydrophilic polymer is a filler. In certain embodiments, Drug Intermediate further comprises at least one glidant selected from the group comprising talc, colloidal silicon dioxide, magnesium trisilicate, powdered cellulose, starch, tribasic calcium phosphate, and any combination thereof. In certain embodiments, the glidant is colloidal silicon dioxide. In certain embodiments, the glidant is present in an amount of from about 0.1% w/w to about 5% w/w, based on the total weight of the Drug Intermediate.

In certain embodiments, the extragranular component comprises a gas-generating agent, at least one organic acid, at least one osmogen, and at least one water-soluble hydrophilic polymer. In certain embodiments, the extragranular component further comprises at least one lubricant. In certain embodiments, the extragranular component further comprises at least one glidant. In certain embodiments, the gas-generating agent(s) is present in Drug intermediate and/or the extragranular component. In certain embodiments, the water-soluble hydrophilic polymer is present in the Drug Intermediate and/or the extragranular component.

In certain embodiments, the extragranular component in the pull layer includes at least one acid to accelerate generation of $CO_2$ from gas-generating agents and/or stabilize the drug. In certain embodiments, the acid is present in intermediate drug granules and/or the extragranular component. In certain embodiments, the acid is preferably present in extragranular component only. In certain embodiments, the acid is an organic acid selected from the group consisting of succinic acid, citric acid, acetic acid, stearic acid, benzoic acid, malic acid, fumaric acid, tartaric acid, and combinations thereof. In certain embodiments, the acid is succinic acid. In certain embodiments, the acid is present in an amount of from about 5% w/w to about 50% w/w of the pull layer. In certain embodiments, the acid is present in an amount of about 5% w/w, about 10% w/w, about 15% w/w, about 20% w/w, about 25% w/w, about 30% w/w, about 35% w/w, about 40% w/w, about 45% w/w, about 50% w/w, or any intermediate values therein, based on the total weight of the pull layer. In certain embodiments, rate of generation of $CO_2$ from the gas-generating agents depends upon the particle size of the acid, e.g., a reduction in particle size accelerates generation of $CO_2$.

In certain embodiments, the Drug Intermediate and/or extragranular component in the pull layer includes a gas-generating agent that generates gas (e.g., $CO_2$) for rapid expansion and floatation of the dosage form. In certain embodiments, the gas generating agent is selected from the group consisting of carbonate salts of alkali metals, carbonate salts of alkaline earth metals, bicarbonate salts of alkali metals, bicarbonate salts of alkaline earth metals, and mixtures thereof. The gas-generating agent, with imbibition of aqueous external fluid into the dosage form, interacts with acid for in situ $CO_2$ gas generation. In certain embodiments, the presence of at least one organic acid in the pull layer results in generation of $CO_2$ with imbibition of external aqueous fluid in the dosage form, irrespective of the pH of dissolution medium, e.g., in vitro, and in vivo dissolution mediums, e.g., gastric fluid and SGF. and gastric fluid. In certain embodiments, the presence of at least one acid in the pull layer allows for rapid generation of gas with imbibition of external aqueous fluid into the dosage form. In certain embodiments, the gas generating agent is a carbonate salt of an alkali or alkaline earth metal. In certain embodiments, the gas generating agent is calcium carbonate, sodium carbonate, or magnesium carbonate. In certain embodiments, the gas generating agent is a bicarbonate salt of an alkali or alkaline earth metal.

In certain embodiments, the gas generating agent is sodium bicarbonate. In certain embodiments, the gas generating agent is a mixture of a carbonate salt of an alkaline earth metal and a bicarbonate salt of an alkali metal. In certain embodiments, the gas generating agent is a mixture of calcium carbonate and sodium bicarbonate. In certain embodiments, the mixture of calcium carbonate and sodium bicarbonate provides a desired sustained release of $CO_2$. In certain embodiments, the gas-generating agent is present in an amount of from at least about 5% w/w to about 50% w/w, based on the total weight of the pull layer. In certain embodiments, the gas-generating agent (e.g., carbonate salt, bicarbonate salt, or a mixture thereof) is present in an amount of about 5% w/w, about 10% w/w, about 15% w/w, about 20% w/w, about 25% w/w, about 30% w/w, about 35% w/w, about 40% w/w, about 45% w/w, about 50% w/w, or any intermediate values therein, based on the total weight of the pull layer.

In certain embodiments, the extragranular component in the pull layer includes at least one osmogen to facilitate imbibition of fluid (e.g., aqueous dissolution medium/SGF and/or gastric fluid) into the pull layer. In certain embodiments, imbibition of external aqueous fluid into the pull layer facilitates reaction of the at least one acid and the gas generating agent, both present in the pull layer, for in situ generation of $CO_2$. In certain embodiments, the amount of osmogen in the pull layer determines the floating time and floating lag time of the gastroretentive compositions of the disclosure. In certain embodiments, the compositions of the disclosure exhibit an increase in floating time and a decrease in floating lag time with increasing the amount of osmogen in the pull layer. In certain embodiments, the osmogen is selected from the group consisting of sodium chloride, potassium chloride, potassium sulfate, lithium sulfate, sodium sulfate, lactose and sucrose combination, lactose and dextrose combination, sucrose, dextrose, mannitol, dibasic sodium phosphate, and combinations thereof. In certain embodiments, the osmogen is present in an amount of from about 5% w/w to about 50% w/w, based on the total weight of the pull layer. In certain embodiments, the osmogen is present in an amount of about 5% w/w, about 10% w/w, about 15% w/w, about 20% w/w, about 25% w/w, about 30% w/w, about 35% w/w, about 40% w/w about 45% w/w, about 50% w/w, or any intermediate values therein, based on the total weight of the pull layer.

In certain embodiments, the extragranular component in the pull layer further includes at least one lubricant selected from the group comprising magnesium stearate, glyceryl monostearates, glyceryl behenate, palmitic acid, talc, carnauba wax, calcium stearate sodium, sodium or magnesium lauryl sulfate, sodium stearyl fumarate, calcium soaps, zinc stearate, polyoxyethylene monostearates, calcium silicate, silicon dioxide, hydrogenated vegetable oils and fats, stearic acid, and any combinations thereof. In certain embodiments, the lubricant is magnesium stearate. In certain embodiments, the lubricant is present in an amount of from about 0.1% w/w to about 5% w/w, based on the total weight of the pull layer. In certain embodiments, the lubricant is present in an amount of about 0.1% w/w, about 0.2% w/w, about 0.3% w/w, about 0.4% w/w, 0.5 wt %, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.5% w/w, about 3.0% w/w, about 3.5% w/w, about 4.0% w/w, about 4.5% w/w, about 5.0% w/w, or any intermediate values therein, based on the total weight of the pull layer. In certain embodiments, the extragranular component in the pull layer includes at least one glidant selected from the group comprising talc, colloidal silicon dioxide, magnesium trisilicate, powdered cellulose, starch, tribasic calcium phosphate, and any combination thereof. In certain embodiments, the glidant is colloidal silicon dioxide. In certain embodiments, the glidant is present in an amount of from about 0.1% w/w to about 5% w/w, based on the total weight of the pull layer. In certain embodiments, the glidant is present in an amount of about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 2% w/w, about 3% w/w, about 4% w/w, about 5% w/w, or any intermediate values therein, of the pull layer.

In certain embodiments, the extragranular component in the pull layer further comprises mannitol. In certain embodiments, mannitol is used as an osmogen, a filler and/or as a compression aid. In certain embodiments, mannitol is used as a secondary osmotic agent.

Push Layer

In certain embodiments, the push layer comprises a push layer blend comprising a swellable water-soluble hydrophilic polymer, an osmogen, a lubricant, and a color pigment. In certain embodiments, the swellable water-soluble hydrophilic polymer is a polyethylene oxide polymer. In certain embodiments, the polyethylene oxide polymer in the push layer has an average molecular weight of greater than or equal to about 600,000 Da. In certain embodiments, the average molecular weight of the polyethylene oxide polymer in the push layer is about 600,000 Da, about 700,000 Da, about 800,000 Da, about 900,000 Da, about 1000,000 Da, about 2000,000 Da, about 3000,000 Da, about 4000,000 Da, about 5000,000 Da, about 6000,000 Da, about 7000,000 Da, or any intermediate values thereof. In certain embodiments, the amount of polyethylene oxide polymer present in the push layer is enough to provide substantially complete recovery of liothyronine or a pharmaceutically acceptable salt thereof the remaining dosage form, with push layer only, collapses/shrinks for complete emptying of the composition from the GI tract and the patient. In certain embodiments, the polyethylene oxide polymer (POLYOX®) is present in an amount of from about 50% w/w to about 99% w/w, based on the total weight of the push layer. In certain embodiments, the POLYOX® is present in an amount of about 50% w/w, about 55% w/w, about 60% w/w, about 65% w/w, about 70% w/w, about 75% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w, about 91% w/w, about 92% w/w, about 93% w/w, about 94% w/w, about 95% w/w, about 96% w/w, about 97% w/w, about 98% w/w, about 99% w/w, or any intermediate values therein, based on the total weight of the push layer. In certain embodiments, the POLYOX® in the push layer is present in an amount of amount 5% w/w to about 40% w/w, based on the total weight of the coated tablet composition. In certain embodiments, the POLYOX® is present in an amount of about 5% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 25% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, or any intermediate values therein, based on the total weight of the coated tablet composition.

In certain embodiments, the amount and average molecular weight of POLYOX® in the push layer affects the drug release profile. In certain embodiments, the average molecular weight of POLYOX® in the push layer is selected to provide the desired expansion volume of the push layer for substantially complete drug recovery in a specific time period. In certain embodiments, the average molecular weight of POLYOX® in the push layer is selected to provide the desired expansion rate and expansion volume for substantially complete drug recovery in a specific time period. In certain embodiments, the substantially complete drug recovery comprises release of from about 75 wt % to about 95 wt % of liothyronine or a pharmaceutically acceptable salt thereof, based on the total amount of liothyronine, or a pharmaceutically acceptable salt thereof, present in the composition.

In certain embodiments, the push layer comprises a lubricant selected from the group comprising magnesium stearate, glyceryl monostearates, glyceryl behenate, palmitic acid, talc, carnauba wax, calcium stearate sodium, sodium or magnesium lauryl sulfate, sodium stearyl fumarate, calcium soaps, zinc stearate, polyoxyethylene monostearates, calcium silicate, silicon dioxide, hydrogenated vegetable oils and fats, stearic acid, and any combinations thereof. In certain embodiments, the lubricant is magnesium stearate. In certain embodiments, the lubricant is present in an amount of about 0.1% w/w to about 5% w/w, based on the total weight of the push layer. In certain embodiments, the lubricant is present in an amount of about 0.1% w/w, about 0.2% w/w, about 0.3% w/w, about 0.4% w/w, 0.5 wt %, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.5% w/w, about 3.0% w/w, about 3.5% w/w, about 4.0% w/w, about 4.5% w/w, about 5.0% w/w, or any intermediate values therein, based on the total weight of the push layer.

In certain embodiments, the push layer comprises at least one osmogen to provide a concentration differential for osmotic flow of liquid into the composition. In certain embodiments, the extent of swelling of the swellable water-soluble hydrophilic polymer in the push layer depends upon the rate of imbibition of water into the push layer. In certain embodiments, the rate and extent of imbibition of water into the push layer depends upon the type and amount of osmogen present in the push layer. In certain embodiments, the rate and extent of imbibition of water into the push layer further depends upon the coating weight gain of the dosage form and/or the permeability of the membrane. As the water-soluble polymer in the push layer absorbs water, it expands in volume, which pushes the pull layer containing the drug out of the tablet core through the orifice in the membrane.

In certain embodiments, the osmogen is selected from the group consisting of sodium chloride, potassium chloride, potassium sulfate, lithium sulfate, sodium sulfate, a lactose and sucrose combination, a lactose and dextrose combination, sucrose, dextrose, mannitol, dibasic sodium phosphate, and combinations thereof. In certain embodiments, the osmogen is present in an amount of from about 5% w/w to about 50% w/w, based on the total weight of the push layer.

In certain embodiments, the osmogen is present in an amount of about 5% w/w, about 10% w/w, about 15% w/w, about 20% w/w, about 25% w/w, about 35% w/w, about 40% w/w about 45% w/w about 50% w/w or any intermediate values therein, based on the total weight of the push layer. In certain embodiments, the osmogen is present in an amount of about 5% w/w, about 10% w/w, about 11% w/w, about 12% w/w, about 13% w/w, about 14% w/w, about 15% w/w about 16% w/w about 17% w/w about 18% w/w, about 19% w/w, about 20% w/w, or any intermediate values therein, based on the total weight of the push layer.

In certain embodiments, the push layer includes at least one coloring agent for identifying the push layer in the multilayered tablet core. In certain embodiments, the coloring agent in the push layer is useful for identifying the push-layer side while drilling a delivery orifice on the drug-layer side (pull-layer side) of the coated multilayered tablets. In certain embodiments, the coloring agent comprises, but is not limited to, a water soluble dye, Aluminum Lake, iron oxide, natural colors, titanium oxide, and the like. Suitable Aluminum Lake coloring agents include, but are not limited to, Aluminum lake FD&C Blue #1, Aluminum lake FD&C Red #30, Aluminum lake FD&C Red #40, Aluminum lake FD&C Yellow #6, Aluminum lake FD&C Yellow #10, or combinations thereof. In certain embodiments, the pigment is an iron oxide pigment, e.g., oxide pigment black or Red blend. In certain embodiments, the pigment is present in an amount of from about 0.1% w/w to about 2% w/w, based on the total weight of the push layer.

Membrane/Functional Coat

The compositions of the disclosure comprise a membrane that is a water-insoluble, permeable elastic membrane surrounding the multilayer tablet core. The membrane allows the flow of gastric fluid into the composition, which initiates reaction of acid and gas-generating agents present in the tablet core, for quick generation of $CO_2$; and the membrane flexibility allows for rapid expansion and floatation of the composition with the generated $CO_2$. In certain embodiments, the membrane comprises at least one plasticizer and at least one copolymer of ethyl acrylate, methyl methacrylate, and trimethylammonioethyl methacrylate chloride (ammonium polymethacrylate copolymer). The copolymer(s) provides desired permeability and flexibility to the membrane and the plasticizer(s) provides elasticity and tensile/mechanical strength to the membrane. The plasticizer(s) and the copolymer(s) provide desired elasticity and permeability to the membrane, ensuring that the membrane does not rupture upon expanding and that the osmotic gastroretentive drug delivery system provides the desired characteristics for drug release, hydrodynamic balance, and mechanical strength to withstand variations in pH and shear in the stomach during fed or fasted conditions. In certain embodiments, the membrane flexibility is associated with the presence of at least one plasticizer. In certain embodiments, the membrane flexibility is associated with the presence of at least one plasticizer and at least one copolymer of ethyl acrylate, methyl methacrylate, and trimethylammonioethyl methacrylate chloride with a glass transition temperature (Tg) of from about 50° C. and about 65° C. In certain embodiments, the flexibility of the copolymer is associated with the glass transition temperature (Tg) of from about 50° C. and about 65° C. In certain embodiments, as dissolution of the active agent in the tablet core proceeds, the plasticizer leaches out of the membrane. In certain embodiments, notwithstanding depleting plasticizer levels, the membrane retains enough elasticity due to the presence of at least one copolymer of ethyl acrylate, methyl methacrylate, and trimethylammonioethyl methacrylate chloride, having a glass transition temperature (Tg) of from about 50° C. and about 65° C., to squeeze the dosage form out through the pyloric sphincter, after at least about 80% of the drug is released. Hydrophilic plasticizers suitable for the disclosure include, but are not limited to, glycerin, polyethylene glycols, polyethylene glycol monomethyl ether, propylene glycol, and sorbitol sorbitan solution. Hydrophobic plasticizers suitable for the disclosure include, but are not limited to, acetyl tributyl citrate, acetyl triethyl citrate, castor oil, diacetylated monoglycerides, dibutyl sebacate, diethyl phthalate, triacetin, tributyl citrate, triethyl citrate, gelucire 39/01, and gelucire 43/01. In certain embodiments, the plasticizers include various polyethylene glycols, glycerin, and/or triethyl citrate. In a preferred embodiment of the disclosure, the plasticizer is triethyl citrate.

In certain embodiments of the disclosure, the permeable elastic membrane comprises at least one copolymer containing ethyl acrylate, methyl methacrylate, and trimethylammonioethyl methacrylate chloride in a ratio of 1:2:0.2 (EUDRAGIT® RL polymer) to improve permeability, and at least one water-soluble hydrophilic polymer and/or a water-soluble nonionic polymer that act(s) as a pore former, to modify its elasticity, permeability, and tensile strength. In certain embodiments, the EUDRAGIT® RL polymer comprises EUDRAGIT® RL 30D (copolymer dispersion of ethyl acrylate, methyl methacrylate, and trimethylammonioethyl methacrylate chloride, 1:2:0.2), EUDRAGIT® RL 12.5 (copolymer of ethyl acrylate, methyl methacrylate, and trimethylammonioethyl methacrylate chloride, 1:2:0.2), EUDRAGIT® RL 100 (granules comprising copolymer of ethyl acrylate, methyl methacrylate, and trimethylammonioethyl methacrylate chloride, 1:2:0.2), and EUDRAGIT® RL PO (copolymer of ethyl acrylate, methyl methacrylate, and trimethylammonioethyl methacrylate chloride, 1:2:0.2 in powder form). In certain embodiments of the disclosure, the permeable elastic membrane comprises at least one of EUDRAGIT® RS polymer to improve permeability, and at least one water-soluble hydrophilic polymer and/or a water-soluble nonionic polymer that act(s) as a pore former, to modify its elasticity, permeability, and tensile strength. In certain embodiments, the EUDRAGIT® RS polymer comprises EUDRAGIT® RS 30D (copolymer dispersion of ethyl acrylate, methyl methacrylate, and trimethylammonioethyl methacrylate chloride, 1:2:0.1), EUDRAGIT® RS 12.5 (copolymer of ethyl acrylate, methyl methacrylate, and trimethylammonioethyl methacrylate chloride, 1:2:0.1), EUDRAGIT® RS 100 (granules comprising copolymer of ethyl acrylate, methyl methacrylate, and trimethylammonioethyl methacrylate chloride, 1:2:0.1), and EUDRAGIT® RS PO (copolymer of ethyl acrylate, methyl methacrylate, and trimethylammonioethyl methacrylate chloride, 1:2:0.1 in powder form).

In certain embodiments, the permeable elastic membrane provides desired characteristics for drug release and tensile strength to withstand peristalsis and mechanical contractility of the stomach (shear). The combination of (1) a water-soluble hydrophilic polymer in the tablet core, and (2) the unique permeable elastic membrane formed over the tablet core by the coating of a homogeneous dispersion of (a) at least one of EUDRAGIT® RL polymer to improve permeability, and (b) at least one polymer selected from the group consisting of EUDRAGIT® NE 30D, EUDRAGIT®NM 30D (collectively "neutral polymethacrylate copolymer), and KOLLICOAT® SR 30D, to improve mechanical strength (tensile strength), provides the desired extended drug release while maintaining the integrity of the tablet core in an expanded state, thus extending the gastric residence time and preventing the dosage form from being emptied from the stomach until substantial or complete release of the drug, usually after a prolonged period. In certain embodiments, at least one of the EUDRAGIT® RL copolymer is present in a ratio with at least one of KOLLICOAT® SR 30D/EUDRAGIT® NE 30D/EUDRAGIT®NM 30D of between 0:100 and 100:0. In certain embodiments, at least one of EUDRAGIT® RL copolymer and at least one of KOLLICOAT® SR 30D/EUDRAGIT® NE 30D/EUDRAGIT®NM 30D are present in a ratio of between about 0.5:99.5 to about 99.5:0.5, including, but not limited to: including, but not limited to: 1:99, 2:98, 3:97, 4:96, 5:95, 6:94, 7:93, 8:92, 9:91, 10:90, 11:89, 12:88, 13:87, 14:86, 15:85, 16:84, 17:83, 18:82, 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:56, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34, 67:33, 68:32, 69:31, 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, 99:1, or any intermediate values thereof.

In certain embodiments, examples of water insoluble components of the permeable elastic membrane include, but are not limited to, copolymers of ethyl acrylate, methyl methacrylate, and trimethylammonioethyl methacrylate chlorides; cellulose acetate phthalate; ethyl cellulose; and hypromellose acetate succinate.

In certain embodiments, the permeable elastic membrane comprises EUDRAGIT® RL polymer, a plasticizer, and an anti-tacking agent.

In certain embodiments, the permeable elastic membrane comprises EUDRAGIT® RL copolymer and EUDRAGIT® NE copolymer. In certain embodiments, the permeable elastic membrane comprises EUDRAGIT® RL copolymer and KOLLICOAT® SR. In certain embodiments, the membrane further includes at least one pore former. In certain embodiments, the pore formers and plasticizers modify membrane permeability, membrane elasticity, and tensile strength. In certain embodiments, the membrane does not include any pore former. In certain embodiments, the solvent used for coating comprises acetone, water, ethanol, isopropyl alcohol, or any mixture thereof. In certain embodiments, the solvent is a mixture of acetone and water, a mixture of ethanol and isopropyl alcohol, a mixture of isopropyl alcohol and water, or a mixture of water, ethanol, and isopropyl alcohol. In certain embodiments, the solvent is a mixture of acetone and water or a mixture of acetone and ethanol.

In certain embodiments, the coating composition includes at least one EUDRAGIT® RL copolymer to improve permeability, and at least one plasticizer to improve mechanical strength (tensile strength). In certain embodiments, permeability, elasticity, and tensile strength of the membrane determines the floating time and floating lag time of the osmotic gastroretentive delivery system of the disclosure. In certain embodiments, the membrane permeability, elasticity, and tensile strength is determined by permeability and elasticity of the polymers present in the membrane. In certain embodiments, the compositions of the disclosure exhibit an increase in floating time and a decrease in floating lag time with increasing membrane permeability. In certain embodiments, permeability of ammonium chloride salt of polymethacrylate copolymer is enhanced on exchange of chloride anion with other anions. In certain embodiments, the chloride anion is exchanged with nitrate ions, sulfate ions, succinate ions, or acetate ions. In certain embodiments, exchange of chloride anions with anions of higher hydrated anion radius improves membrane permeability.

In certain embodiments, permeability of the permeable elastic membrane is adjusted to provide a floating lag time of about 180 minutes or less; and a floating time of at least about 6 hours, e.g., from about 6 hours to about 24 hours. In certain embodiments, the osmotic, floating gastroretentive dosage form of the disclosure comprises a membrane containing a copolymer of ethyl acrylate, methyl methacrylate, trimethylammonioethyl methacrylate chloride, e.g., EUDRAGIT® RL and/or EUDRAGIT® RS, and exhibits a floating lag time of about 120 minutes or less; and a floating time of at least about 6 hours. In certain embodiments, the copolymer of ethyl acrylate, methyl methacrylate, trimethylammonioethyl methacrylate chloride is present in an amount of from about 50% to about 99.5% w/w, based on the total coating weight gain, to provide desired tensile strength, and elasticity for rapid expansion of the membrane. In certain embodiments, the copolymer of ethyl acrylate, methyl methacrylate, trimethylammonioethyl methacrylate chloride is present in an amount of about 50%, w/w, about 55% w/w, about 60% w/w, about 65% w/w, about 70% w/w, about 75% w/w, about 80% w/w, about 85% w/w, about 90% w/w, about 95% w/w, about 99% w/w, or any intermediate values therein, based on the total weight coating wt gain/membrane weight.

In certain embodiments, plasticizer is present in an amount of from about 5% w/w to about 40% w/w, from about 7.5% w/w and about 30% w/w, from about 10% w/w and about 20% w/w, and any intermediate ranges there in, based on the total weight of ethyl acrylate, methyl methacrylate, trimethylammonioethyl methacrylate chloride copolymer, to provide desired tensile strength, and elasticity for rapid expansion of the membrane. In certain embodiments, the plasticizer is present in an amount of about 5% w/w, about 6% w/w, about 7% w/w, at least 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, or any intermediate values therein, based on the total weight of the ethyl acrylate, methyl methacrylate, trimethylammonioethyl methacrylate chloride copolymer.

In certain embodiments, the membrane further includes an anti-tacking agent selected from the group comprising talc, colloidal silicon dioxide, magnesium trisilicate, powdered cellulose, starch, and tribasic calcium phosphate. In certain embodiments, the anti-tacking agent is colloidal silicon dioxide. In certain embodiments, the anti-tacking agent is present in an amount of from about 5% w/w to about 40% w/w, based on the total weight of the ethyl acrylate, methyl methacrylate, and trimethylammonioethyl methacrylate chloride copolymer. In certain embodiments, the anti-tacking agent is present in an amount of about 5% w/w, about 10% w/w, about 15% w/w, about 20% w/w, about 25% w/w, about 30% w/w, about 35% w/w, about 40% w/w, or any intermediate values therein, based on the total weight of the ethyl acrylate, methyl methacrylate, and trimethylammonioethyl methacrylate chloride copolymer.

In certain embodiments, the membrane includes at least one delivery orifice in fluid communication with the pull layer. In certain embodiments, the membrane includes two, three, four or five delivery orifices, with at least one delivery orifice in fluid communication with the pull layer. In certain embodiments, the drug is released through the orifice as a dispersion, at a desired release rate, based on the average molecular weight of the water-soluble hydrophilic polymers present in the push and the pull layer. In certain embodiments, the drug is released through the orifice and the permeable membrane at a desired release rate. In certain embodiments, the presence of an orifice in the membrane prevents membrane tearing and keeps the dosage form intact. In certain embodiments, the orifice releases excess pressure built up during swelling of the dosage form and allows the membrane to remain intact under hydrodynamic conditions of the GI tract.

6.3. Methods of Treating

In certain embodiments, the disclosure provides a method for treating hypothyroidism in a subject in need thereof, wherein the method comprises orally administering to the subject, gastroretentive thyroid hormone compositions of the disclosure. In certain embodiments, the disclosure provides a method of using gastroretentive liothyronine composition of the disclosure as a replacement therapy in primary (thyroidal), secondary (pituitary), and tertiary (hypothalamic) congenital or acquired hypothyroidism. The method comprises, orally administering to a subject in need thereof, gastroretentive thyroid hormone composition of the disclosure. In certain embodiments, the disclosure provides a method of using gastroretentive thyroid hormone composition of the disclosure as an adjunct to surgery and radiation therapy in the management of well differentiated thyroid cancer. The method comprises, orally administering to a subject in need thereof, gastroretentive thyroid hormone compositions of the disclosure. In another embodiment, the disclosure provides a method of using gastroretentive thyroid hormone composition of the disclosure as a diagnostic agent in suppression tests to differentiate suspected mild hyperthyroidism or thyroid gland autonomy. The method comprises orally administering gastroretentive thyroid hormone composition of the disclosure to a subject in need thereof. In certain embodiments, gastroretentive thyroid hormone compositions of the disclosure comprise liothyronine or a pharmaceutically acceptable salt thereof. In certain embodiments, gastroretentive thyroid hormone compositions of the disclosure include liothyronine, levothyroxine, and/or pharmaceutically acceptable salts thereof. In certain embodiments, thyroid hormone compositions of the disclosure include liothyronine or a pharmaceutically acceptable salt thereof and are administered with levothyroxine compositions. In certain embodiments, liothyronine dose for treating hypothyroidism depends on a variety of factors including: the patient's age, body weight, cardiovascular status, concomitant medical conditions (including pregnancy), concomitant medications, co-administered food, and the specific nature of the condition being treated. The dosing is individualized to account for these factors and dose adjustments made based on periodic assessment of the patient's clinical response and laboratory parameters. In certain embodiments, the recommended starting dosage is 25 µg, orally, once daily. In certain embodiments, the dosage is increased by 25 µg daily, every one or two weeks, if needed. In certain embodiments, the usual maintenance dose is 25 µg to 75 µg, e.g., 50 µg, once daily. In certain embodiments, for elderly patients with underlying cardiac disease, the staring dose can be 5 µg once daily, and increase by 5 µg increments at the recommended intervals. In certain embodiments, the serum thyroid stimulating hormone (TSH) level is not a reliable measure of dose adequacy in patients with secondary or tertiary hypothyroidism. In certain embodiments, the serum T3 level is used to monitor adequacy of therapy in patients with secondary or tertiary hypothyroidism.

The gastroretentive liothyronine compositions of the disclosure provide and maintain therapeutic plasma concentrations of liothyronine and are superior to the marketed immediate release liothyronine products. The liothyronine compositions of the disclosure provide sustained release with enhanced pharmacokinetic (PK) attributes of liothyronine, e.g., reduced burst release, reduced peak-to-trough ratios ($C_{max}/C_{min}$), reduced FI, and sustained release providing liothyronine concentrations in therapeutic range (e.g., 0.8 ng/ml-2 ng/ml), compared to marketed immediate release liothyronine products. The gastroretentive compositions of the disclosure extend the release of liothyronine in its narrow absorption window and maintain a therapeutic plasma concentration of liothyronine over an extended period of time, while mitigating or eliminating initial burst release of liothyronine. In certain embodiments, the gastroretentive compositions of the disclosure provide a FI of less than or equal to 1.

In certain embodiments, the disclosure provides a method for improving compliance in a patient with primary, secondary, or tertiary congenital or acquired hypothyroidism. The method comprises providing once-a-day oral administration of osmotic gastroretentive liothyronine composition of the disclosure to a patient in need thereof. The gastroretentive liothyronine compositions of the disclosure reduce burst release, provide a FI of less than or equal to 1, and minimize side effects such as increased heart rate, nervousness, anxiousness and irritability, and long-term side effects such as a decrease in bone density.

In certain embodiments, the disclosure provides a method for improving bioavailability of liothyronine in a patient by releasing the drug in its narrow absorption window, e.g., upper GI tract. The method comprises orally administering to the patient in need thereof, osmotic floating gastroretentive liothyronine composition of the disclosure.

6.4. Methods of Making

In certain embodiments, the disclosure provides a method for making an osmotic, gastroretentive composition containing liothyronine or a pharmaceutically acceptable salt thereof, the method comprising making a pull layer blend and a push layer blend; horizontally pressing the pull layer blend and the push layer blend into a bilayered tablet core containing a pull layer and a push layer; coating the bilayered tablet core with a permeable elastic membrane, and drilling an orifice in the permeable elastic membrane, wherein the orifice is in fluid communication with the pull layer.

In certain embodiments, the disclosure provides a method for making an osmotic, gastroretentive composition liothyronine or a pharmaceutically acceptable salt thereof, the method comprising making a pull layer blend and a push layer blend; horizontally pressing the pull layer blend and the push layer blend into a bilayered tablet core; coating the bilayered tablet core with a coating system comprising a seal coat(s), and permeable elastic membrane/functional coat. In certain embodiments, the coating system further comprises a cosmetic coat/over coat, and/or a clear coat. In certain embodiments, the bilayered tablet core is coated with various coatings in the following order: seal coat-1, functional coat/membrane, and seal coat-2. In certain embodiments, the bilayered tablet core is coated with various coatings in the following order: seal coat-1, functional coat/membrane, seal coat-2, cosmetic coat, and clear coat. In certain embodiments, the bilayered tablet core is coated with various coatings in the following order: seal coat-1, functional coat/membrane, cosmetic coat, and clear coat.

In certain embodiments, the pull layer blend comprises liothyronine or a pharmaceutically acceptable salt thereof, a swellable water-soluble polymer, an acid, and a gas-generating agent. In certain embodiments, the pull layer blend further comprises a stabilizing agent and/or an osmogen. In certain embodiments, the swellable water-soluble polymer is at least one low viscosity hydroxypropyl methylcellulose polymer (hypromellose) having a viscosity of less than or equal to 5000 cp. In certain embodiments, the swellable water-soluble polymer is at least one low viscosity hydroxypropyl methylcellulose polymer (hypromellose) having a viscosity of from about 2.3 cp to about 3.3 cp, from about 2.4 cp to about 3.6 cp, from about 4.0 cp to about 6.0 cp, from about 4.8 cp to about 7.2 cp, from about 12 cp to about 18 cp, from about 80 cp to about 120 cp, from about 2,663 cp to about 4,970 cp, or any intermediate ranges therein. In certain embodiments, the swellable water-soluble polymer is at least one high viscosity hydroxypropyl methylcellulose polymer (hypromellose) having a viscosity of from about from about 9,525 cp to about 17,780 cp, from about 13,275 cp to about 24,780 cp, from about 75,000 cp to about 140,000 cp, or any intermediate ranges therein. In certain embodiments, the swellable water-soluble polymer in the pull layer includes a mixture a low viscosity hypromellose and a high viscosity hypromellose. In certain embodiments, the weight ration of the low viscosity hypromellose and the high viscosity hypromellose is from 60:40 to 99:1. In certain embodiments, the weight ration of the low viscosity hypromellose and the high viscosity hypromellose is about 80:20, about 81:19, about 82:18, about 83:17, about 84:16, about 85:15, about 86:14, about 87:13, about 88:12, about 89:11, about 90:10, about 91:9, about 92:8, about 93:7, about 94:6, about 95:5, about 96:4, about 97:3, about 98:2, about 99:1, or any intermediate ratios therein. In certain embodiments, the high viscosity hypromellose is present in an amount of from 1% w/w to 70% w/w of the low viscosity hypromellose. In certain embodiments, the high viscosity hypromellose is present in an amount of about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, or any intermediate values therein, of the low viscosity hypromellose.

In certain embodiments, the push layer comprises at least one swellable water-soluble polymer, an osmogen, a pigment, and a lubricant. In certain embodiments, the swellable water-soluble hydrophilic polymer is polyethylene oxide polymer. In certain embodiments, the polyethylene oxide polymer has an average molecular weight of at least about 900,000 Da. In certain embodiments, the polyethylene oxide polymer has an average molecular weight of about 900,000 Da, about 1000,000 Da, about 2000,000 Da, about 3000,000 Da, about 4000,000 Da, about 5000,000 Da, about 6000,000 Da, about 7000,000 Da, or any intermediate values therein.

In certain embodiments, the seal coat(s) comprises OPADRY® II, clear; the functional coat comprises copolymer of ethyl acrylate, methyl methacrylate, and trimethylammonioethyl methacrylate chloride; the cosmetic coat comprises OPADRY® II, Pink/Green/Blue; and the final clear coat comprises OPADRY® EZ, clear. In certain embodiments, the functional coat comprises a copolymer of ethyl acrylate, methyl methacrylate, and trimethylammonioethyl methacrylate chloride ((1:2:0.2) EUDRAGIT® RL copolymer). In certain embodiments, the functional coat comprises a copolymer of ethyl acrylate, methyl methacrylate, and trimethylammonioethyl methacrylate chloride ((1:2:0.1) EUDRAGIT® RS copolymer). In certain embodiments, cosmetic coat and final clear coat are optional.

In certain embodiments, the coating system can include at least one orifice. In certain embodiments, the orifice is drilled manually or is drilled with a laser. In certain embodiments, the cosmetic coat and the clear coat do not include any orifice. In certain embodiments, the at least one orifice in the coating system is in fluid continuation with the pull layer.

In certain embodiments, the pull layer is a pull layer blend. In certain embodiments, the pull layer blend comprises Drug Intermediate and an extragranular component. In certain embodiments, the Drug Intermediate is a Drug intermediate blend containing liothyronine or a pharmaceutically acceptable salt thereof. In certain embodiments, the Drug Intermediate is Drug Intermediate granules comprising liothyronine or a pharmaceutically acceptable salt thereof. In certain embodiments, intermediate drug granules are made via dry granulation or wet granulation. In certain embodiments, Drug Intermediate comprises Drug Intermediate granules made via wet granulation. In certain embodiments, solvent used in wet granulation process comprises ethanol 200 proof, isopropyl alcohol (99% v/v), water, or a mixture thereof. In certain embodiments, the solvent used in wet granulation process does not include water. In certain embodiments, Drug Intermediate comprises Drug Intermediate granules made via dry granulation. In certain embodiments, dry granulation comprises roller compaction or slugging. In certain embodiments, the Drug Intermediate is a Drug Intermediate blend comprising a dry mix/dry mix blend of liothyronine or a pharmaceutically acceptable salt thereof and various excipients.

In certain embodiments, the extragranular components comprise at least one gas-generating agent and at least one acid. In certain embodiments, the gas generating agent is selected from the group comprising carbonate and/or bicarbonate salts of alkali or alkaline earth metals. In certain embodiments, the gas-generating agent(s) is present in intermediate drug granules and/or an extragranular portion. In certain embodiments, the at least one acid is an organic acid selected from the group comprising succinic acid, citric acid, acetic acid, malic acid, stearic acid, benzoic acid, tartaric acid, boric acid, and mixtures thereof. In certain embodiments, the extragranular excipients can further include a filler, a glidant, and/or a lubricant.

6.5. Features of the Dosage Form

The present disclosure provides osmotic gastroretentive compositions (compositions of the disclosure/liothyronine compositions/compositions) comprising liothyronine or a pharmaceutically acceptable salt thereof (liothyronine/pharmaceutically acceptable salt of liothyronine). In certain embodiments, the compositions provide therapeutically effective amount of liothyronine, independent of initial concentration of the drug. In certain embodiments, the release of liothyronine is independent of various physiological factors within the GI tract. The compositions expand rapidly, independent of the physiological conditions in the GI tract, and can be retained in the stomach for extended periods of time, e.g., at least about 4 hours, e.g., from about 6 hour to about 20 hours by maintaining the integrity of the composition in a swollen state. The osmotic gastroretentive compositions of the disclosure provide extended release, with steady plasma concentration and minimal pharmacokinetic variability, of liothyronine.

In certain embodiments, the osmotic gastroretentive compositions of the disclosure, in gastric fluid or simulated gastric fluid, swell to a size that prevents their passage through the pyloric sphincter, and the membrane maintains the integrity of the compositions in a swollen state for prolonged periods, notwithstanding hydrodynamic conditions and pH variations. In certain embodiments, the gastroretentive compositions of the disclosure provide sustained release of liothyronine from about 6 hours to about 20 hours. In certain embodiments, the compositions of the disclosure provide plasma concentration of less than 3 ng/ml (e.g., from about 0.5 ng/ml to about 3 ng/ml) of liothyronine or a pharmaceutically acceptable salt thereof, from about 6 hours to about 24 hours. In certain embodiments, the gastroretentive compositions of the disclosure remain in the swollen state for at least about 4 hours, e.g., from about 6 hours to about 24 hours. Furthermore, as the pull layer containing the active pharmaceutical agent (e.g., T3 or a pharmaceutically acceptable salt thereof) is released from the orifice and the push layer continues to swell, the dosage form becomes sufficiently empty, e.g., when at least about 80% of the T3 or a pharmaceutically acceptable salt thereof is released, and finally collapses for complete emptying from the system. In certain embodiments, the dosage form becomes sufficiently empty after at least about 60%, e.g., from about 65% to about 100%, e.g., at least about 80%, of the T3 or a pharmaceutically acceptable salt thereof is released. In certain embodiments, the osmotic gastroretentive compositions of the disclosure regulate core swelling and membrane elasticity as a function of time to enable emptying of the gastroretentive composition from the stomach.

In certain embodiments, each of the pull layer and the push layer contain at least one swellable water-soluble hydrophilic polymer/swellable water soluble polymer to provide controlled drug release. In certain embodiments, the swellable water-soluble polymer in the pull layer is selected from the group comprising hydroxypropyl methylcellulose, sodium carboxymethyl cellulose, carbomers, or any mixtures thereof. In certain embodiments, the water-soluble hydrophilic polymer in the push layer is a polyethylene oxide polymer. In certain embodiments, the polyethylene oxide polymer in the push layer has an average molecular weight of greater than or equal to about 900,000 Da.

In certain embodiments, release (e.g., released amount and release rate) of liothyronine, or a pharmaceutically acceptable salt thereof, from the composition depends upon the viscosity of the swellable water-soluble polymer in the pull layer. In certain embodiments, the viscosity of swellable water-soluble polymer in the pull layer affects viscosity of pull layer. In certain embodiments, viscosity of swellable water-soluble polymer depends upon the average molecular weight/molecular weight of the polymer. In certain embodiments, an increase in the average molecular weight of polyethylene oxide polymer in the push layer increases the swelling volume of the polyethylene oxide polymer with imbibition of water. In certain embodiments, swelling rate of swellable water-soluble polymer in the push layer decreases with increase in molecular weight of the polymer. In certain embodiments, an increase in the average molecular weight of the polyethylene oxide polymer in the push layer increases the release of the drug (e.g., T3 or a pharmaceutically acceptable salt thereof) from the pull layer. In certain embodiments, the pull layer includes a mixture of at least two different hydroxypropyl methylcellulose polymers. In certain embodiments, the swellable water-soluble polymers in the pull layer and the push layer of the tablet core; and the permeable elastic membrane over the tablet core, containing an orifice in fluid continuity with the pull layer, control the release of liothyronine, or a pharmaceutically acceptable salt thereof, for extended periods of time.

In certain embodiments, the gastroretentive compositions of the disclosure contain at least one osmogen for providing a concentration gradient to facilitate osmotic flow of gastric fluid into the composition. In certain embodiments, the osmogen is present in the push layer. In certain embodiments, the osmogen is present in the pull layer and the push layer.

In certain embodiments, the gastroretentive compositions of the disclosure exhibit a floating lag time of less than about 180 minutes, less than about 170 minutes, less than about 160 minutes, less than about 155 minutes, less than about 150 minutes, less than about 145 minutes, less than about 140 minutes, less than about 135 minutes, less than about 130 minutes, less than about 120 minutes, less than about 115 minutes, less than about 110 minutes, less than about 100 minutes, less than about 95 minutes less, than about 90 minutes, less than about 85 minutes, less than about 80 minutes, less than about 75 minutes, less than about 70 minute, less than about 65 minutes, less than about 60 minutes, less than about 55 minutes, less than about 50 minutes, less than about 45 minutes, less than about 40 minutes, less than about 35 minutes, less than about 30 minutes, less than about 25 minutes, or any intermediate time periods therein, in 200 ml dissolution medium comprising 0.001N HCl and 50 mM NaCl, measured using rotating bottle method, at 5 rpm and 37° C. In certain embodiments, gastroretentive compositions of the disclosure exhibit at least 100% volume gain on floatation, measured in 200 ml dissolution medium comprising 0.001N HCl and 80 mM NaCl, using r at 5 rpm and 37° C. In certain embodiments, the gastroretentive compositions of the disclosure exhibit a floating lag time of less than about 120 minutes in 200 ml dissolution medium comprising 0.001N HCl and 80 mM NaCl, measured using rotating bottle method, at 5 rpm and 37° C. In certain embodiments, the gastroretentive compositions of the disclosure exhibit a floating lag time of less than about 120 minutes in 200 ml dissolution medium comprising 0.001N HCl and 100 mM NaCl, measured using rotating bottle method, at 5 rpm and 37° C. In certain embodiments, the gastroretentive compositions of the disclosure exhibit a floating lag time of less than about 180 minutes in 200 ml dissolution medium comprising 0.001N HCl and 150 mM NaCl, measured using rotating bottle method, at 5 rpm and 37° C. In certain embodiments, the gastroretentive compositions of the disclosure exhibit a floating lag time of less than about 180 minutes in 200 ml dissolution medium comprising 0.001N HCl and 180 mM NaCl, measured using rotating bottle method, at 5 rpm and 37° C.

In certain embodiments, the gastroretentive compositions of the disclosure exhibit a floating lag time of less than about 180 minutes, less than about 175 minutes, less than about 170 minutes, less than about 165 minutes, less than about 160 minutes, less than about 155 minutes, less than about 150 minutes, less than about 145 minutes, less than about 140 minutes, less than about 135 minutes, less than about 130 minutes, less than about 120 minutes, less than about 115 minutes, less than about 110 minutes, less than about 100 minutes, less than about 95 minutes less, than about 90 minutes, less than about 85 minutes, less than about 80 minutes, less than about 75 minutes, less than about 70 minute, less than about 65 minutes, less than about 60 minutes, less than about 55 minutes, less than about 50 minutes, less than about 45 minutes, less than about 40 minutes, less than about 35 minutes, less than about 30 minutes, less than about 25 minutes, or any intermediate time periods therein, in 200 ml dissolution medium comprising pH 4.5 acetate buffer, measured using rotating bottle method, at 5 rpm and 37° C. In certain embodiments, the osmotic gastroretentive compositions of the disclosure exhibit a floating lag time of from about 30 minutes to about 180 minutes in GI fluids. In certain embodiments, the floating lag time is independent of the pH of the dissolution medium.

In certain embodiments, the gastroretentive compositions of the disclosure, when in contact with gastric fluid, or with media that simulate gastric conditions, expand in less than 180 minutes to a size that prevents their passage through the pyloric sphincter of a human, and exhibit a floating lag time of less than 180 minutes.

In certain embodiments, shape and size of the tablet prevents its passage through the pyloric sphincter with at least 100% increase in tablet volume, from its initial volume on coming in contact with gastric fluid.

In certain embodiments, the dosage forms of the disclosure comprise multilayered tablets that are compressed horizontally into oval, modified oval, or capsule shapes for easy swallowing. In certain embodiments, the tablets are compressed using oval-, modified oval-, capsule-shaped or any other shaping tool. In certain embodiments, the horizontally compressed multilayered tablets comprise a major axis having a length of between about 12 mm and about 24 mm, and a minor axis having a length of between about 8 mm and about 16 mm. In certain embodiments, the multilayered tablets have a major axis of about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, or any intermediate lengths therein. In certain embodiments, the multilayered tablets have a minor axis of about 8 mm, about 9 mm, about 10 mm, about 11 mm, 12 mm, about 13 mm, about 14 mm, about 15 mm, about 16 mm, or any intermediate lengths therein. In certain embodiments, the horizontally compressed multilayered tablets comprise a major axis having a length of about 20±2 mm, and a minor axis having a length of between about 10±2 mm.

In certain embodiments, the initial tablet size (e.g., 19 mm×10 mm) is reasonably small for swallowability, and once swallowed, the tablet is designed for rapid generation of carbon dioxide ($CO_2$) within the core to increase buoyancy. Within 120 minutes of coming into contact with simulated gastric medium, the tablet starts floating and transforms into an oblong shape with major and minor axis having lengths of at least about 26 mm and about 18 mm respectively, which is maintained for at least about 6 hours, e.g., at least about 12 hours. Once the dosage form achieves the constant size, the push-pull system gets activated and drug is released at a controlled rate for at least about 6 hours, e.g., from about 16-24 hours.

The gastroretentive compositions of the disclosure markedly improve absorption and bioavailability of liothyronine or a pharmaceutically acceptable salt thereof due to their ability to withstand peristalsis and mechanical contractility of the stomach (shear, or shear effect), and consequently the compositions release the drug in a sustained manner in the vicinity of their absorption site(s) and without premature transit into nonabsorbing regions of the GI tract. Unlike other formulations in the art that require a high calorie and high fat diet for maintaining gastric retention for about 6 hours, the gastroretentive compositions of the disclosure provide gastric retention of the active pharmaceutical agents with NAW, e.g., liothyronine, for at least about 8 hours, e.g., at least about 16 hours, without premature transit into nonabsorbing regions of the GI tract, under low or medium calorie diet conditions. In certain embodiments, the presence of an orifice in the membrane and Tg of from 50° C. to 65° C. of the copolymer present in the membrane, prevents membrane tearing and keeps the dosage form intact for extended periods. The orifice releases excess pressure built up during swelling of the dosage form, e.g., swelling of the push layer, and allows the membrane to remain intact until at least about 80% of the drug is released. In certain embodiments, the composition provides controlled release of liothyronine or a pharmaceutically acceptable salt thereof through the orifice and through diffusion across the permeable elastic membrane comprising a permeable copolymer of ethyl acrylate, methyl methacrylate, and trimethylammonioethyl methacrylate chloride.

In certain embodiments, the gastroretentive compositions of the disclosure provide gastric retention for up to about 6, 7, 8, 9, 10, 11, 12, 13, 14, 15, 16, 17, 18, 19, 20, 21, 22, 23, or 24 hours, or any intermediate periods therein.

In certain embodiments, membrane permeability affects floating lag time and floating time of the composition. In certain embodiments, permeation of gastric fluid into the dosage form, and generation of $CO_2$ from the gas-generating agent, increases with increasing membrane permeability. In certain embodiments, floating lag time decreases with increasing membrane permeability. In certain embodiments, floating time increases with increasing membrane permeability. In certain embodiments the membrane comprises at least one copolymer of ethyl acrylate, methyl methacrylate, and trimethylammonioethyl methacrylate chloride (e.g., EUDRAGIT® RL and EUDRAGIT® RS copolymers).

In certain embodiments, the osmotic gastroretentive compositions of the disclosure exhibit a breaking strength of ≥15N, measured using TA.XTplus apparatus. In certain embodiments, the gastroretentive compositions of the disclosure exhibit a breaking strength of ≥15N, ≥20N, ≥25N, ≥30N, ≥35N, ≥40N, ≥4N, ≥50N, ≥55N, ≥60N, or ≥65N.

In certain embodiments, the gastroretentive compositions of the disclosure are suitable for once or twice daily administration. In certain embodiments, the gastroretentive compositions of the disclosure provide sustained release of liothyronine, or a pharmaceutically acceptable salt thereof, for at least about 6 hours, e.g., from about 6 hours to about 20 hours.

In certain embodiments, the gastroretentive dosage forms of the disclosure include a rapidly expanding membrane with high tensile strength and elasticity that expands the dosage form, on coming in contact with a dissolution medium, to provide at least 100% volume gain, based on the original volume of the dosage form at time of contact with the dissolution medium, in about 180 minutes (or less), e.g., about 120 minutes; and a multilayer tablet core, comprising at least one water-soluble hydrophilic polymer, which upon imbibition and absorption of fluid, provides a controlled sustain release of the drug.

As noted above, in certain embodiments, the multilayer tablet core comprises gas-generating agents, e.g., carbonate and bicarbonate salts, that generate $CO_2$ in an acidic environment, e.g., gastric fluid. In certain embodiments, the multilayer tablet core further comprises organic acid(s) that reacts with carbonate/bicarbonate salts in an aqueous environment, e.g., independent of stomach pH, and generate $CO_2$ gas. In certain embodiments, the membrane is highly elastic/flexible due to the presence of a flexible copolymer of ethyl acrylate, methyl methacrylate, and trimethylammonioethyl methacrylate chloride having a glass transition temperature of between 50° C. and 65° C. and at least one plasticizer. The membrane expands rapidly with an outward pressure on the membrane from the generated $CO_2$ gas. In certain embodiments, the dosage form of the disclosure exhibits at least about 100% volume gain in about 180 minutes or less minutes, in about 200 ml of pH 4.5 acetate buffer, measured using rotating bottle method, at, at 5 rpm and 37° C. The membrane expands rapidly with an outward pressure on the membrane from the generated $CO_2$ gas. In certain embodiments, the dosage form of the disclosure exhibits at least about 100% volume gain in about 180 minutes or less minutes, in about 200 ml of dissolution medium comprising 0.001N HCl and 80 mM NaCl, measured using rotating bottle method, at, at 5 rpm and 37° C. In certain embodiments, the tablet core swells such that the pull layer in the swollen core is facing the orifice in the expanded membrane and provides drug release through the orifice. In certain embodiments, the membrane expansion is responsible for an initial rapid expansion of the dosage form and the swellable multilayer tablet core within the membrane supports the expanded membrane. In certain embodiments, the composition provides controlled release of liothyronine or a pharmaceutically acceptable salt thereof through the orifice and through diffusion across the permeable elastic membrane comprising a permeable copolymer of ethyl acrylate, methyl methacrylate, and trimethylammonioethyl methacrylate chloride.

In certain embodiments, the multilayer tablet core swells to a size that can support the expanded permeable elastic membrane. In certain embodiments, the permeable elastic membrane containing an orifice keeps the multilayer tablet core intact in a swollen condition for prolonged time periods and the dosage provides sustained release of the drug for prolonged time periods, e.g., from about 6 hours to about 20 hours. In certain embodiments, the rate of generation of $CO_2$ and the rate of expansion of the membrane are enhanced with increasing membrane permeability and/or increasing the amount of osmogen in the pull layer. In certain embodiments, expansion of the membrane is faster than swelling of the tablet core.

The gastroretentive compositions of the disclosure can conveniently release liothyronine, or a pharmaceutically acceptable salt thereof, within a narrow absorption window, without losing its bioavailability, in a sustained release profile.

7. EXAMPLES

Example 1: Preparation of Bilayered Sustained Release Liothyronine Sodium Tablets (50 Mcg of Liothyronine Equivalent)

The present Example provides a summary of the preparation of Tablets 1-4 as shown in Table 1. Tablets 1-4 contained METHOCEL™ K3 Premium LV and METHOCEL™ K15M Premium CR, in pull layer; Tablets 1, 3, and 4 contained and POLYOX™ WSR N-60K in push layer; and Tablet 2 contained POLYOX™ WSR Coagulant in push layer. Tablet 4 did not contain calcium sulfate dihydrate. The tablet cores were coated with a permeable functional coat comprising EUDRAGIT® RL copolymer.

TABLE 1

| Ingredients | Tablet 1 (mg) | Tablet 2 (mg) | Tablet 3 (mg) | Tablet 4 (mg) |
|---|---|---|---|---|
| Drug Intermediate | | | | |
| Liothyronine Sodium | 0.052 | 0.052 | 0.052 | 0.052 |
| Calcium Sulfate Dihydrate, NF | 84.85 | 84.85 | 84.25 | |
| Hypromellose, METHOCEL K3LV | | | | 231.25 |
| Sucrose, NF | 15.0 | 15.0 | 15.0 | |
| Butylated Hydroxytoluene | | | 0.7 | 0.7 |
| Vitamin E USP (dl-α-tocopherol) | 0.10 | 0.10 | | |
| Colloidal Silicone Dioxide | | | | 2.0 |
| Total Weight | 100 | 100 | 100 | 234 |
| Pull layer Blend | | | | |
| Drug Intermediate | 100.0 | 100.0 | 100.0 | 234.0 |
| Sodium Bicarbonate, USP | 50.0 | 50.0 | 50.0 | 50.0 |
| Calcium Carbonate, USP | 75.0 | 75.0 | 75.0 | 75.0 |
| Sucrose | 285.0 | 285.0 | 285.0 | 300.0 |
| Hypromellose, USP (METHOCEL ™ K3 Premium LV) | 231.5 | 231.5 | 231.5 | |
| Hypromellose, NF (METHOCEL ™ K15M Premium CR) | 5.00 | 5.00 | 5.0 | 5.0 |
| Succinic Acid, NF (Micronized) | 125.0 | 125.0 | 125.0 | 125.0 |
| Colloidal Silicon Dioxide, NF (CAB-O-SIL ® M5P) | 3.5 | 3.5 | 8.5 | 6.0 |
| Magnesium Stearate, NF | 10.0 | 10.0 | 10.0 | 10.0 |
| Total Weight of Pull Layer | 885 | 885 | 890 | 805 |
| Push-Layer Blend | | | | |
| Polyethylene Oxide, NF (POLYOX ™ WSR Coagulant) | — | 132.0 | | |
| Polyethylene Oxide, NF (POLYOX ™ WSR N-60K) | 220.0 | | 220.0 | 220.0 |
| Sodium Chloride, USP | 25.0 | 15.0 | 25.0 | 25.0 |
| Red Pigment Blend (PB-1595) | 2.0 | 1.2 | 2.0 | 2.0 |
| Magnesium Stearate, NF | 3.0 | 1.80 | 3.0 | 3.0 |
| Total Weight of Push Layer | 250 | 150 | 250 | 250 |
| Total Core Weight | 1135 | 1035 | 1140 | 1055 |
| Seal Coat-1 | | | | |
| OPADRY ® II Clear | 30.0 | 30.0 | 30.0 | 30.0 |
| Total Weight of Seal Coated Core | 1165 | 1065 | 1170 | 1085 |
| Functional Coat | | | | |
| EUDRAGIT ® RL | 148.20 | 148.20 | 148.2 | 92.63 |
| Triethyl Citrate | 22.20 | 22.20 | 22.20 | 13.88 |

TABLE 1-continued

| Ingredients | Tablet 1 (mg) | Tablet 2 (mg) | Tablet 3 (mg) | Tablet 4 (mg) |
|---|---|---|---|---|
| Talc | 29.60 | 29.60 | 29.60 | 18.50 |
| Total Weight of Functional Coat | 200 | 200 | 200 | 125 |
| Total Weight | 1365 | 1265 | 1370 | 1210 |
| Seal Coat-2 | | | | |
| OPADRY® II Clear | 10.0 | 10.0 | 10.0 | 10.0 |
| Total Tablet Weight | 1375 | 1275 | 1380 | 1220 |

*Removed during process

Manufacturing Procedure:

A. Pull Layer Blend:

Wet Granulation Method: Liothyronine sodium, calcium sulfate dihydrate, sucrose (a portion of the total sucrose), vitamin E/BHT were granulated, as per Tablets 1-3, into Drug Intermediate Granules. Similarly, as per Tablet 4, liothyronine sodium, hypromellose (METHOCEL K3 LV), colloidal silicon dioxide, and BHT were wet granulated into Drug Intermediate granules. The granules, as per Tablets 1-4, were milled and blended with sodium bicarbonate, calcium carbonate, sucrose (remaining portion for Tablets 1-3), hypromellose (METHOCEL K15M Premium CR and METHOCEL K3 LV mixture for Tablets 1-3 and METHOCEL K15M Premium CR for Tablet 4), succinic acid, colloidal silicon dioxide, and magnesium stearate to obtain a pull layer blend.

Dry Blend Method: Liothyronine sodium, calcium sulfate dihydrate, sucrose (a portion of the total sucrose), vitamin E/BHT were dry blended using an acoustic mixer, as per Tablets 1-3, into a Drug Intermediate blend. Similarly, as per Tablet 4, liothyronine sodium, hypromellose (METHOCEL K3 LV), colloidal silicon dioxide, and BHT were dry blended using an acoustic mixer into a Drug Intermediate blend. The Drug Intermediate Blend, as per Tablets 1-4, was further blended with sodium bicarbonate, calcium carbonate, sucrose (remaining portion for Tablets 1-3), hypromellose (METHOCEL K15M Premium CR and METHOCEL K3 LV mixture for Tablets 1-3 and METHOCEL K15M Premium CR for Tablet 4), succinic acid, colloidal silicon dioxide, and magnesium stearate to obtain a pull layer blend.

B. Push Layer Blend:

POLYOX™ WSR N-60K (Tablets 1, 3, and 4), POLYOX™ WSR Coagulant (Tablet 2), sodium chloride, Red Pigment Blend (PB-1595), and magnesium stearate were blended into a uniform push layer blend.

C. Bilayered Tablet Core:

The pull layer blend from Step A and the push layer blend from Step B were pressed horizontally, using a suitable tablet press, into a bilayered tablet core.

D. Seal Coat-1, Functional Coat, and Seal Coat-2

Bilayered tablet cores from Step C were coated with Seal coat-1, Functional Coat over Seal Coat-1, and Seal Coat-2 over Functional Coat, using a perforated pan coater. Seal Coat-land Seal Coat-2 contained OPADRY® II clear, and Functional Coat contained EUDRAGIT® RL copolymer, triethyl citrate, and talc.

Example 2: Effect of Polyethylene Oxide Polymer on Stability of Liothyronine Sodium The present Example compares storage stability of single layered tablets containing liothyronine sodium granules blended with polymers as per Table 2 (e.g., Tablet 5 contained POLYOX™ WSR N80 and POLYOX™ WSR 303; Tablet 6 contained sodium carboxy methylcellulose; Tablet 7 contained METHOCEL™ K100 Premium LV; and Tablet 8 contained PEO 1NF and PEO 18NF, and Tablet 9 contained hypromellose).

TABLE 2

| Ingredients | Tablet 5 (mg) | Tablet 6 (mg) | Tablet 7 (mg) | Tablet 8 (mg) | Tablet 9 (mg) |
|---|---|---|---|---|---|
| Drug Intermediate | | | | | |
| Liothyronine Sodium | 0.052 | 0.052 | 0.052 | 0.052 | 0.052 |
| Calcium Sulfate Dihydrate, NF | 84.85 | 84.85 | 84.95 | 84.85 | 84.95 |
| Sucrose, NF | 15.0 | 15.0 | 15.0 | 15.0 | 15.0 |
| Vitamin E USP (dl-α-tocopherol) | 0.10 | 0.10 | 0.00 | 0.10 | — |
| Total Weight | 100 | 100 | 100 | 100 | 100 |
| Pull Layer Blend | | | | | |
| Drug Intermediate | 100 | 100 | 100 | 100 | 100 |
| Sodium Bicarbonate, USP | 50.0 | 50.0 | 50.0 | 50.0 | 50.0 |
| Calcium Carbonate, USP | 125.0 | 125.0 | 125.0 | 75.0 | 125.0 |
| Succinic Acid, NF (Micronized) | 125.0 | 125.0 | 125.0 | 125.0 | 125.0 |
| Colloidal Silicon Dioxide, NF (CAB-O-SIL® MSP) | 3.5 | 3.5 | 3.5 | 3.5 | 3.5 |
| Magnesium Stearate, NF | 10.0 | 10.0 | 10.0 | 10.0 | 10.0 |
| Mannitol, USP (PARTECK® M200) | 81.50 | 81.50 | 81.50 | 79.50 | 81.50 |
| Polyethylene Oxide, NF (POLYOX™ WSR N-80K) | 200.0 | — | — | — | — |
| Polyethylene Oxide, NF (POLYOX™ WSR 303) | 5.0 | — | — | — | — |
| Polyethylene Oxide, NF (PEO-1NF)) | — | — | — | 250.0 | — |

TABLE 2-continued

| Ingredients | Tablet 5 (mg) | Tablet 6 (mg) | Tablet 7 (mg) | Tablet 8 (mg) | Tablet 9 (mg) |
|---|---|---|---|---|---|
| Polyethylene Oxide, NF (PEO-18NF)) | — | — | — | 7.0 | — |
| Sodium CMC (AQUALON 7L2P) | — | 200.00 | — | — | — |
| Sodium CMC (AQUALON ™ 7H4F M) | — | 5.0 | — | — | — |
| Hypromellose (METHOCEL ™ K100 Premium LV) | | | 205.0 | | 205.0 |
| Total Weight of Pull Layer | 700 | 700 | 700 | 700 | 700 |

TABLE 3

| | | % Impurities | | |
|---|---|---|---|---|
| | | 40° C./75% Relative Humidity | | 30° C./65% Relative Humidity |
| Tablet No. | Initial (Room Temperature) | 1 week | 1 Month | 2 Month |
| Tablet 5 | 0.2 | 9.8 | — | — |
| Tablet 6 | 0.9 | 0.4 | — | — |
| Tablet 7 | 4.3 | 5.2 | — | — |
| Tablet 8 | 0.3 | 21.3 | — | — |
| Tablet 9 | 0.592 | — | 0.564 | 0.328 |

Core tablets with pull layer alone (Tablets 5-9) were prepared to evaluate stability of liothyronine in different POLYOX® grades and in alternate hydrophilic polymers. The tablets with pull layer alone were made according to the procedure for making pull layer in Example 1. Liothyronine sodium, calcium sulfate dihydrate, vitamin E (Tablets 5-8), and sucrose were granulated into liothyronine granules. The liothyronine granules were milled and blended with sodium bicarbonate, calcium carbonate, sucrose, succinic acid, colloidal silicon dioxide, magnesium stearate, and additional polymers as per Table 2 (e.g., Tablet 5 contained POLYOX™WSR N80 and POLYOX™ WSR 303; Tablet 6 contained sodium carboxy methylcellulose; Tablets 7 and 9 contained METHOCEL™ K100 Premium LV. Tablet 8 contained PEO 1NF and PEO 18NF) to obtain a pull layer blend. Tablets 5-8 were placed on one-week stability at 45° C./75% RH. Stability of the tablets was evaluated as % assay at the end of the storage period. Tablet 9 was placed on one month stability at 45° C./75% RH, and on two-month stability at 30° C./65% RH. Stability of the tablets was evaluated as % assay at the end of the storage period.

As seen in Table 3, the stability of liothyronine tablets improved significantly by replacing polyethylene oxide polymer with hypromellose or sodium carboxymethyl cellulose. The single layered tablets containing liothyronine sodium and polyethylene oxide polymer (Tablet 5), showed reduced % assay even after one-week storage at 40° C./75% relative humidity (accelerated storage conditions). Tablet 9 containing hypromellose showed substantially improved one month stability at 45° C./75% RH, and on two-month stability at 30° C./65% RH.

Example 3: Effect of Hypromellose on Floating Lag Time

The time required for the tablet to float in gastric medium is an important measure of the gastric retention, as rapid progression to floating reduces the chance of accidental emptying of the dosage form from the stomach. The present Example compares floating lag time of bilayered liothyronine tablets of the disclosure containing POLYOX™ (POLYOX™ WSR N80 and optionally, POLYOX™ WSR 303); tablets containing hypromellose (METHOCEL™ K3 Premium LV and METHOCEL™ K15M Premium CR); tablets containing hypromellose and sucrose; tablets containing hypromellose, sucrose, and lactose; and tablets containing hypromellose, sucrose, and POLOXAMER® in the pull layer blend. The tablets were made according to the procedure as per Example 1. Tablets were placed individually in separate glass bottles containing about 200 ml dissolution medium comprising 0.001N HCl and 10 mM NaCl; 0.001N HCl and 50 mM NaCl; 0.001N HCl and 150 mM NaCl; and in light meal media. The light meal media refers to media comprising sodium chloride, potassium chloride, potassium hydrogen phosphate, calcium chloride, citric acid, and sugar. The bottles were secured in the rotating arm of an apparatus placed inside a water bath maintained at about 37° C. The bottles were rotated at a speed of about 5 rpm. The tablets were carefully observed until they began to float on the surface of the medium. The time elapsed was recorded and reported as floating lag time. Table 4 lists floating lag times for the tablets.

TABLE 4

| | Floating Lag Time (mins) | | | |
|---|---|---|---|---|
| Composition | 0.001N HCl + 10 mM NaCl | 0.001N HCl + 50 mM NaCl | 0.001N HCl + 150 mM NaCl | Light Meal Media |
| Liothyronine tablets containing POLYOX ™ | 37 | 47 | 90 | 90 |
| Liothyronine tablets containing Hypromellose (METHOCEL ™ K3 Premium LV and | 85 | 120 | 240 | 270 |

TABLE 4-continued

| Composition | Floating Lag Time (mins) | | | |
|---|---|---|---|---|
| | 0.001N HCl + 10 mM NaCl | 0.001N HCl + 50 mM NaCl | 0.001N HCl + 150 mM NaCl | Light Meal Media |
| METHOCEL ™ K15M Premium CR) | | | | |
| Liothyronine tablets containing Hypromellose and Sucrose (200 mg) | 41-43 | 41-42 | 150-180 | 90 |
| Liothyronine tablets containing Hypromellose, Sucrose (100 mg), and Lactose (100 mg) | 83 | 88 | 220 | 140 |
| Liothyronine tablets containing Hypromellose, Sucrose (200 mg), and POLOXAMER ® (40 mg) | | 77-99 | 175-180 | 90 |

It was observed that lag time of tablets containing 200 mg sucrose was comparable to the lag time provided by the tablets containing POLYOX™. Additionally, tablets containing POLOXAMER® showed improved hydration in light meal media compared to tablets with no POLOXAMER®.

Example 4: Effect of Sucrose on Floating Lag Time

The time required for the tablet to float in gastric medium is an important measure of the gastric retention, as rapid progression to floating reduces the chance of accidental emptying of the dosage form from the stomach. The present Example compares floating lag time of bilayered liothyronine Tablets 10, 11, and 12 containing 15 mg, 95 mg, and 200 mg of sucrose, respectively. The tablets were made according to the procedure as per Example 1. Tablets 10-12 contained METHOCEL K3 LV and K15M Premium CR.

TABLE 5

| Ingredients | Tablet 10 (mg) | Tablet 11 (mg) | Tablet 12 (mg) |
|---|---|---|---|
| Drug Intermediate | | | |
| Liothyronine Sodium | 0.052 | 0.052 | 0.052 |
| Sucrose, NF | 15.0 | 95.0 | 200.0 |
| Vitamin E USP (dl-α-tocopherol) | 0.10 | 0.10 | 0.10 |
| Total Weight | 15.15 | 95.15 | 200.15 |
| Pull Layer Blend | | | |
| Drug Intermediate | 15.15 | 95.15 | 200.15 |
| Sodium Bicarbonate, USP | 50.0 | 50.0 | 50.0 |
| Calcium Carbonate, USP | 75.0 | 75.0 | 75.0 |
| Mannitol USP (PARTECK ® M200) | 116.45 | 116.45 | 116.45 |
| Hypromellose, USP (METHOCEL ™ K3 Premium LV) | 300.0 | 231.50 | 231.50 |
| Hypromellose, NF (METHOCEL ™ K15M Premium CR) | 5.0 | 5.0 | 5.0 |
| Succinic Acid, NF (Micronized) | 125.0 | 125.0 | 125.0 |
| Colloidal Silicon Dioxide, NF (CAB-O-SIL ® MSP) | 3.50 | 3.50 | 3.50 |

TABLE 5-continued

| Ingredients | Tablet 10 (mg) | Tablet 11 (mg) | Tablet 12 (mg) |
| --- | --- | --- | --- |
| Magnesium Stearate, NF | 10.0 | 10.0 | 10.0 |
| Total Pull Layer Weight | 700 | 711.60 | 816.6 |
| Push-Layer Blend | | | |
| Polyethylene Oxide, NF (POLYOX™ WSR N-60K) | 220.0 | 220.0 | 220.0 |
| Sodium Chloride, USP | 25.0 | 25.0 | 25.0 |
| Red Pigment Blend (PB-1595) | 2.0 | 2.0 | 2.0 |
| Magnesium Stearate, NF | 3.0 | 3.0 | 3.0 |
| Total Push Layer Weight | 250 | 250 | 250 |
| Total Weight | 950 | 961.6 | 1066.6 |
| Seal Coat-1 | | | |
| OPADRY® II Clear | 30.0 | 30.0 | 30.0 |
| Solvent* | Purified water | Purified water | Purified water |
| Total Weight of Seal Coated Core | 980.0 | 991.6 | 1096.6 |
| Functional Coat | | | |
| EUDRAGIT® RL | 148.20 | 148.20 | 148.20 |
| Triethyl Citrate | 22.20 | 22.20 | 22.20 |
| Talc | 29.60 | 29.60 | 29.60 |
| Solvent* | Acetone & Purified water | Acetone & Purified water | Acetone & Purified water |
| Total Functional Coat Weight | 200 | 200 | 200 |
| Total Weight | 1180 | 1191.6 | 1296.6 |
| Seal Coat-2 | | | |
| OPADRY® II Clear | 10.0 | 10.0 | 10.0 |
| Solvent* | Purified water | Purified water | Purified water |
| Total Tablet Weight | 1190 | 1201.6 | 1306.6 |

*Removed during process.

TABLE 6

| Tablet Number | Floating Lag time (minutes) |
| --- | --- |
| 10 | 120 |
| 11 | 100 |
| 12 | 83 |

The final coated tablets (Tablet 10-12) were placed individually in separate glass bottles containing about 200 ml of 0.01N HCl. The bottles were secured in the rotating arm of an apparatus placed inside a water bath maintained at about 37° C. The bottles were rotated at a speed of about 5 rpm. The tablets were carefully observed until they began to float on the surface of the medium. The time elapsed was recorded and reported as floating lag time. Table 5 lists floating lag times for Tablets 10-12.

It was observed that the amount of sucrose in the pull layer directly affected the floating lag time (tablets with higher sucrose amount floated faster with shorter lag time).

Example 5: Effect of Functional Coating Weight Gain on Floating Lag Time

The present Example compares floating lag time of bilayered liothyronine tablets containing 100 mg, 150 mg, and 200 mg functional coating weight gains, respectively. The tablets were made according to the procedure as per Example 1. Tablets were placed individually in separate glass bottles containing about 200 ml dissolution medium comprising 0.001N HCl and 50 mM NaCl; 0.001N HCl and 100 mM NaCl; and 0.001N HCl and 150 mM NaCl. The bottles were secured in the rotating arm of an apparatus placed inside a water bath maintained at about 37° C. The bottles were rotated at a speed of about 5 rpm. The tablets were carefully observed until they began to float on the surface of the medium. The time elapsed was recorded and reported as floating lag time. Table 7 lists floating lag times for the tablets with different coating weight gains.

TABLE 7

| Coating Weight Gain (mg) | Floating Lag Time | | |
|---|---|---|---|
| | 0.001N HCl + 50 mM NaCl | 0.001N HCl + 100 mM NaCl | 0.001N HCl + 150 mM NaCl |
| 100 | 42 | 80 | 145 |
| 150 | 55 | 116 | 145 |
| 200 | 65 | 145 | 190 |

It was observed that floating lag time in all dissolution media increased with increase in coating weight gain (tablets with highest coating weight gain exhibit maximum floating lag time).

Example 6: Effect of Surfactant on Stability of Liothyronine Sodium

The present Example compares storage stability of liothyronine in presence of at least one surfactant. Tablet 13 contained liothyronine sodium in presence of a surfactant, e.g., POLOXAMER 188, and Tablet 14 did not contain any surfactant. The tablets were made according to the procedure as per Example 1.

TABLE 8

| Ingredients | Tablet 13 (mg) | Tablet 14 (mg) |
|---|---|---|
| Drug Intermediate | | |
| Liothyronine Sodium | 0.052 | 0.052 |
| Sucrose, NF | 15.0 | 15.0 |
| Vitamin E USP (dl-α-tocopherol) | 0.10 | 0.10 |
| Calcium Sulfate Dihydrate, NF | 84.85 | 84.85 |
| Total Weight of Drug Intermediate | 100 | 100 |
| Pull Layer Blend | | |
| Drug Intermediate | 100 | 100 |
| Sucrose | 185.0 | 185.0 |
| Sodium Bicarbonate, USP | 50.0 | 50.0 |
| Calcium Carbonate, USP | 75.0 | 75.0 |
| POLOXAMER 188, NF | 40.0 | 0.0 |
| Hypromellose, USP (METHOCEL™ K3 Premium LV) | 231.50 | 231.50 |
| Hypromellose, NF (METHOCEL™ K15M Premium CR) | 5.0 | 5.0 |
| Succinic Acid, NF (Micronized) | 125.0 | 125.0 |
| Colloidal Silicon Dioxide, NF (CAB-O-SIL® MSP) | 3.50 | 3.50 |
| Magnesium Stearate, NF | 10.0 | 10.0 |
| Total Pull Layer Weight | 825 | 785 |
| Push-Layer Blend | | |
| Polyethylene Oxide, NF (POLYOX™ WSR N-60K) | 220.0 | 220.0 |
| Sodium Chloride, USP | 25.0 | 25.0 |
| Red Pigment Blend (PB-1595) | 2.0 | 1.80 |
| Magnesium Stearate, NF | 3.0 | 3.0 |
| Total Push layer Weight | 250.0 | 250 |
| Total Weight of tablet Core | 1075 | 1035 |
| Seal Coat-1 | | |
| OPADRY® II Clear | 30.0 | 30.0 |
| Solvent* | Purified water | Purified water |
| Total Weight of Seal Coated Core | 1105 | 1065 |
| Functional Coat | | |
| EUDRAGIT® RL | 148.2 | 148.2 |
| Triethyl Citrate | 22.2 | 22.2 |
| Talc | 29.6 | 29.6 |
| Weight of Functional Coated Tablet | 1305 | 1265 |
| Seal Coat-2 | | |
| OPADRY® II Clear | 10.0 | 10.0 |
| Total Tablet Weight | 1315 | 1275 |

TABLE 9

| Tablet No. | Storage Conditions | % Assay (after storage) | % Assay (Initial) |
|---|---|---|---|
| Tablet 13 | 1 Month/5° C. | 92.8 | 91.8 |
| | 1 Month/25° C./60% RH | 81.3 | |
| Tablet 14 | 1 Month/5° C. | 114.9 | 114.3 |
| | 1 Month/25° C./60% RH | 111.9 | |

Tablets 13 and 14 were placed on one-month stability at 5° C. and at 25° C./60% RH. Stability of the tablets was evaluated as % assay at the end of the storage period. It was observed that tablets containing surfactant (Tablet 13) showed reduction in % assay after storage at 25° C./60% RH for one month.

Example 7: Dissolution Profile of Tablet 3

Figure 3:
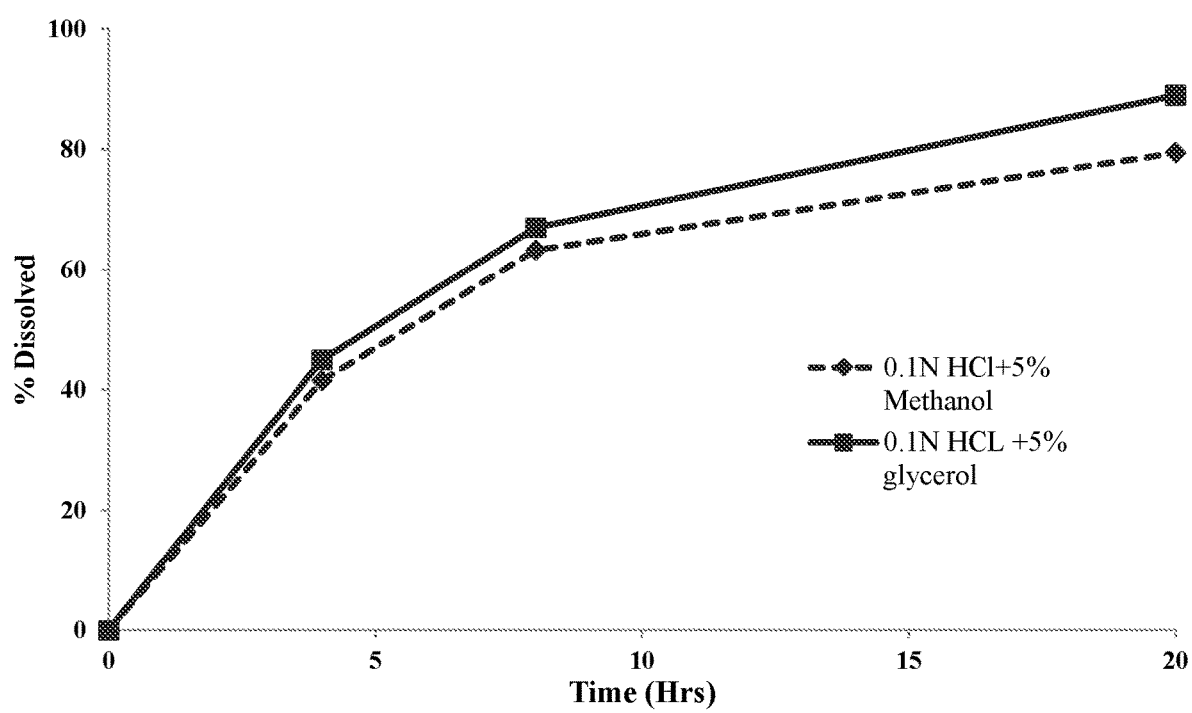

FIG. 3 compares dissolution profiles of Tablet 3, using USP Apparatus I at 37° C., in a 500 ml dissolution medium containing 0.1 N HCl and 5% methanol; and in a 500 ml dissolution medium containing 0.1N HCl and 5% glycerol. Tablet 3 contained METHOCEL K15M Premium CR and METHOCEL K3 LV mixture in the pull layer blend. It was observed that Tablet 3 provided sustained release with substantially complete drug recovery at 20 hours from the time of administration of the dosage form into the dissolution media containing 0.1N HCl and 5% glycerol.

Example 8: Comparison of Dissolution Profiles of Tablet 1 and Tablet 2

Figure 2:
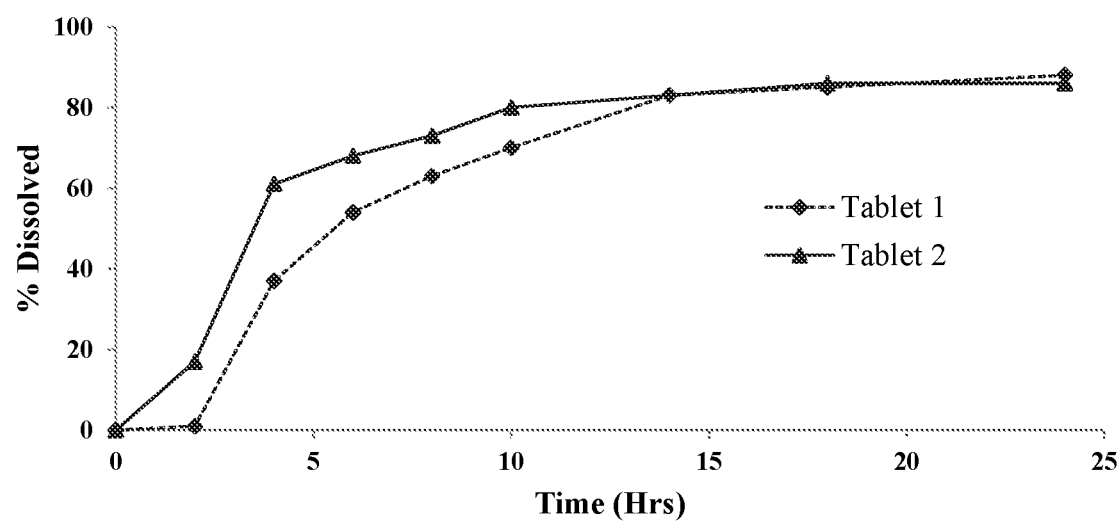

FIG. 2 compares dissolution profiles of Tablet 1 and Tablet 2, performed using USP Apparatus II at 100 RPM and 37° C., in 500 ml dissolution medium containing 0.1 N HCl and glycerol, for 24 hours. Tablet 1 contained 220 mg of POLYOX™ WSR N-60K and 25 mg of sodium chloride in the push layer and Tablet 2 contained 132 mg of (POLYOX™ WSR Coagulant and 15 mg of sodium chloride in the push layer. It was observed that the dissolution of liothyronine was faster from the tablets containing POLYOX™ WSR N-60K in the push layer.

Example 9: Volume Gain on Floatation of Tablet 3 and Tablet 4

Figure 4:
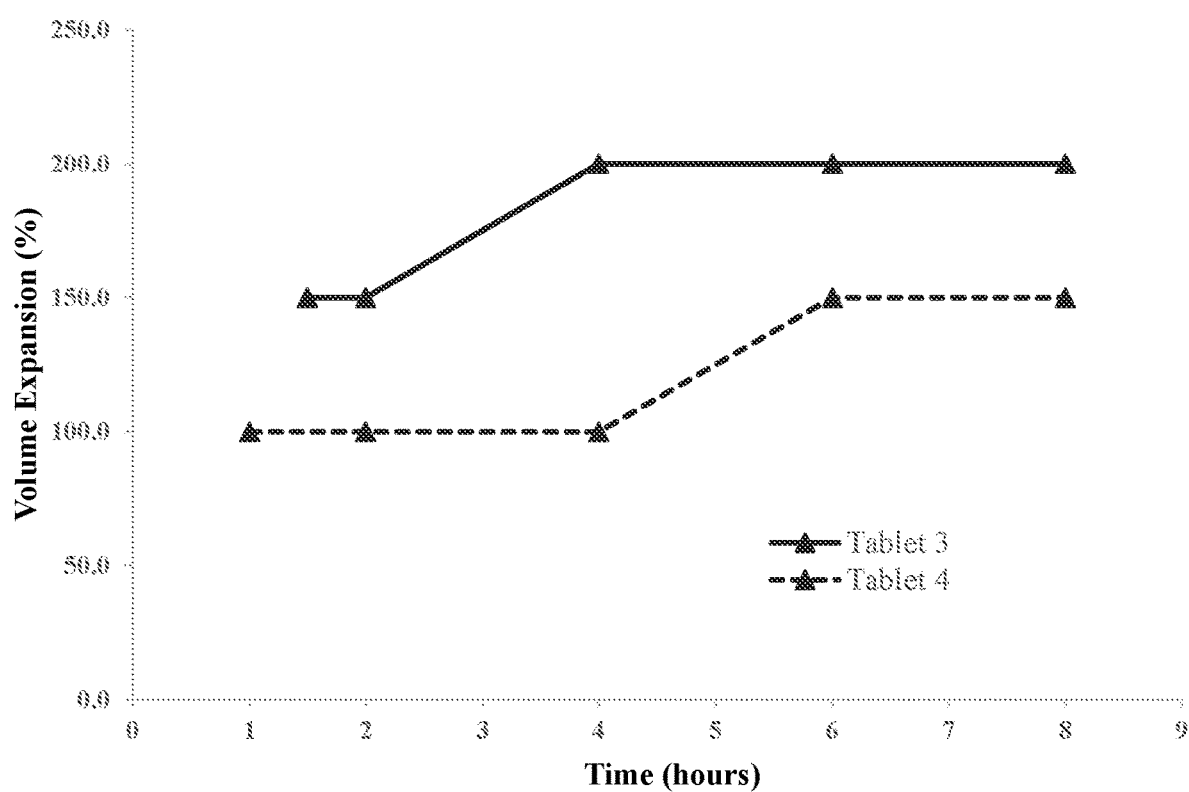

Tablets 3 and 4 were tested for volume expansion. The volume expansion studies were performed using Rotating Bottle method, at 5 rpm and 37° C., in 200 ml dissolution medium containing 0.001 N HCl and 80 mM NaCl. FIG. 4/Table 8 compares volume gain of Tablet 3 and Tablet 4, in 200 ml dissolution medium containing 0.001 N HCl and 80 mM NaCl, on floatation and at additional time points.

FIG. 4/Table 10 demonstrates that Tablet 3 showed 150% volume gain on floatation time (~90 minutes), about 150% volume gain at about two hours, 200% volume gain from about 4 hours to about 8 hours post-administration of the tablet into the dissolution medium. Similarly, Tablet 4 showed 100% volume gain at floatation time (~60 minutes), about 100% volume gain at about two hours, 150% volume gain from about 6 hours to about 8 hours post-administration of the tablet into the dissolution medium. Table 10 further shows that average floating lag time for Tablets 3 and 4 is 120 minutes or less—average floating lag time for Tablet 3 (with higher coating weight gain) is about 90 minutes and the average floating lag time for Tablet 4 (with lower coating weight gain) is about 60 minutes. FIG. 4 clearly demonstrates that Tablet 3 and Tablet 4 gained at least 100% volume in 180 minutes or less; and gained at least 100% volume on floatation.

TABLE 10

Volume Expansion upon floatation in 0.01N HCl containing 80 mM NaCl

| | Tablet 3 | | Tablet 4 | |
|---|---|---|---|---|
| Time (Hours) | % Volume Expansion | Time (mm) | % Volume Expansion | Time (mm) |
| Floating Time | 150 | 90 | 100 | 60 |
| 2 | 150 | 100 | 100 | 65 |
| 4 | 200 | 96.5 | 100 | 60 |
| 6 | 200 | 96 | 150 | 55 |
| 8 | 200 | 95 | 150 | 60 |

Example 10: Texture Analysis/Compressibility of Tablets 3 and 4

Figure 5:
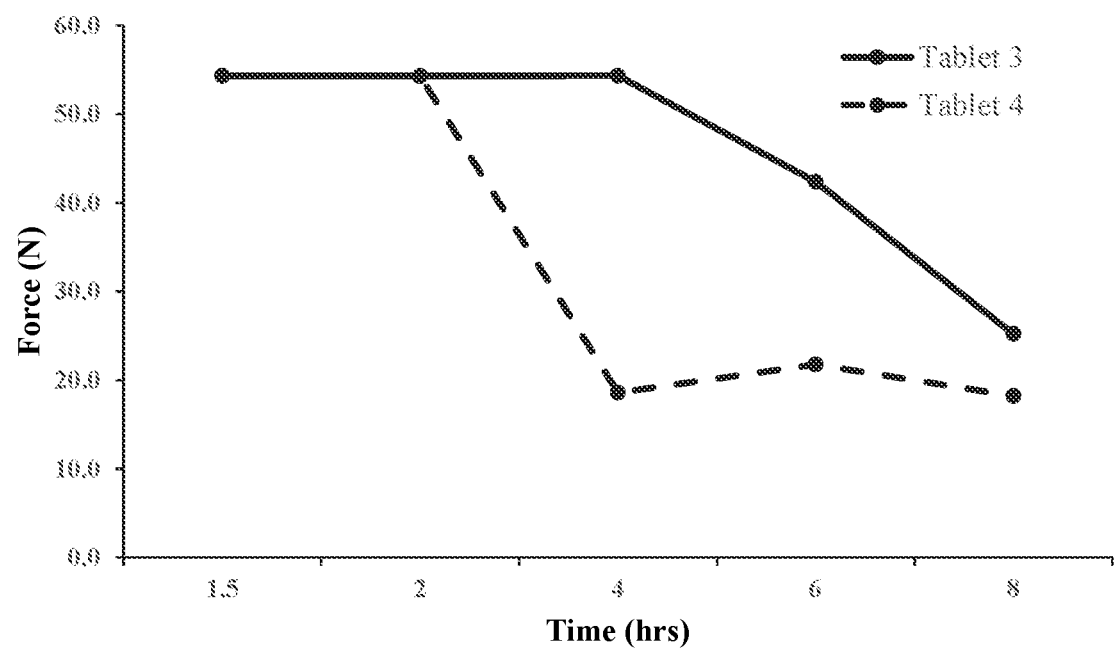
FIG. 5 shows compression force at breaking point for Tablet 3 and Tablet 4 at 1.5 hours (floatation time), 2 hours, 4 hours, 6 hours, and 8 hours, measured from the time of administration into the medium.
Figure 6:
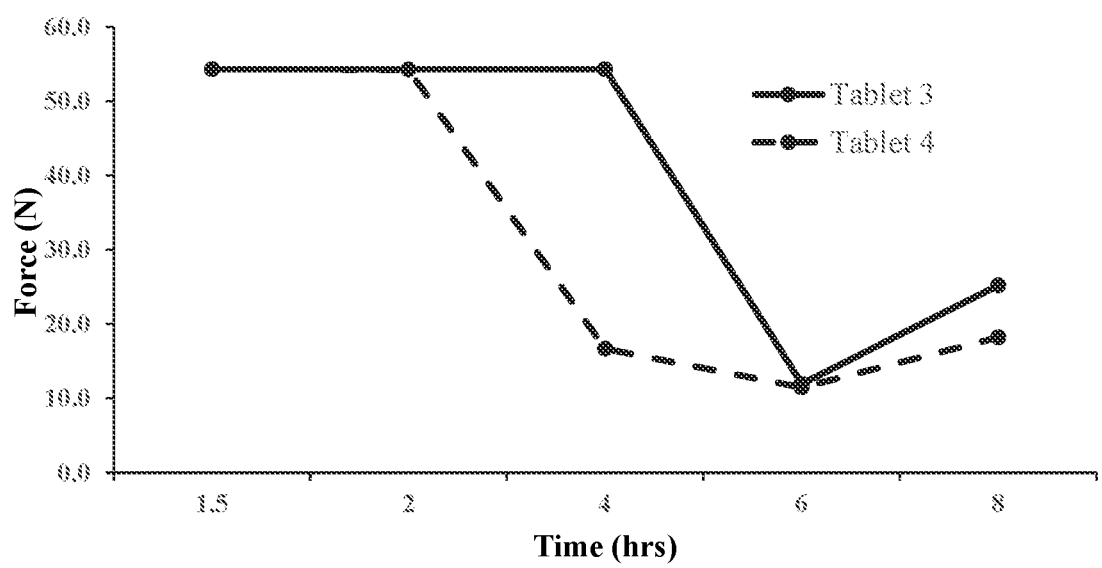
FIG. 6 shows compression force at 75% strain for Tablet 3 and Tablet 4 at 1.5 hours (floatation time), 2 hours, 4 hours, 6 hours, and 8 hours, measured from the time of administration into the medium.

Tablets 3 and 4 were tested for texture analysis/compressibility. Volume expansion studies were performed using Rotating Bottle method, at 5 rpm and 37° C., in 200 ml of 0.001 N HCl containing 80 mM NaCl, and the tablets were simultaneously tested for their texture at various time points using TA.XT$^{plus}$ apparatus. FIG. 5/Table 11 shows compression force at breaking point for Tablet 3 and Tablet 4 on floatation, and at 2 hours, 4 hours, 6 hours, and 8 hours, measured from the time of administration into the medium. FIG. 6/Table 12 shows compression force at 75% strain for Tablets 3 and 4 on floatation, and at 2 hours, 4 hours, 6 hours, and 8 hours, measured from the time of administration into the medium. FIGS. 5 and 6 demonstrate that Tablet 3 could withstand maximum force until about 4 hours from the time of administration into the dissolution medium, and Tablet 4 could withstand maximum force until about 2 hours from the time of administration into the dissolution medium. FIG. 5 further demonstrate that Tablet 3 could withstand a breaking force of at least about 20 N at about 8 hours from the time of administration into the dissolution medium.

TABLE 11

| | Force at Breaking Point (N) | |
|---|---|---|
| Time (Hours) | Tablet 3 | Tablet 4 |
| Floating Time (1 hr) | | 54.3 |
| Floating Time (1.5 hr) | 54.3 | |
| 2 | 54.3 | 54.3 |
| 4 | 54.3 | 18.6 |
| 6 | 42.4 | 21.2 |
| 8 | 25.2 | 18.2 |

TABLE 12

| | Force at 75% Strain (N) | |
|---|---|---|
| Time (Hours) | Tablet 3 | Tablet 4 |
| Floating Time (60 minutes) | | 54.3 |
| Floating Time (90 minutes) | 54.3 | |
| 2 | 54.3 | 54.3 |
| 4 | 54.3 | 16.7 |
| 6 | 13.1 | 11.5 |
| 8 | 29.4 | 18.2 |

Example 11: Impact of Average Molecular Weight of Polyethylene Oxide Polymer Present in the Push Layer on Dissolution Profiles of Tablets 15 and 16

TABLE 13

| Ingredients | Tablet 15 (mg) | Tablet 16 (mg) |
|---|---|---|
| Drug Intermediate | | |
| Liothyronine Sodium | 0.052 | 0.052 |
| Sucrose, NF | 15.0 | 15.0 |
| Vitamin E USP (dl-α-tocopherol) | 0.10 | 0.10 |
| Calcium Sulfate Dihydrate, NF | 84.85 | 84.85 |
| Total Weight | 100 | 100 |
| Pull Layer Blend | | |
| Drug Intermediate | 100 | 100 |
| Sucrose | 185.0 | 185.0 |
| Sodium Bicarbonate, USP | 50.0 | 50.0 |
| Calcium Carbonate, USP | 75.0 | 75.0 |
| Hypromellose, USP (METHOCEL ™ K3 Premium LV) | 231.50 | 231.50 |
| Hypromellose, NF (METHOCEL ™ Ki SM Premium CR) | 5.00 | 5.00 |
| Succinic Acid, NF (Micronized) | 125.0 | 125.0 |
| Colloidal Silicon Dioxide, NF (CAB-O-SIL ® MSP) | 3.50 | 3.50 |
| Magnesium Stearate, NF | 10.00 | 10.00 |
| Total Weight | 785.0 | 785.0 |
| Push-Layer Blend | | |
| Polyethylene Oxide, NF (POLYOX ™ WSR N-60K) | 220.0 | — |
| Polyethylene Oxide, NF (POLYOX ™ WSR Coagulant) | 132.0 | |
| Sodium Chloride, USP | 25.0 | 15.0 |
| Red Pigment Blend (PB-1595) | 2.0 | 1.20 |
| Magnesium Stearate, NF | 3.0 | 1.8 |
| Total Weight (Pull layer and Push Layer) | 1035 | 935 |

TABLE 13-continued

| Ingredients | Tablet 15 (mg) | Tablet 16 (mg) |
|---|---|---|
| Seal Coat-1 | | |
| OPADRY ® II Clear | 30.00 | 30.00 |
| Total weight | 1065 | 965 |
| Functional Coat | | |
| EUDRAGIT ® RL | 148.20 | 148.20 |
| Triethyl Citrate | 22.20 | 22.20 |
| Talc | 29.60 | 29.60 |
| Weight of Functional Coated Tablet | 1265 | 1165 |
| Seal Coat-2 | | |
| OPADRY ® II Clear | 10.0 | 10.0 |
| Total Tablet Weight | 1275 | 1175 |

Tablet 15 contained 200 mg of sucrose in the pull layer and 220 mg of POLYOX™ WSR N-60K in the push layer. Tablet 16 contained 200 mg of sucrose in the pull layer and 132 mg of POLYOX™ WSR Coagulant in the push layer.

Tablets 15 and 16 were made according to the procedure described in Example 1. FIG. 7 compares dissolution profiles of Tablets 15 and 16, measured using USP Apparatus I at 37° C., in a 500 ml dissolution medium containing 0.1 N HCL and 5% glycerol. It was observed that Tablets 15 containing 220 mg of POLYOX™ WSR N-60K in the push layer provided higher dissolution and better drug recovery compared to tablet 16 containing 132 mg of POLYOX™ WSR Coagulant in the push layer.

Example 12: Oral Bioavailability of Liothyronine from Tablet 1 (2×50 mc Gm), Tablet 2 (2×50 mc Gm), and CYTOMEL® (2×50 mc Gm)

A randomized, open label, balanced, three treatment, three period, three sequence, single dose, three way crossover, bioequivalence study of liothyronine sodium tablets 50 mcg (Dose: 2×50 mcg) was conducted in healthy volunteers under fed conditions to evaluate and compare PK performance of extended release compositions of the disclosure, using Tablet 1 (2×50 mc gm) and Tablet 2 (2×50 mc gm) with the marketed IR product, CYTOMEL® (2×50 mc gm). First period was followed by a 19-day washout period, and second period was followed by 21 day washout period.

TABLE 14

| | Pharmacokinetic (PK) Results of T3 | | | | | | |
|---|---|---|---|---|---|---|---|
| PK Parameters (Units) | Mean | | | | | Tablet 1: CYTOMEL ® (T/R) | Tablet 2: CYTOMEL ® (T/R) |
| | Tablet 1 N | | Tablet 2 N | | CYTOMEL ® N | | |
| Cmax (ng/ml) | 23 | 1.695 | 23 | 1.536 | 24 | 3.884 | 43.65 | 39.55 |
| AUC0-t (ng · hr/ml) | 23 | 28.872 | 23 | 26.853 | 24 | 42.834 | 67.41 | 62.69 |
| AUC0-∞ (ng · hr/ml) | 14 | 45.406 | 13 | 37.238 | 17 | 44.917 | 101.09 | 82.90 |

The data from this study (Table 14/FIG. 8) demonstrates that Tablet 1 and Tablet 2 provide therapeutic concentration (e.g., from about 0.8 ng/ml to about 2 ng/ml) of T3 for at least about 15 hours and provide substantially reduced burst release (about 50% reduction in $C_{max}$) as compared to CYTOMEL®.

Example 13: Oral Bioavailability of Liothyronine Sodium from Tablet 3 (2×50 mc Gm), Tablet 4 (2×50 mc Gm), and CYTOMEL® (2×50 mc Gm)

A randomized, open label, balanced, three treatment, three period, three sequence, single dose, three way crossover, bioequivalence study of liothyronine sodium tablets 50 mcg (Dose: 2×50 mcg) was conducted in healthy volunteers under fed conditions to evaluate and compare PK performance of extended release compositions of the disclosure, using Tablet 3 (2×50 mc gm) and Tablet 4 (2×50 mc gm), with the marketed IR product, CYTOMEL® (2×50 mc gm). First period was followed by a 19-day washout period, and second period was followed by a 21-day washout period.

TABLE 15

| | | | Pharmacokinetic (PK) Results of T3 | | |
|---|---|---|---|---|---|
| PK | | Mean | | Tablet 3: | Tablet 4: |
| Parameters | Tablet 3 | Tablet 4 | CYTOMEL ® | CYTOMEL ® | CYTOMEL ® |
| (Units) | N | N | N | (T/R) | (T/R) |
| Cmax (ng/ml) | 19   2.143 | 18   2.241 | 19   4.329 | 49.53 | 51.79 |
| AUC0-t (ng · hr/ml) | 17   35.4 | 15   39.3 | 18   46.3 | 76.55 | 84.81 |
| AUC0-∞ (ng · hr/ml) | 17   41.0 | 15   47.4 | 18   50.8 | 80.80 | 93.4 |

The data from this study (Table 15/FIG. 9) demonstrates that Tablet 4 provides therapeutic plasma concentration (e.g., from about 0.8 ng/ml to about 2 ng/ml) of T3 for at least about 15 hours and provide substantially reduced burst release as compared to CYTOMEL®. The data further demonstrates that Tablet 4 (125 mg coating weight gain) shows faster release and improved bioavailability compared to Tablet 3 (200 mg coating weight gain).

Example 14: Steady State Simulation at Day 7—Once-a-Day Administration of Tablet 3 (2×50 mc Gm) Vs Tablet 4 (2×50 mc Gm) Vs CYTOMEL® (2×50 mc Gm)

A steady state plasma concentration of T3 at day 7 was simulated, with administration of Tablet 3 (50 mcg×2) vs Tablet 4 (50 mcg×2) vs CYTOMEL (50 mcg×2).

TABLE 16

| Composition | $AUC_{144-168}$ | $AUC_{0-\infty}$ |
|---|---|---|
| CYTOMEL ® | 54.8 | 50.8 |
| Tablet 3 | 45.0 | 41.0 |
| Tablet 4 | 52.4 | 47.4 |
| Tablet 3/CYTOMEL | 82.2 | 80.7 |
| Tablet 4/CYTOMEL | 95.7 | 93.3 |

Table 16/FIG. 10 demonstrates that Tablet 3 (50 mc gm×2) and Tablet 4 (50 mcg×2) provide T3 plasma concentration of between 0.8 ng/ml and 3 ng/ml at steady state (SS). The data further demonstrates that $AUC0-\infty$ (in vivo) for Tablets 3 and 4 are comparable to corresponding $AUC_{144-168}$ at steady state.

TABLE 17

| Table No. | Cav (Steady State) | Cmin (Steady State) | Cmax (Steady State) | Fluctuation Index (FI) |
|---|---|---|---|---|
| CYTOMEL ® | 2.2 | 1.0 | 4.5 | 1.363 |
| Tablet 3 | 1.8 | 1.1 | 2.4 | 0.722 |
| Tablet 4 | 2.1 | 1.4 | 2.6 | 0.571 |

Data from Table 17 demonstrates that compositions of the disclosure exhibit FI of less than 1, e.g., about 0.722 and about 0.571. In contrast, FI of CYTOMEL® is above 1, e.g., about 1.36.

Example 15: Effect of CaSo4 on Stability of Liothyronine Sodium

The present Example compares storage stability at 2, 3, 6, and 7.5 months of Tablet 3 (with CaSO4 based intermediate granules) and Tablet 4 (with HPMC based intermediate granules).

TABLE 18

| | | 2 Month | | | 3 Month | |
|---|---|---|---|---|---|---|
| Tablet No. | Initial Assay | 5° C. | 25° C./ 60% RH | 30° C./ 65% RH | 5° C. | 25° C./ 60% RH | 30° C./ 65% RH |
| 3 | 88.2 | 91.8 | 84.7 | 84.9 | 91.1 | 86.9 | 82.4 |
| 4 | 99.4 | 94.3 | 95.8 | 92.3 | 96.8 | 96.5 | 96.4 |

TABLE 19

| | | 6 Month | | | 7.5 Month | |
|---|---|---|---|---|---|---|
| Tablet No. | Initial Assay | 5° C. | 25° C./ 60% RH | 30° C./ 60% RH | 5° C. | 25° C./ 60% RH | 30° C./ 60% RH |
| 3 | 88.2 | 90.1 | 82.3 | 77.8 | NA | NA | NA |
| 4 | 99.4 | 94.9 | 95.3 | 90.7 | NA | 94.9 | 95.9 |

Data from Tables 18 and 19 suggest that Tablet 4 with HPMC based granules (without CaSO4.2H2O) provided acceptable assay on storage for at least 7.5 months.

Example 16: Effect of Wet Granulation on Stability of Liothyronine Sodium

The present Example compares storage stability at 2 months of tablets comprising Drug Intermediate Granules (made by wet granulation and containing HPMC and BHT) and tablets comprising Drug intermediate blend (made via dry blending method and without BHT).

TABLE 20

| | | 2 Month | |
|---|---|---|---|
| | Initial | 5° C. | 25° C./60% RH | 30° C./65% RH |
| | | Wet Granulation (HPMC + BHT) | | |
| Total Impurity | 1.07 | 0.8 | 1.12 | 1.35 |
| | | Dry Mix (HPMC) | | |
| Total Impurity | 0.84 | NA | 0.81 | 0.77 |

Data from Table 20 shows that dry mix compositions provide better storage stability compared to compositions made by wet granulation-solvent based granulation had negative effect on storage stability of liothyronine salt and drug product.

The present disclosure is well adapted to attain the ends and advantages mentioned, as well as those that are inherent therein. The particular embodiments disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above can be altered or modified, and all such variations, including but not limited to substitution of different thyroid hormones, are considered within the scope and spirit of the present disclosure. Various publications, patents, and patent application are cited herein, the contents of which are hereby incorporated-by-reference herein in their entireties.

The invention claimed is:

1. An osmotic, floating, gastroretentive composition comprising:
a) a multilayer core comprising:
(i) a pull layer comprising liothyronine or a pharmaceutically acceptable salt thereof, an acid, and a gas-generating agent, and
(ii) a push layer; and
b) a permeable, elastic membrane comprising at least one orifice and covering at least a portion of the multilayer core;
wherein the permeable, elastic membrane comprises a copolymer of ethyl acrylate, methyl methacrylate and trimethylammonioethyl methacrylate chloride, and a plasticizer,
wherein the composition comprises an osmogen in either the pull layer, the push layer, or both,
wherein the at least one orifice is in fluid communication with the pull layer, and
wherein the composition does not include a semipermeable membrane.

2. The composition of claim 1, wherein the permeable elastic membrane comprises a copolymer of ethyl acrylate, methyl methacrylate and trimethylammonioethyl methacrylate chloride in a weight ratio of about 1:2:0.2.

3. The composition of claim 1, wherein the permeable elastic membrane comprises a copolymer of ethyl acrylate, methyl methacrylate and trimethylammonioethyl methacrylate chloride in a weight ratio of about 1:2:0.1.

4. The composition of claim 1, wherein the a plasticizer is selected from the group consisting of triethyl citrate, triacetin, polyethylene glycol, propylene glycol, dibutyl sebacate, and mixtures thereof.

5. The composition of claim 1, wherein the acid is an organic acid selected from the group consisting of succinic acid, citric acid, acetic acid, malic acid, benzoic acid, stearic acid, tartaric acid, boric acid, and mixtures thereof.

6. The composition of claim 1, wherein each of the pull layer and the push layer further comprises a swellable, water-soluble polymer.

7. The composition of claim 6, wherein the swellable, water-soluble polymer in the push layer is a polyethylene oxide polymer having an average molecular weight of greater than or equal to 600,000 Da.

8. The composition of claim 7, wherein the polyethylene oxide polymer has an average molecular weight of about 600,000 Da, about 700,000 Da, about 800,000 Da, about 900,000 Da, about 1,000,000 Da, about 2,000,000 Da, about 3,000,000 Da, about 4,000,000 Da, about 5,000,000 Da, about 6,000,000 Da, or about 7,000,000 Da.

9. The composition of claim 6, wherein the swellable, water-soluble polymer in the pull layer is selected from the group consisting of hypromellose, sodium carboxymethyl cellulose, carbomers, and mixtures thereof.

10. The composition of claim 9, wherein the swellable, water-soluble polymer is hypromellose.

11. The composition of claim 10, wherein the hypromellose is a mixture of a low-viscosity hypromellose having a viscosity, in 2% aqueous solution at 25° C., of less than or equal to 5000 cp, and a high-viscosity hypromellose with a viscosity, in 2% aqueous solution at 25° C., of greater than 5,000 cp.

12. The composition of claim 11, wherein the low-viscosity hypromellose and the high-viscosity hypromellose are present in a low-viscosity hypromellose:high-viscosity hypromellose weight ratio from 60:40 to 99:1.

13. The composition of claim 10, wherein the swellable, water-soluble polymer is a low-viscosity hypromellose having a viscosity, in 2% aqueous solution at 25° C., of less than or equal to 5000 cp.

14. The composition of claim 9, wherein the swellable, water-soluble polymer is sodium carboxy methyl cellulose.

15. The composition of claim 1, wherein the composition provides a sustained release and maintains a plasma concentration of from about 0.5 ng/ml to about 3 ng/ml of liothyronine or a pharmaceutically acceptable salt thereof, for at least 6 hours.

16. The composition of claim 1, wherein the composition comprises from about 1 µg to about 200 µg of liothyronine or a pharmaceutically acceptable salt thereof.

17. A method of treating hypothyroidism in a patient in need thereof, the method comprising administering to the patient, an osmotic, floating, gastroretentive composition comprising:
a) a multilayer core comprising:
(i) a pull layer comprising liothyronine or a pharmaceutically acceptable salt thereof, an acid, and a gas-generating agent, and
(ii) a push layer; and
b) a permeable elastic membrane comprising at least one orifice and covering at least a. portion of the multilayer core;
wherein the permeable, elastic membrane comprises a copolymer of ethyl acrylate, methyl methacrylate and trimethylammonioethyl methacrylate chloride, and a plasticizer,
wherein the composition comprises an osmogen in either the pull layer, the push layer, or both,
wherein the at least one orifice is in fluid communication with the pull layer, and
wherein the composition does not include a semipermeable membrane.

18. The method of claim 17, wherein the composition is administered once-a-day.

19. The method of claim 18, wherein the composition is administered as a single dose comprising a single dosage unit.

20. The method of claim 18, wherein the composition is administered as a single dose comprising multiple dosage units.

21. A method for making an the composition of claim 1, the method comprising
making a pull layer blend and a push layer blend;
horizontally pressing the pull layer blend and the push layer blend into a bilayered tablet core containing a pull layer and a push layer;

coating the bilayered tablet core with a permeable elastic membrane; and. drilling orifice in the permeable elastic membrane, wherein the pull layer blend comprises a drug intermediate blend and an extragranular component, wherein die drug intermediate blend comprises liothyronine or a pharmaceutically acceptable salt thereof, wherein the extragranular component comprises an acid, a gas generating agent, and an osmogen, wherein the permeable, elastic membrane comprises a copolymer of ethyl acrylate, methyl methacrylate and trimethylammonioethyl methacrylate chloride, and a plasticizer, wherein the orifice is in fluid communication with the pull layer, and wherein the composition does not include a semipermeable membrane.

22. The method of claim 21, wherein the drug intermediate blend is a dry blend.

23. The method of claim 22, wherein the drug intermediate blend comprises liothyronine granules.

24. The method of claim 23, wherein the liothyronine granules are made via wet granulation.

25. The method of claim 23, wherein the liothyronine granules are made via dry granulation.

* * * * *